(12) United States Patent
Tang et al.

(10) Patent No.: US 10,940,188 B2
(45) Date of Patent: Mar. 9, 2021

(54) COMPOUNDS AND METHODS FOR TREATMENT AND PREVENTION OF FLAVIVIRUS INFECTION

(71) Applicants: FLORIDA STATE UNIVERSITY RESEARCH FOUNDATION, INC., Tallahassee, FL (US); The United States of America, as represented by the Secretary, Department of Health and Human Services, Bethesda, MD (US); THE JOHNS HOPKINS UNIVERSITY, Baltimore, MD (US)

(72) Inventors: Hengli Tang, Tallahassee, FL (US); Emily M. Lee, Tallahassee, FL (US); Yichen Cheng, Tallahassee, FL (US); Yi Zhou, Tallahassee, FL (US); Wei Zheng, Rockville, MD (US); Ruili Huang, Rockville, MD (US); Miao Xu, Rockville, MD (US); Wenwei Huang, Rockville, MD (US); Menghang Xia, Rockville, MD (US); Hongjun Song, Baltimore, MD (US); Guo-Li Ming, Baltimore, MD (US); Zhexing Wen, Atlanta, GA (US)

(73) Assignees: FLORIDA STATE UNIVERSITY RESEARCH FOUNDATION, INC., Tallahassee, FL (US); THE UNITED STATES OF AMERICA AS REPRESENTED BY THE SECRETARY, DEPARTMENT OF HEALTH AND HUMAN SERVICES, Bethesda, MD (US); THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/779,132

(22) Filed: Jan. 31, 2020

(65) Prior Publication Data
US 2020/0164051 A1 May 28, 2020

Related U.S. Application Data

(63) Continuation of application No. 15/650,568, filed on Jul. 14, 2017.

(60) Provisional application No. 62/430,107, filed on Dec. 5, 2016, provisional application No. 62/380,778, filed on Aug. 29, 2016, provisional application No. 62/374,467, filed on Aug. 12, 2016, provisional application No. 62/366,855, filed on Jul. 26, 2016, provisional application No. 62/363,238, filed on Jul. 16, 2016.

(51) Int. Cl.
*A61K 38/55* (2006.01)
*A61K 31/24* (2006.01)
*A61K 31/609* (2006.01)
*A61K 38/43* (2006.01)
*A61K 45/06* (2006.01)
*C07C 239/02* (2006.01)
*C07C 239/08* (2006.01)
*A61K 38/00* (2006.01)

(52) U.S. Cl.
CPC .............. *A61K 38/55* (2013.01); *A61K 31/24* (2013.01); *A61K 31/609* (2013.01); *A61K 38/43* (2013.01); *A61K 45/06* (2013.01); *C07C 239/02* (2013.01); *C07C 239/08* (2013.01); *A61K 38/00* (2013.01); *Y02A 50/30* (2018.01)

(58) Field of Classification Search
CPC ..................................................... A61K 38/55
See application file for complete search history.

(56) References Cited

U.S. PATENT DOCUMENTS 5,033,252 A  7/1991  Carter
5,052,558 A  10/1991 Carter
(Continued)

FOREIGN PATENT DOCUMENTS

WO  WO-2006/121467  11/2006
WO  WO-2007/002051  1/2007
(Continued)

OTHER PUBLICATIONS

Low et al., Antiviral Activity of Emetine Dihydrochloride Against Dengue Virus Infection, 2009, Journal of Antivirals & Antiretrovirals, vol. 1(1), pp. 062-071 (Year: 2009).*

(Continued)

*Primary Examiner* — Kortney L. Klinkel
*Assistant Examiner* — Tori Strong
(74) *Attorney, Agent, or Firm* — Saliwanchik, Lloyd & Eisenschenk

(57) ABSTRACT

The present invention concerns the use of compounds for the treatment or prevention of Flavivirus infections, such as Zika virus infections. Aspects of the invention include methods for treating or preventing Flavivirus virus infection, such as Zika virus infection, by administering a compound or class of compound disclosed herein, such as a niclosamide compound, an emricasan compound, a cyclin-dependent kinase inhibitor, a proteasome inhibitor, or a combination of two or more of the foregoing, to a subject in need thereof; methods for inhibiting Flavivirus infections such as Zika virus infections in a cell in vitro or in vivo; pharmaceutical compositions; packaged dosage formulations; and kits for treating or preventing Flavivirus infections, such Zika virus infections.

18 Claims, 32 Drawing Sheets

(56) References Cited

U.S. PATENT DOCUMENTS

| | | | |
|---|---|---|---|
| 5,323,907 | A | 6/1994 | Kalvelage |
| 8,507,498 | B2 | 8/2013 | Wabnitz et al. |
| 9,040,529 | B2 | 5/2015 | Greff et al. |
| 10,555,942 | B2 | 2/2020 | Tang et al. |
| 2005/0203029 | A1 | 9/2005 | Schubert et al. |
| 2014/0148377 | A1 | 5/2014 | Bakare |
| 2014/0255426 | A1 | 9/2014 | Silvestri et al. |
| 2015/0210712 | A1 | 7/2015 | Blumberg et al. |
| 2016/0030403 | A1 | 2/2016 | Dow et al. |
| 2017/0157219 | A1 | 6/2017 | Hodge, III |
| 2017/0190700 | A1 | 7/2017 | Bakare et al. |

FOREIGN PATENT DOCUMENTS

| | | |
|---|---|---|
| WO | WO-2008/033466 | 3/2008 |
| WO | WO 2009/143297 | 11/2009 |
| WO | WO-2016/004166 | 1/2016 |
| WO | WO 2017/120225 | 7/2017 |
| WO | WO 2017/223491 | 12/2017 |

OTHER PUBLICATIONS

Araujo, L.M., Ferreira, M.L. and Nascimento, O.J., "Guillain-Barre syndrome associated with the Zika virus outbreak in Brazil," *Arq. Neuropsiquiatr.*, 2016, vol. 74, 253-255.

Asghar, U. et al., "The history and future of targeting cyclin-dependent kinases in cancer therapy," *Nat. Rev. Drug Discov.*, 2015, vol. 14, No. 2, pp. 130-146.

Barreyro, F.J. et al., "The pan-caspase inhibitor Emricasan (IDN-6556) decreases liver injury and fibrosis in a murine model of non-alcoholic steatohepatitis," *Liver Int.*, 2015, vol. 35, pp. 953-966.

Brennand, K.J. et al., "Modelling schizophrenia using human induced pluripotent stem cells," *Nature*, 2011, vol. 473, pp. 221-225.

Cao-Lormeau, V.M. et al., "Guillain-Barre Syndrome outbreak associated with Zika virus infection in French Polynesia: a case-control study," *Lancet*, 2016, vol. 387, pp. 1531-1539.

Cao-Lormeau, V.M. et al., "Zika virus, French polynesia, South pacific, 2013," *Emerg. Infect. Dis.*, 2014, vol. 20, pp. 1085-1086.

Chen, C.Z. et al., "High-throughput Giardia lamblia viability assay using bioluminescent ATP content measurements," *Antimicrob. Agents Chemother.*, 2011, vol. 55, pp. 667-675.

Cugola, F.R. et al., "The Brazilian Zika virus strain causes birth defects in experimental models," *Nature*, 2016, vol. 534, pp. 267-271.

Dang, J. et al., "Zika Virus Depletes Neural Progenitors in Human Cerebral Organoids through Activation of the Innate Immune Receptor TLR3," *Cell Stem Cell*, 2016, vol. 19, No. 2, pp. 258-265.

Debnath, A. et al., "A high-throughput drug screen for Entamoeba histolytica identifies a new lead and target," *Nat. Med.*, 2012, vol. 18, pp. 956-960.

Dick, G.W., Kitchen, S.F. and Haddow, A.J., "Zika virus. I. Isolations and serological specificity," *Trans. R. Soc. Trop. Med. Hyg.*, 1952, vol. 46, pp. 509-520.

Dou, Q.P. et al., "Overview of Proteasome Inhibitor-Based Anticancer Therapies: Perspective on Bortezomib and Second Generation Proteasome Inhibitors versus Future Generation Inhibitors of Ubiquitin-Proteasome System," *Curr. Cancer Drug Targets*, 2014, vol. 14, No. 6, pp. 517-536.

Driggers, R.W. et al., "Zika Virus Infection with Prolonged Maternal Viremia and Fetal Brain Abnormalities," *N. Engl. J. Med.*, 2016, vol. 374, No. 22, pp. 2142-2151.

Duffy, M.R. et al., "Zika virus outbreak on Yap Island, Federated States of Micronesia," *N. Engl. J. Med.*, 2009, vol. 360, pp. 2536-2543.

Fang, J. et al., "Identification of three antiviral inhibitors against Japanese encephalitis virus from library of pharmacologically active compounds 1280," *PLOS ONE*, 2013, vol. 8, e78425.

Garcez, P.P. et al., "Zika virus impairs growth in human neurospheres and brain organoids," *Science*, 2016, vol. 352, pp. 816-818.

Hamel, R. et al., "Biology of Zika Virus Infection in Human Skin Cells," *J. Virol.*, 2015, vol. 89, pp. 8880-8896.

He, S. et al., "Repurposing of the antihistamine chlorcyclizine and related compounds for treatment of hepatitis C virus infection," *Sci. Transl. Med.*, 2015, vol. 7, No. 282, 282ra49, 12 pages.

Heymann, D.L. et al., "Zika virus and microcephaly: why is this situation a PHEIC?," *Lancet*, 2016, vol. 387, pp. 719-721.

Huang, R. et al., "The NCGC pharmaceutical collection: a comprehensive resource of clinically approved drugs enabling repurposing and chemical genomics," *Sci. Transl. Med.*, 2011, vol. 3, No. 80, 80ps16.

Johansen, L.M. et al., "A screen of approved drugs and molecular probes identifies therapeutics with anti-Ebola virus activity," *Sci. Transl. Med.*, 2015, vol. 7, No. 290, 290ra89.

Jurgeit, A. et al., "Niclosamide is a proton carrier and targets acidic endosomes with broad antiviral effects," *Plos Pathog.*, 2012, vol. 8, e1002976.

Kouznetsova, J. et al., "Identification of 53 compounds that block Ebola virus-like particle entry via a repurposing screen of approved drugs," *Emerg. Microbes Infect.*, 2014, vol. 3, No. 12, e84.

Lazear, H.M. et al., "A Mouse Model of Zika Virus Pathogenesis," *Cell Host & Microbe*, 2016, vol. 19, No. 5, pp. 720-730.

Li et al. "Existing drugs as broad-spectrum and potent inhibitors for Zika virus by targeting NS2B-NS3 interaction" *Cell Res.*, 2017, 27:1046-1064.

Li, C. et al., "Zika Virus Disrupts Neural Progenitor Development and Leads to Microcephaly in Mice," *Cell Stem Cell*, 2016, vol. 19, No. 1, pp. 120-126.

Malumbres, M. et al., "CDK inhibitors in cancer therapy: what is next?," *Trends in Pharmacological Sciences*, Epub Dec. 4, 2007, vol. 29, No. 1, pp. 16-21.

Manasanch, E.E. et al., "Proteasome inhibitors in cancer therapy," *Nature Reviews Clinical Oncology*, 2017, vol. 14, No. 7, pp. 417-433.

Miner, J.J. et al., "Zika Virus Infection during Pregnancy in Mice Causes Placental Damage and Fetal Demise," *Cell*, 2016, vol. 165, pp. 1081-1091.

Mlakar, J. et al., "Zika Virus Associated with Microcephaly," *N. Engl. J. Med.*, 2016, vol. 374, pp. 951-958.

Mook, R.A. et al., "Structure-activity studies of Wnt/β-catenin inhibition in the Niclosamide chemotype: Identification of derivatives with improved drug exposure," *Bioorg. Med. Chem.*, 2015, vol. 23, No. 17, pp. 5829-5838.

Musso, D., "Zika Virus Transmission from French Polynesia to Brazil," *Emerg. Infect. Dis.*, 2015, vol. 21, 1887.

Nowakowski, T.J. et al., "Expression Analysis Highlights AXL as a Candidate Zika Virus Entry Receptor in Neural Stem Cells," *Cell Stem Cell*, 2016, vol. 18, pp. 591-596.

Pan, J.-X. et al., "Niclosamide, an antihelminthic agent, demonstrates antitumor activity by blocking multiple signaling pathways of cancer stem cells," *Chin. J. Cancer*, 2012, vol. 31, No. 4, pp. 178-184.

Pockros, P.J. et al., "Oral IDN-6556, an antiapoptotic caspase inhibitor, may lower aminotransferase activity in patients with chronic hepatitis C," *Hepatology*, 2007, vol. 46, pp. 324-329.

Qian, X. et al., "Brain-Region-Specific Organoids Using Minibioreactors for Modeling ZIKV Exposure," *Cell*, 2016, vol. 165, pp. 1238-1254.

Rasmussen, S.A., Jamieson, D.J., Honein, M.A. and Petersen, L.R., "Zika Virus and Birth Defects—Reviewing the Evidence for Causality," *N. Engl. J. Med.*, 2016, vol. 374, 1981-1987.

Rossi, S.L., et al., "Characterization of a Novel Murine Model to Study Zika Virus," *Am. J. Trop. Med. Hyg.*, 2016, vol. 94, No. 6, pp. 1362-1369.

Sanchez-Martinez, C. et al., "Cyclin dependent kinase (CDK) inhibitors as anticancer drugs," *Bioorganic & Medicinal Chemistry Letters*, 2015, vol. 25, No. 17, pp. 3420-3435.

Schang, L.M., St. Vincent, M.R. and Lacasse, J.J., "Five years of progress on cyclin-dependent kinases and other cellular proteins as potential targets for antiviral drugs," *Antivir. Chem. Chemother.*, 2006, vol. 17, pp. 293-320.

(56) References Cited

OTHER PUBLICATIONS

Shiffman, M.L. et al., "Clinical trial: the efficacy and safety of oral PF-03491390, a pancaspase inhibitor—a randomized placebo-controlled study in patients with chronic hepatitis C," *Aliment. Pharmacol. Ther.*, 2010, vol. 31, pp. 969-978.

Sun, W. et al., "Chemical signatures and new drug targets for gametocytocidal drug development," *Sci. Rep.*, 2014, vol. 4, 3743.

Sun, W. et al., "Rapid identification of antifungal compounds against Exserohilum rostratum using high throughput drug repurposing screens," *PLOS ONE*, 2013, vol. 8, No. 8, e70506.

Sun, W., Sanderson, P.E. and Zheng, W., "Drug combination therapy increases successful drug repositioning," *Drug Discov. Today*, 2016, vol. 21, No. 7, pp. 1189-1195.

Tang, H. et al., "Zika Virus Infects Human Cortical Neural Progenitors and Attenuates Their Growth," *Cell Stem Cell*, 2016, vol. 18, pp. 587-590.

Topol, A. et al., "Increased abundance of translation machinery in stem cell-derived neural progenitor cells from four schizophrenia patients," *Transl. Psychiatry*, 2015, vol. 5, e662.

Wang, Y., Jadhav, A., Southal, N., Huang, R. and Nguyen, D.T., "A grid algorithm for high throughput fitting of dose-response curve data," *Curr. Chem. Genomics*, 2010, vol. 4, pp. 57-66.

Wen, Z., et al., "Synaptic dysregulation in a human iPS cell model of mental disorders," *Nature*, 2014, vol. 515, pp. 414-418.

Wu, C.J. et al., "Inhibition of severe acute respiratory syndrome coronavirus replication by niclosamide," *Antimicrob. Agents Chemother.*, 2004, vol. 48, pp. 2693-2696.

Xu, M. et al., "Identification of small-molecule inhibitors of Zika virus infection and induced neural cell death via a drug repurposing screen," *Nature Medicine*, 2016, vol. 22, No. 10, pp. 1101-1110.

Zhang, J.H., Chung, T.D. and Oldenburg, K.R., "A Simple Statistical Parameter for Use in Evaluation and Validation of High Throughput Screening Assays," *J. Biomol. Screen.*, 1999, vol. 4, pp. 67-73.

Zheng, W., Thorne, N. and McKew, J.C., "Phenotypic screens as a renewed approach for drug discovery," *Drug Discov. Today*, 2013, vol. 18, pp. 1067-1073.

Tomizawa, M. et al. "Niclosamide suppresses hepatoma cell proliferation via the Wnt pathway" *Onco Targets and Therapy*, 2013, 6:1685-1693.

Berge, S.M. et al. "Pharmaceutical Salts" *Journal of Pharmaceutical Science*, 1977, 66(1):1-19.

Elgart, A. et al. "Improved oral bioavailability of BCS class 2 compounds by self nano-emulsifying drug delivery systems (SNEDDS): the underlying mechanisms for amiodarone and talinolol" *Pharm Res.*, 2013, 30(12):3029-3044.

Gourinat, A-C. et al. "Detection of Zika Virus in Urine" *Emerg Infect Dis*, 2015, 21(1):84-86.

Kansara, H. et al. "Techniques used to enhance bioavailability of BCS class II drugs: a review" *Int. J. Drug Dev. & Res.*, 2015, 7(1):82-93.

Khamkar, G.S. "Self micro emulsifying drug delivery system (SMEED) o/w microemulsion for BCS Class II drugs: an approach to enhance oral bioavailability" *International Journal of Pharmacy and Pharmaceutical Sciences*, 2011, 3(Suppl. 3):1-3.

Musso, D. et al. "Detection of Zika virus in saliva" *J Clin Virol*, 2015, 68:53-55.

Reddy, M.S. et al. "Solubility enhancement of fenofibrate, a BCS class II drug, by self emulsifying drug delivery systems" *International Research Journal of Pharmacy*, 2011, 2(11):173-177.

Singh, N. et al. "Techniques for bioavailability enhancement of BCS class II drugs: a review" *International Journal of Pharmaceutical and Chemical Sciences*, 2013, 2(2):1092-1101.

Wu, K-M. "A New Classification of Prodrugs: Regulatory Perspectives" *Pharmaceuticals*, 2009, 2(3):77-81.

Cheung, Y. et al. "Antiviral activity of lanatoside C against dengue virus infection" *Antiviral Res.*, 2014, 111:93-99.

Craig, N. "Fish tapeworm and sushi" *Canadian Family Physician*, 2012, 58:654-658.

Toresdahl, B. et al. "Update on Zika Virus: Considerations for the Traveling Athlete" *Sports Health*, 2016, 8(5):438-443.

Dowall, S. D. et al. "A susceptible mouse model for Zika virus infection" *PloS Negl. Trop. Dis.*, May 5, 2016, pp. 1-13, 10(5):e0004658.

Dudley, D. M. et al. "A Rhesus Macaque Model of Asian-Lineage Zika Virus Infection" *Nature Communications*, 2016, pp. 1-9, vol. 28, No. 7.

Elkihel, L. et al. "Synthesis and orally macrofilaricidal evaluation of niclosamide lymphotropic prodrugs," *Arzneimittelforschung*, 1994, pp. 1259-1264, vol. 44, No. 11, Abstract.

Koide, F. et al. "Development of a Zika Virus Infection Model in Cynomolgus Macaques" *Frontiers in Microbiology*, 2016, pp. 1-8, vol. 7.

Kuno, G. et al. "Phylogeny of the Genus *Flavivirus*" *Journal of Virology*, Jan. 1998, pp. 73-83, vol. 72, No. 1.

Lasslo, A. et al. "Chemical and Pharmacologic Studies on Emetine and Quaternary Emetine Derivatives" *Journal of the American Pharmaceutical Association*, Jan. 1950, pp. 43-46, vol. 39, No. 1, Abstract.

Morrison, T. E. et al. "Animal Models of Zika Virus Infection, Pathogenesis, and Immunity" *J. Virol.*, 2017, pp. 1-15, vol. 91, No. 8.

Pyman, F. L. et al. "The Action of Certain Emetine Derivatives on Amoebae" *Journal of Pharmacology and Experimental Therapeutics*, Oct. 1917, pp. 237-241, vol. 10, No. 4.

Yang, S. et al. "Emetine inhibits Zika and Ebola virus infections through two molecular mechanisms: inhibiting viral replication and decreasing viral entry" *Cell Discovery*, 2018, p. 31 (14 pages), vol. 4.

\* cited by examiner

Emricasan

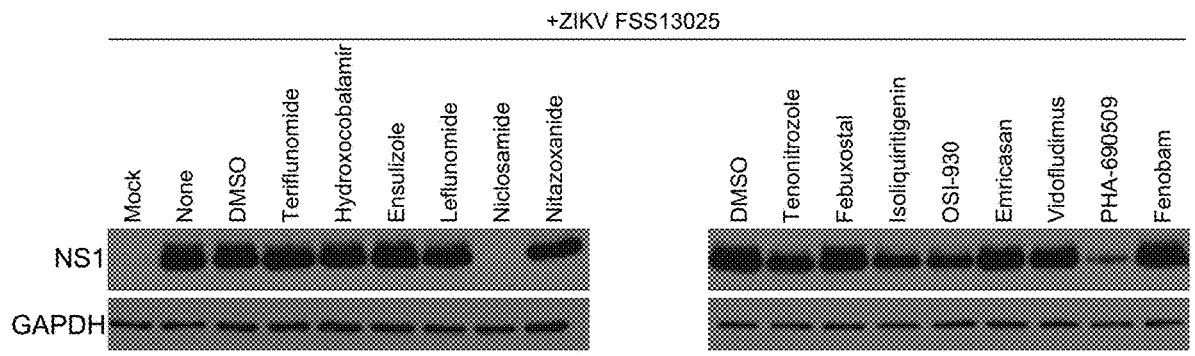
FIG. 2A-1  FIG. 2A-2
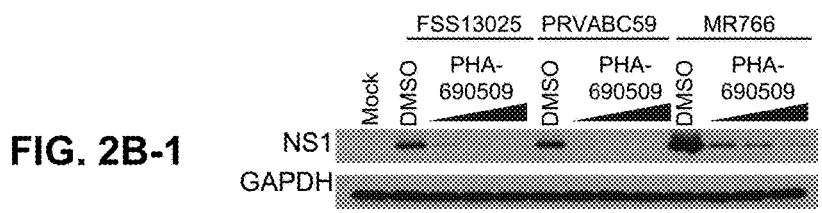
FIG. 2B-1
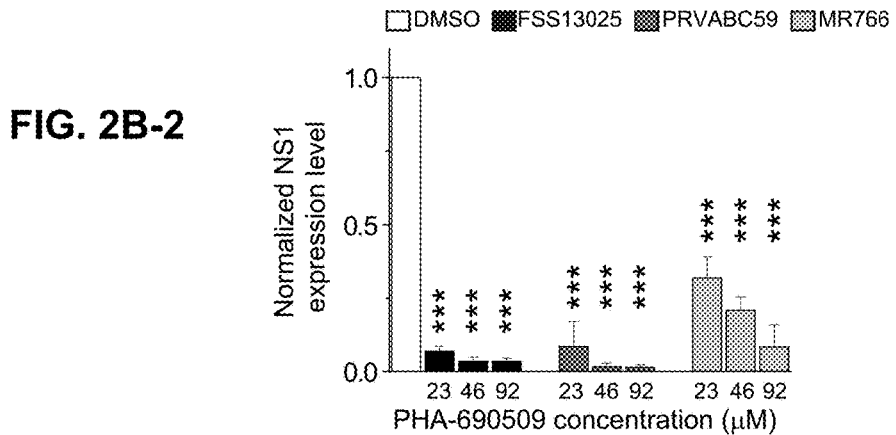
FIG. 2B-2

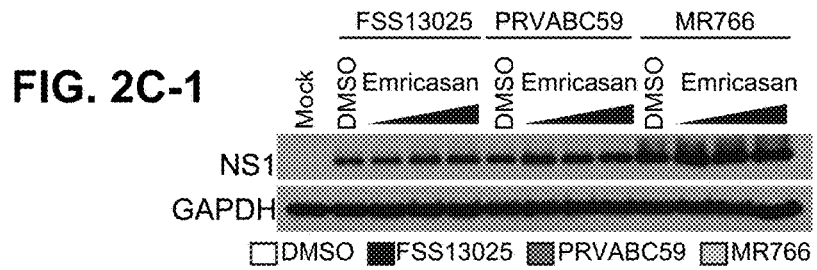
FIG. 2C-1
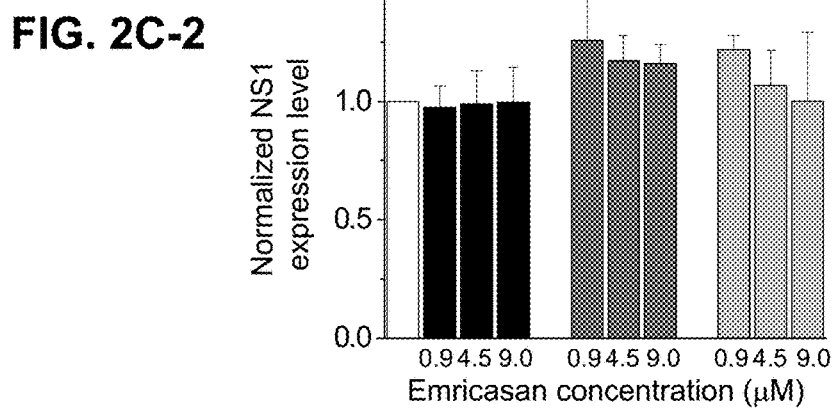
FIG. 2C-2
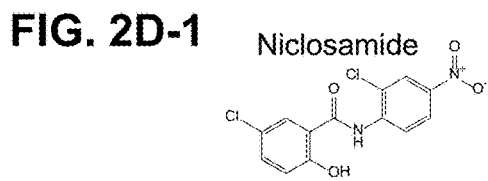
FIG. 2D-1 Niclosamide
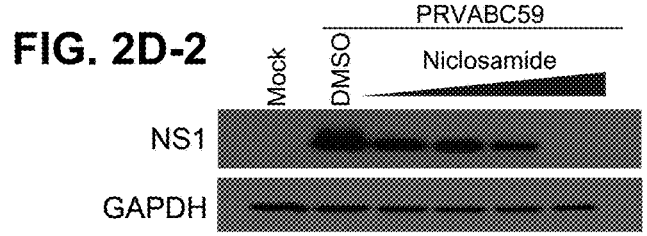
FIG. 2D-2
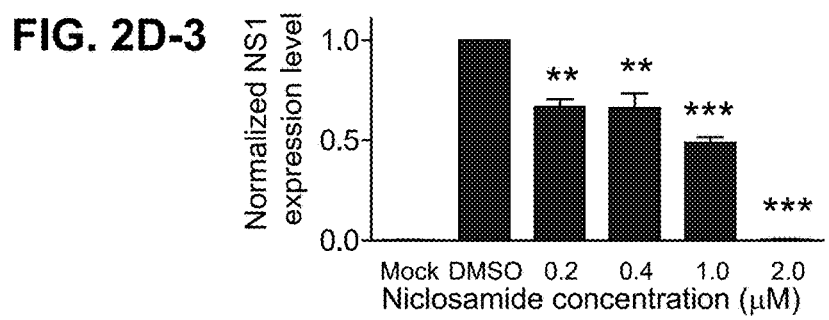
FIG. 2D-3

FIG. 3A
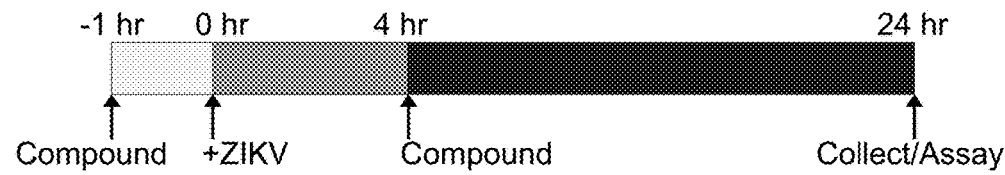
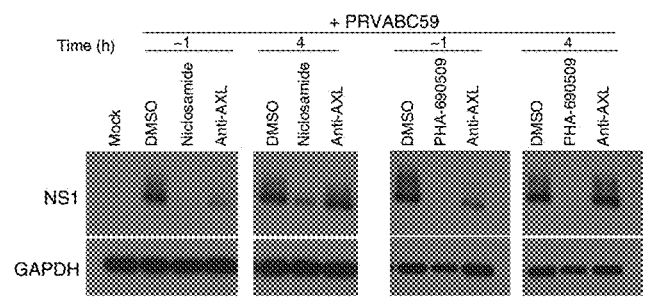
FIG. 3B
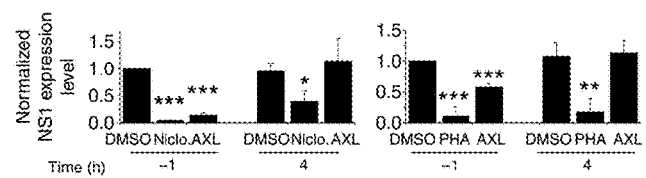
FIG. 3E

Alvocidib

PHA-793887

Dinaciclib

Seliciclib

PHA-690509

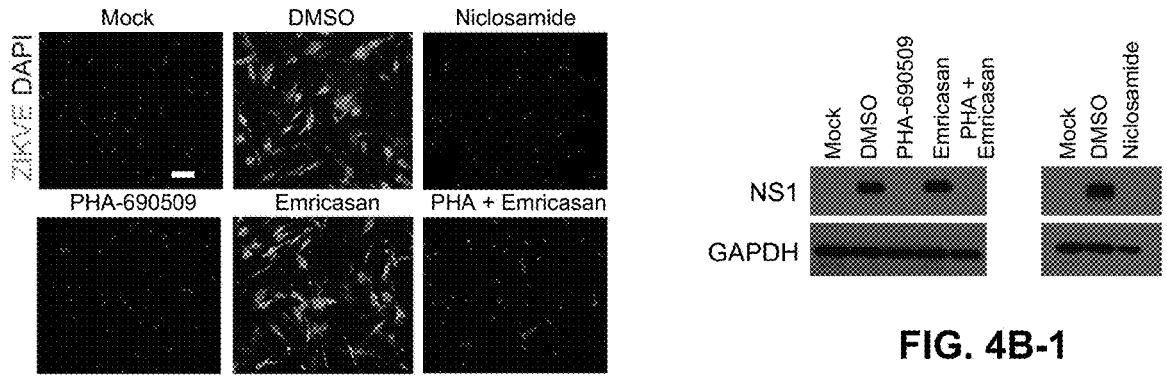
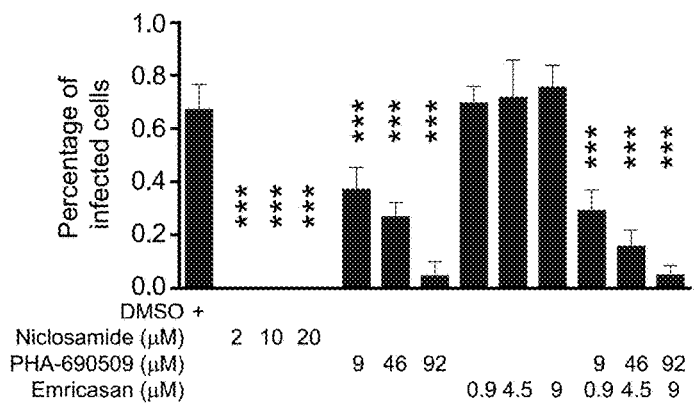
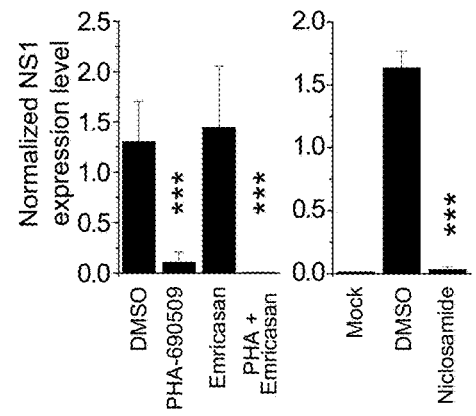
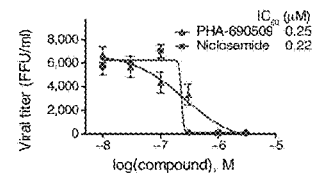
FIG. 4A-1
FIG. 4A-2
FIG. 4B-1
FIG. 4B-2
FIG. 4B-3

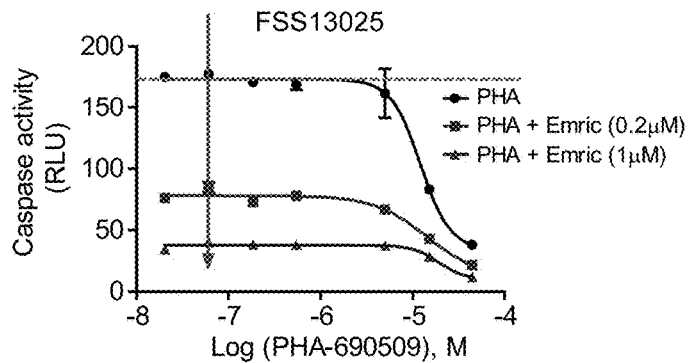
FIG. 4C-1
FIG. 4C-2
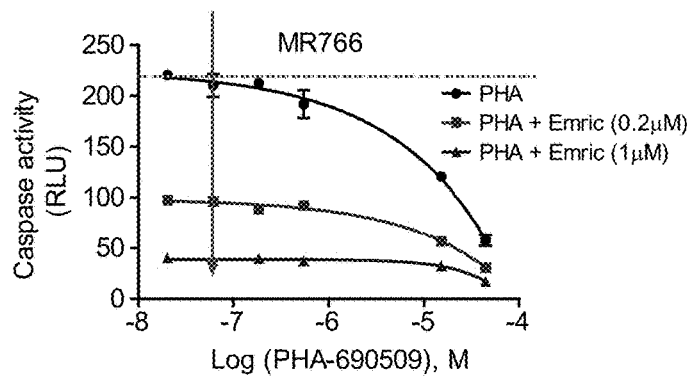
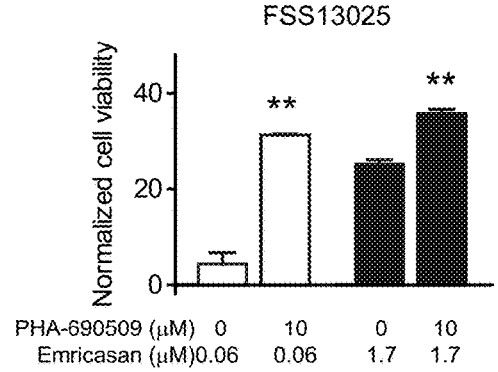
FIG. 4D-1
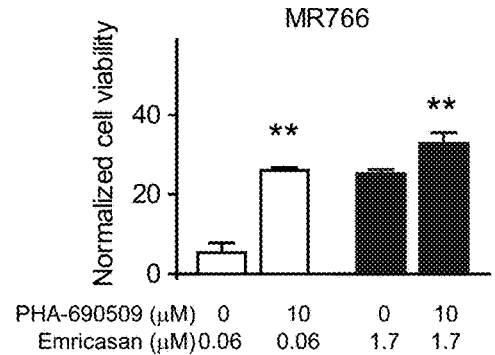
FIG. 4D-2

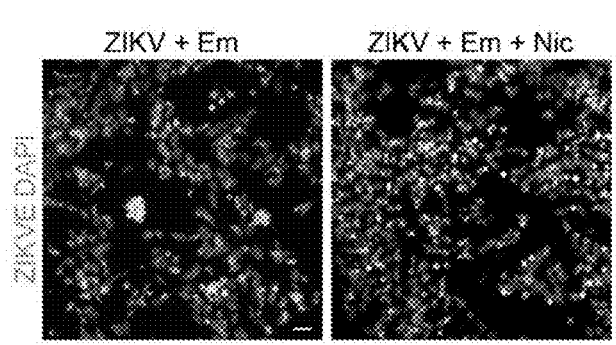
FIG. 8D
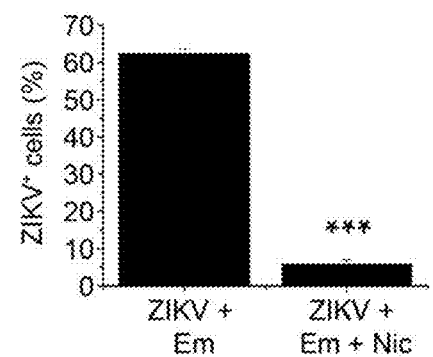
FIG. 8E
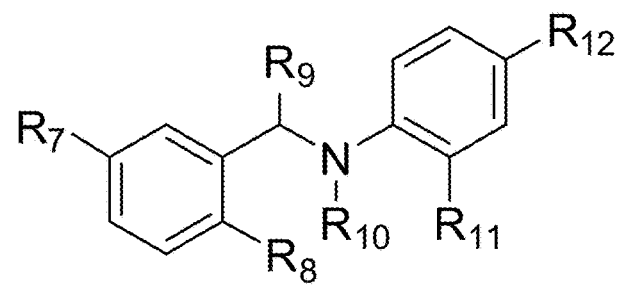
FIG. 9A          FIG. 9B
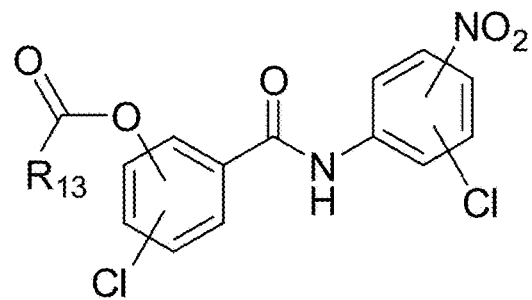      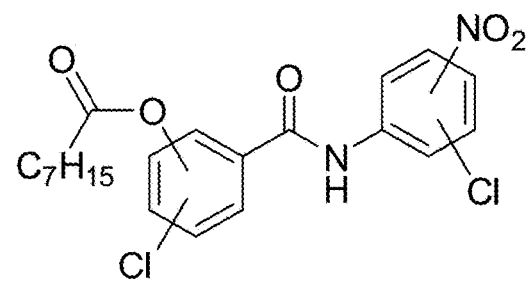
FIG. 9C          FIG. 9D

FIG. 16
| Compound ID | Compound Name | Structure |
|---|---|---|
| NCGC00015582-06 | Kenpaullone | 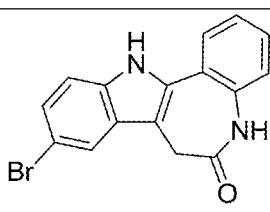 |
| NCGC00015763-09 | Olomoucine | 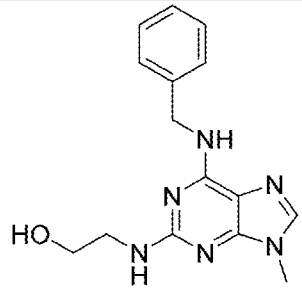 |
| NCGC00025219-04 | Purvalanol A | 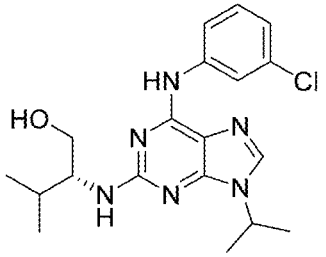 |
| NCGC00025220-03 | Purvalanol B | 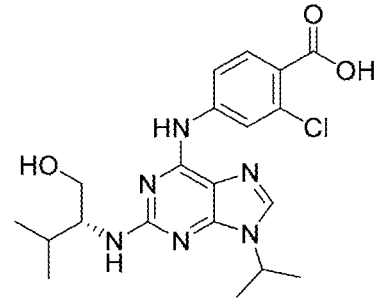 |
| NCGC00094374-05 | Seliciclib | 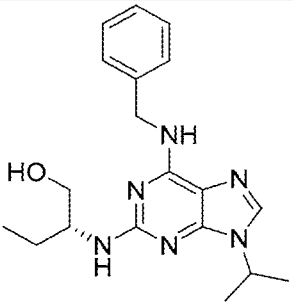 |

FIG. 16 continued
| Compound ID | Compound Name | Structure |
|---|---|---|
| NCGC00165844-02 | NU-6027 | 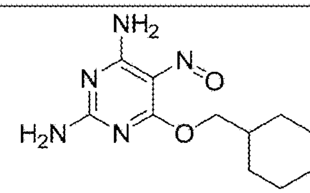 |
| NCGC00179302-02 | Indirubin | 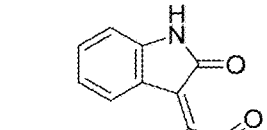 |
| NCGC00250401-01 | Flavopiridol | 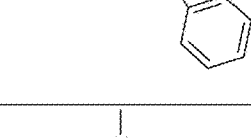 |
| NCGC00263091-01 | AT7519 | 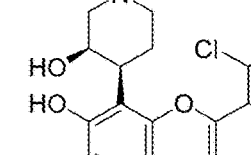 |
| NCGC00263129-01 | PD-0332991 | 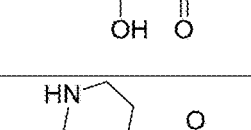 |
| NCGC00263167-02 | SNS-032 | 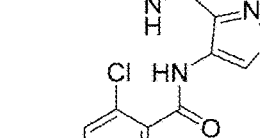 |

FIG. 16 continued
| Compound ID | Compound Name | Structure |
|---|---|---|
| NCGC00263168-01 | PHA-793887 | 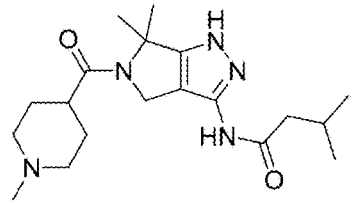 |
| NCGC00263191-01 | PHA-690509 | 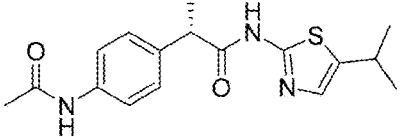 |
| NCGC00345809-01 | RGB-286147 | 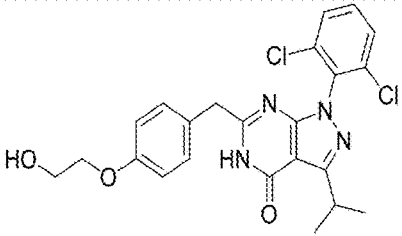 |
| NCGC00345852-01 | BS-194 | 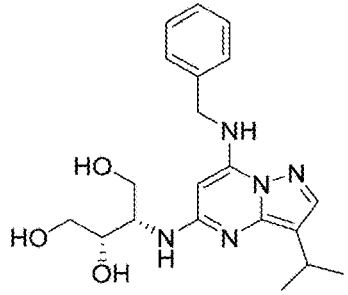 |
| NCGC00346553-01 | BS-181 | 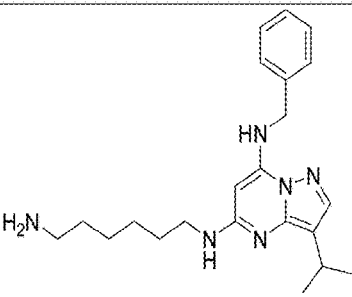 |
| NCGC00346617-01 | AZD-5438 | 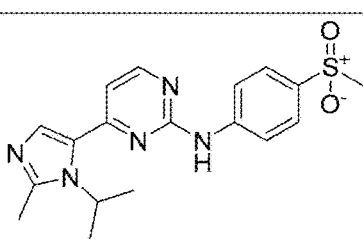 |

FIG. 16 continued

| Compound ID | Compound Name | Structure |
|---|---|---|
| NCGC00346632-01 | R-547 | 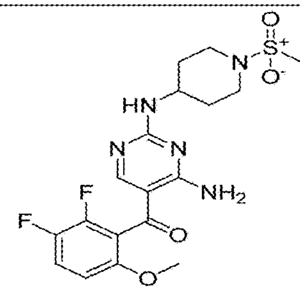 |
| NCGC00346656-01 | Dinaciclib | 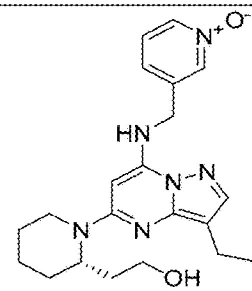 |
| NCGC00346673-01 | Milciclib | 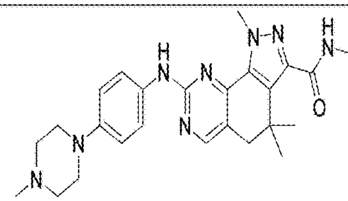 |
| NCGC00346693-01 | BMS-265246 | 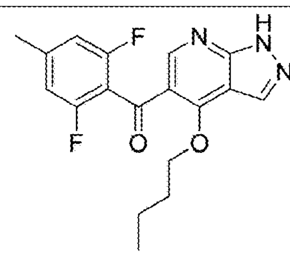 |
| NCGC00346827-01 | 7-Hydroxystaurosporine | 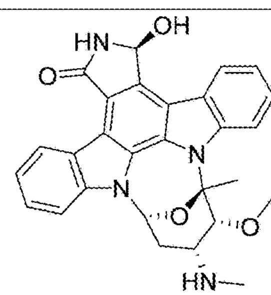 |
| NCGC00346940-01 | CGP-60474 | 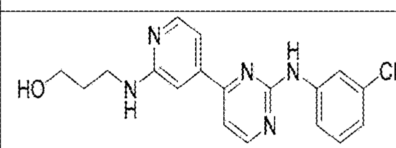 |

FIG. 16 continued

| Compound ID | Compound Name | Structure |
|---|---|---|
| NCGC00346946-01 | CDK9 inhibitor | 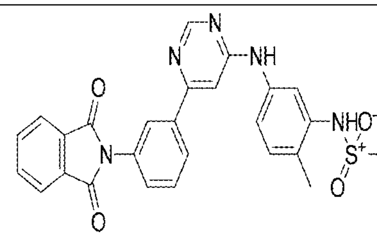 |
| NCGC00346950-01 | NU-6102 | 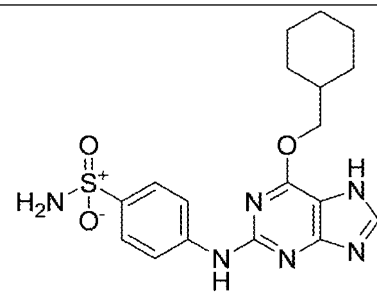 |
| NCGC00346951-01 | Fascaplysin | 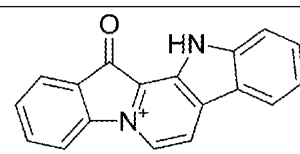 |
| NCGC00346952-01 | Cdk4/6 Inhibitor IV | 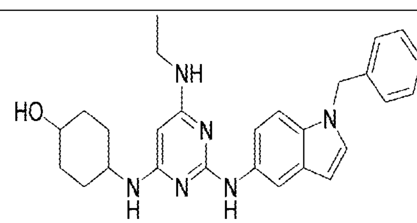 |

COMPOUNDS AND METHODS FOR TREATMENT AND PREVENTION OF FLAVIVIRUS INFECTION

CROSS-REFERENCE TO RELATED APPLICATIONS

The present application is a continuation of U.S. application Ser. No. 15/650,568, filed Jul. 14, 2017, which claims the benefit of U.S. Provisional Application Ser. No. 62/430,107, filed Dec. 5, 2016; 62/380,778, filed Aug. 29, 2016; 62/374,467, filed Aug. 12, 2016; 62/366,855, filed Jul. 26, 2016; and 62/363,238, filed Jul. 16, 2016, each of which is hereby incorporated by reference herein in its entirety, including any figures, tables, nucleic acid sequences, amino acid sequences, or drawings.

GOVERNMENT SUPPORT

This invention was made with government support under grant number TR000269 awarded by National Institutes of Health. The government has certain rights in this invention.

BACKGROUND OF THE INVENTION

Zika virus (ZIKV), a mosquito-borne flavivirus, has re-emerged and spread across the Western Hemisphere in the past year. First isolated in 1947 from a sentinel rhesus macaque in the Ziika Forest region of Uganda [1], ZIKV had remained in relative obscurity for many years until outbreaks in the Pacific islands and then the Americas in the past decade [2-4]. A large outbreak started in Brazil in late 2014 and is a growing public health concern [5]. Currently, active transmission has been reported in 58 countries and territories globally. About 20% of ZIKV infected individuals develop symptoms, which mostly resemble symptoms caused by other arboviruses, such as dengue viruses or chikungunya virus. Unlike these viruses, however, ZIKV causes congenital defects, including microcephaly [6,7], and is also associated with Guillain-Barré syndrome in infected adults [8,9].

BRIEF SUMMARY OF THE INVENTION

The present invention concerns the use of compounds for the treatment or prevention of Flavivirus infections, such as Zika virus infections. Aspects of the invention include methods for treating or preventing Flavivirus virus infection, such as Zika virus infection, by administering a niclosamide compound, an emricasan compound, a cyclin-dependent kinase inhibitor, a proteasome inhibitor, another compound or class of compounds disclosed herein, or a combination of two or more of the foregoing, to a subject in need thereof; methods for inhibiting Flavivirus infections such as Zika virus infections in a cell in vitro or in vivo; pharmaceutical compositions; packaged dosage formulations; and kits for treating or preventing Flavivirus infections, such Zika virus infections.

The inventors have identified a novel use for certain compounds in the treatment and prevention of Zika virus (ZIKV) infections and other Flavivirus infections. In some embodiments, the compounds are selected from among:

(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

In some embodiments, the compounds are selected from those in Tables 7-10 or FIGS. 9-22, or a prodrug, metabolite, or derivative thereof.

The inventors identified Niclosamide from a library of compounds used in a large scale compound screen measuring cell-death inhibition in ZIKV infected cells. However, the compound screen failed to identify Niclosamide as being highly effective against ZIKV-induced cell death. In spite of the initial negative results, the inventors chose to focus on Niclosamide due to its status as a FDA approved drug and category B pregnancy rating. By directly testing Niclosamide in human cell culture against ZIKV infection, the inventors have found strong evidence that Niclosamide is highly effective against ZIKV infection.

The inventors have also identified a novel use for CDK inhibitors, such as PHA690509, in having antiviral properties in Zika virus (ZIKV) infection. The inventors identified PHA690509 from a library of compounds used in a large scale compound screen (in collaboration with NIH) measuring cell-death inhibition in ZIKV infected cells. The compound screen identified PHA690509 as being highly effective against ZIKV-induced cell death. The inventors have also tested PHA690509 in several human cell culture systems (human neural progenitor cells, iPSC-derived astrocytes, organoids, and glioblastoma cells) against ZIKV infection, and have found strong evidence that PHA690509 is highly effective against ZIKV infection.

The inventors have also identified Emricasan, a pan-caspase inhibitor, as a compound that potently inhibits ZIKV-induced increase in caspase-3 activity and reduces cell death. The inventors confirmed its efficacy to protect human cortical neural progenitors in both monolayer and organoid cultures. PHA-690509, a cyclin-dependent kinase (CDK) inhibitor, and four structurally unrelated CDK inhibitors, inhibit ZIKV replication in human cells in a dose-dependent manner. In addition, Niclosamide, an FDA approved category B anthelmintic drug, inhibits ZIKV replication at sub-micromolar concentrations. Both CDK inhibitors and Niclosamide are effective in reducing ZIKV replication when added either before or after ZIKV exposure. Furthermore, a combination of two classes of compounds showed a synergistic effect in protecting human neural cells from ZIKV-induced cell death. The inventors' results demonstrate the effectiveness of this compound screening strategy and provide lead compounds for drug development against ZIKV and other Flavivirus.

BRIEF DESCRIPTION OF THE DRAWINGS

(FIG. 1B) Sample images of immunostaining (FIG. 1B-1) of forebrain-specific hNPCs for ZIKV envelop protein (ZIKVE; green) and cleaved-caspase 3 (Cas3; red) and DAPI (gray) 72 hours after ZIKV FSS-13025 infection (MOI=0.04-0.08; Scale bar: 20 µm), and quantification (FIG. 1B-2). Values represent mean±s.e.m. (n=3; P<0.01; Student's t-test). Sample images (FIG. 1C-1) of immunostaining of day 28 human forebrain-specific organoids for ZIKVE (green) and Cas3 (red) and DAPI (gray) 10 days after ZIKV FSS-13025 infection (Scale bar: 100 µm), and quantification (FIG. 1C-2). Values represent mean±s.e.m. (n=6; *P<0.001; Student's t-test).

FIGS. 2A-1, 2A-2, 2B-1, 2B-2, 2C-1, 2C-2, 2D-1, 2D-2, 2D-3, 2E-1, 2E-2, and 2F. Identification of PHA-690509 and Niclosamide as antiviral compounds. Screening of select compounds for antiviral activity against ZIKV infection was carried out. Glioblastoma SNB-19 cells were treated with indicated compound at 10×AC50 (determined in the primary caspase screen) for 1 hour prior to inoculation with FSS-13025 (at MOI=1). Cells were harvested 24 hours post infection and analyzed by Western blot for ZIKV-NS1 or GAPDH (FIGS. 2A-1 and 2A-2). Titration of PHA-690509 on glioblastoma cells for anti-ZIKV activity. Three strains of virus (FSS-13025, PRVABC59, and MR766; MOI=1) were tested. Shown are sample western blot images (FIG. 2B-1) and ImageJ quantification (FIG. 2B-2). Values represent mean±s.d. (n=3; *P<0.001; One-way ANOVA). Titration of Emricasan on SNB-19 cells for anti-ZIKV activity was conducted similarly (FIGS. 2C-1 and 2C-2). Values represent mean±s.d. (n=3; no significant differences were found; One-way ANOVA). Titration of Niclosamide (FIG. 2D-1) on SNB-19 cells for anti-ZIKV activity. Sample western blot (FIG. 2D-2) and ImageJ quantification (FIG. 2D-3) are shown for infection with the PRVABC59 strain (MOI=1). Results for additional strains are shown in FIGS. 6A-F. Values represent mean±s.d. (n=2; P<0.01; *P<0.001; One-way ANOVA). Secretion of ZIKV NS1 protein into the medium of infected cells was inhibited by anti-ZIKV compounds in a dosage-dependent manner. The concentration of NS1 in the medium of infected SNB-19 cells collected 24 hours post-infection was quantified by a ZIKV-NS1 ELISA kit (FIGS. 2E-1 and 2E-2). Values represent mean±s.d. (n=3; *P<0.001; One-way ANOVA). FIG. 2F shows a summary of titration of niclosamide and PHA-690509 on ZIKV production. SNB-19 cells were treated with each indicated compound at increasing concentrations for 1 hour before infection with PRVABC59 at a MOI=0.5 (n=3 cultures). Cell culture supernatant was collected 24 hours after infection, and infectious virions were quantified for focus-forming units (FFU) using Vero cells. Data represent mean±s.d. Curves represent best fits for calculating IC50 values, and the insets report the calculated IC50 value for each compound.

FIGS. 3A, 3B, 3C-1, 3C-2, 3C-3, 3C-4, 3C-5, 3D-1, 3D-2, and 3E. Time-of-addition compound treatments and blockade of ZIKV infection by additional CDK inhibitors. FIG. 3A shows a schematic illustration of time-of-addition experiment for Niclosamide and PHA-690509. Niclosamide and PHA-690509 inhibit ZIKV infection at a post-entry step. SNB-19 cells were treated with 10 µg/ml anti-AXL antibody, 2 µM Niclosamide, or 92 µM PHA-690509 for 1 hour prior or 4 hours post infection with PRVABC59 (MOI=1). Cells were harvested 24 hours post infection and analyzed by western blot for ZIKV-NS1 or GAPDH (shown in FIG. 3B). Structures of PHA-690509 and four structurally unrelated CDK inhibitors (Alvocidib, PHA-793887, Dinaciclib, and Seliciclib) are shown in FIGS. 3C-5, 3C-1, 3C-2, 3C-3, and 3C-4, respectively. Inhibition of ZIKV infection in CDK inhibitor-treated cells. SNB-19 cells were treated with the indicated compound at 92 µM for one hour prior to infection with FSS13025 or PRVABC59 (MOI=1). Cells were harvested 24 hours post infection and analyzed by western blot for ZIKV-NS1 or GAPDH. Shown are sample images and quantification (FIGS. 3D-1 and 3D-2). Values represent mean±s.d. (n=2; *P<0.01; One-way ANOVA). Quantification of NS1 protein band intensities, relative to those for GAPDH (n cultures), in FIG. 3B, are shown in FIG. 3E**. Data were normalized to those obtained for DMSO-treated cells. Values represent mean±s.d. *P<0.05; P<0.01; *P<0.001; by one-way ANOVA, as compared to DMSO-treated cells.

FIGS. 4A-1, 4A-2, 4B-1, 4B-2, 4B-3, 4C-1, 4C-2, 4D-1, and 4D-2. Niclosamide and PHA-690509 inhibit ZIKV infection in human astrocytes and forebrain-specific hNPCs. Sample immunostaining images of astrocytes treated with 2 µM Niclosamide, 92 µM PHA-690509, 9 µM Emricasan, or a combination of 92 µM PHA-690509 and 9 µM Emricasan for 1 hour prior to infection with PRVABC59 (MOI=0.5) are shown in FIG. 4A-1. Cells were fixed 24 hours post infection and stained for ZIKVE (green) and DAPI (blue). Scale bar: 50 µm. Also shown is the quantification of ZIKV-infected astrocytes with multiple compound concentrations (FIG. 4A-2). Values represent mean±s.d. (n=6; *P<0.001; One-way ANOVA). Shown in FIG. 4B-3 is virus production from compound-treated iPSC-derived human astrocytes (as in FIG. 2F) (n=3 cultures). Data represent mean±s.d. Niclosamide and PHA-690509 inhibit ZIKV infection in hNPCs. hNPCs were infected at a MOI of 0.1 and analyzed by Western blot 48 hours post infection for ZIKV-NS1 or GAPDH. Shown are sample images and quantification (FIGS. 4B-1 and 4B-2). Values represent mean±s.d. (n=2; *P<0.01; One-way ANOVA). Synergistic effect of Emricasan/PHA-690509 combination on improving cell viability in ZIKV infected astrocytes. Note that Emricasan and PHA-690509 inhibit the increased caspase-3 activity in a concentration-dependent manner in human astrocytes infected with FSS13025-ZIKV or MR766 ZIKV, and improve cell viability as measured by ATP production (FIGS. 4C-1, 4C-2, 4D-1, and 4D-2). Values represent mean±s.d. (n=3; **P<0.01; One-way ANOVA).

(FIG. 5A) Flowchart of caspase-3 activity and cell viability assays for compound screening. (FIG. 5B) Increased caspase-3 activity in the ZIKV infected hNPCs, SNB-19 cells, and human astrocytes. Values represent mean±s.d. (n=3; **P<0.01; One-way ANOVA). (FIG. 5C) Decreased cell viability after ZIKV infection for three days. Values represent mean±s.d. (n=3; *P<0.01; One-way ANOVA). (FIG. 5D) Schematic diagram of compound screening and hit follow-up process. (FIG. 5E) Summary of numbers of confirmed compounds in the caspase 3/7 activity assay. Thirty-five compounds were confirmed in all three cell types. (FIG. 5F) Summary of confirmed compounds in the cell viability assay that improved cell viability in cells infected with ZIKV.

FIG. 6A shows representative Western blot images of SNB-19 cells treated with compounds at 10×IC50 concentration (determined in primary caspase-3 screen) for 1 hour prior to infection with ZIKV-FSS13025 and harvested 24 hours later for NS1 detection. FIG. 6B shows representative Western blot images of SNB-19 cells treated with 2, 10, or 20 µM Niclosamide 1 hour prior to infection with indicated ZIKV strains and harvested 24 hours later and analyzed as in FIG. 6A. Dose-dependence of Niclosamide on ZIKV-NS1 protein levels is shown in FIG. 6C. Cells were treated with 0.02-2 µM Niclosamide, infected with PRVABC59, and analyzed as in FIG. 6B.

FIGS. 6D and 6E show dose-dependence of Niclosamide and PHA-690509 on intracellular ZIKV-RNA levels. Cells were treated with compounds at indicted concentrations for one hour then infected with ZIKV-FSS13025, and harvested 48 hours later for RNA purification. ZIKV RNA levels were measured using qRT-PCR and normalized to that with the DMSO treatment. Values represent mean+s.d. (n=3 cultures; P<0.01; *P<0.001; One-way ANOVA for comparison with the DMSO treatment). Niclosamide inhibits a post-entry step in the ZIKV infection lifecycle. SNB-19 cells were treated with 2 µM Niclosamide or DMSO for 1 hour prior to infection. Cells were incubated with viral inoculum at MOI=1 for 2 hours on ice, then at 37° C. (denoted as 0 hr time point). Cells were washed with PBS and total RNA was collected and purified at each time point for qRT-PCR analysis of ZIKV RNA. Relative ZIKV RNA levels after normalizing to GAPDH RNA in the same sample are plotted in FIG. 6F. Values represent mean+s.d. (n=3 cultures; P<0.01; *P<0.001; One-way ANOVA for comparison with the DMSO treatment).

FIGS. 7A, 7B-1, 7B-2, and 7B-3. Additional cyclic-dependent kinase inhibitors (CDKis) and non-CDK kinase inhibitors that were tested for antiviral activity. Chemical structures of nine additional CDKis that inhibited ZIKV infection are shown in FIG. 7A. Representative Western blot images of SNB-19 cells treated with 1 µM of each indicated compound for 1 hour prior to infection with ZIKV-FSS13025 and harvested 24 hours post infection, shown in FIG. 7B-1. FIG. 7B-2 shows chemical structures of four non-CDK kinase inhibitors tested on ZIKV infection. FIG. 7B-3 shows representative Western blot images of SNB-19 cells treated with 1 µM of each indicated non-CDK kinase inhibitor 1 hour prior to infection with PRVABC59 and harvested 24 hours post infection.

FIGS. 8A-8E. Additional benefit of combinatorial treatment with two classes of compounds. Human astrocytes were treated with DMSO, PHA-690509, Emricasan, or PHA-690509 and Emricasan at indicated concentrations for 1 hour prior to infection with ZIKV-F5513025. Cell lysates were harvested 24 hours post infection and analyzed for ZIKV-NS1 and GAPDH protein levels by western blot. Shown are representative Western blot images (FIG. 8A) and quantification (FIG. 8B). Data were normalized to that of the DMSO treatment. Values represent mean+s.d. (n=3 cultures; *P<0.001; One-way ANOVA for comparison with the DMSO treatment). Secreted NS1 levels from DMSO-, Niclosamide-, PHA-690509-, or Emricasan-treated astrocytes. Astrocytes were infected as in FIG. 8A and supernatants were collected 24 hours post infection for analysis by NS1 ELISA. Results are shown in FIG. 8C. Values represent mean+s.d. (n=3 cultures; *P<0.001; One-way ANOVA for comparison with the DMSO treatment). Combined treatment of hNPCs with Emricasan (Em) and Niclosamide (Nic). hNPCs were treated with 15 µM Emricasan 1 hour prior to addition of PRVABC59 (MOI=0.08). At 72 hours post infection, 1 µM Niclosamide or DMSO was added to hNPCs and cells were cultured for an additional 48 hours prior to staining with anti-ZIKVE. Shown in FIG. 8D are representative images of immunostaining for ZIKVE (green) and DAPI (gray, left; Scale bar: 20 µm) and quantification (FIG. 8E). Values represent mean+s.e.m. (n=3 cultures; ***P<0.001; One-way ANOVA).

FIGS. 9A-9D. Formulas encompassing Niclosamide and derivatives of Niclosamide (Formulas 1-4, respectively).

FIG. 16. Table of embodiments of CDK inhibitory compounds of the invention, with corresponding chemical structures, including Kenpaullone, Olomoucine, Purvalanol A, Purvalanol B, Seliciclib, NU-6027, Indirubin, Flavopiridol, AT7519, PD-0332991, SNS-032, PHA-793887, PHA-690509, RGB-286147, BS-194, BS-181, AZD-5438, R-547, Dinaciclib, Milciclib, BMS-265246, 7-Hydroxystaurosporine, CGP-60474, CDK9 inhibitor, NU-6102, Fascaplysin, and Cdk4/6 Inhibitor IV.

Values represent mean+s.e.m. (n=8 organoids; P>0.05; One-way ANOVA for comparison with the mock treatment).

Figures 1, 1A:
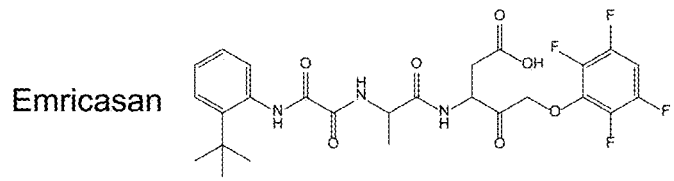
FIGS. 1A-1, 1A-2, 1A-3, 1B-1, 1B-2, 1C-1, and 1C-2. Emricasan suppresses cell death of ZIKV-infected human astrocytes and hNPCs in 2D monolayer cultures and 3D brain organoids. Emricasan (FIG. 1A-1) inhibits caspase-3 activity and improves cell viability in human astrocytes infected with three different strains of ZIKV in a concentration dependent manner. Value represent mean±s.d. (n=3). The curves (FIGS. 1A-2 and 1A-3) represent best fit.
Figures 1, 1A, 2:
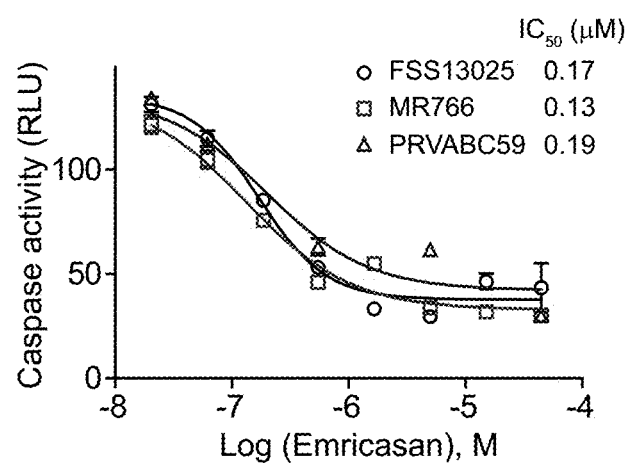
Figure 18A:
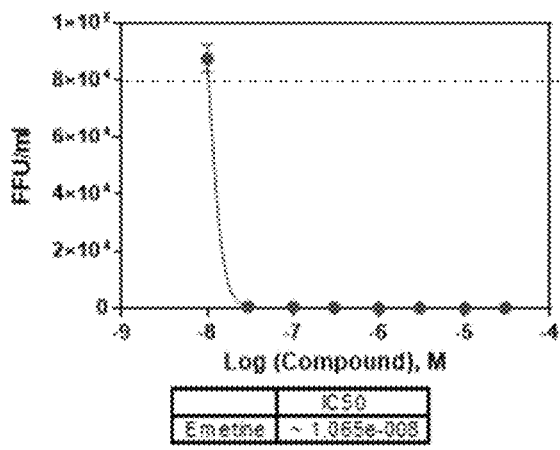
Figure 18B:
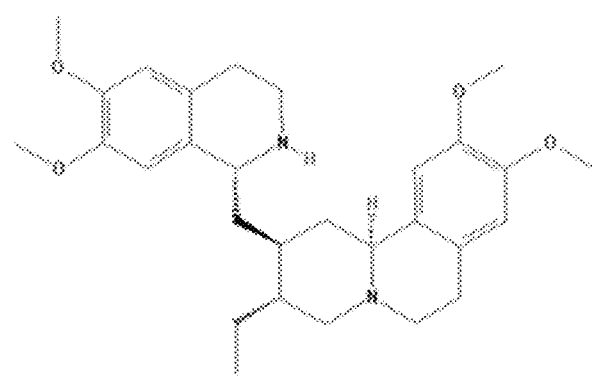
Figures 1, 18C:
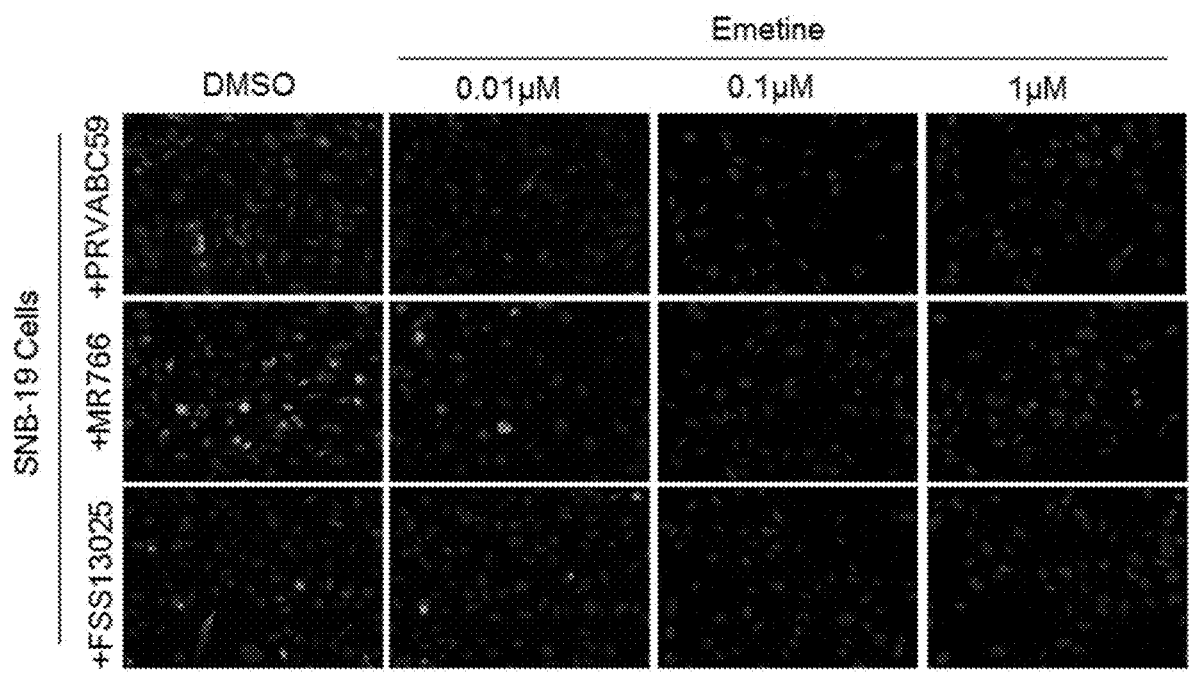
Figures 2, 18C:
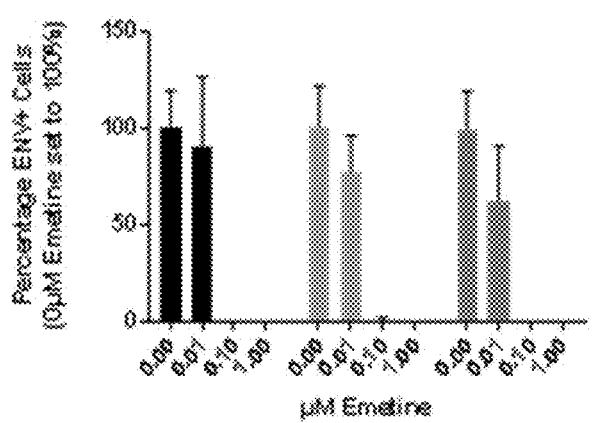
Figure 18D:
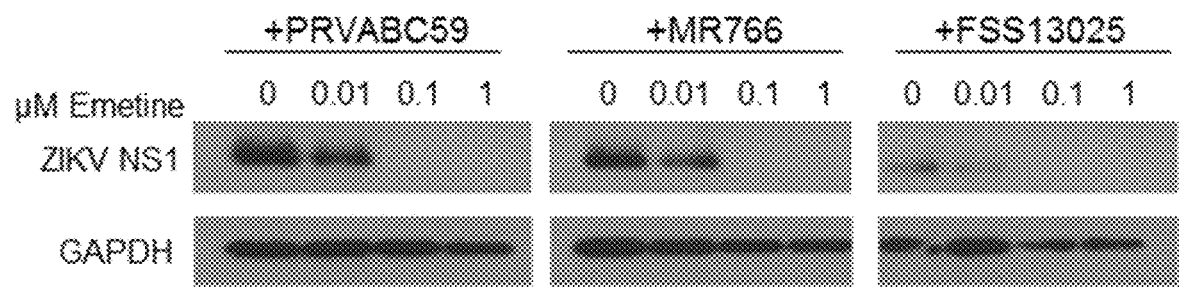
Figure 18E:
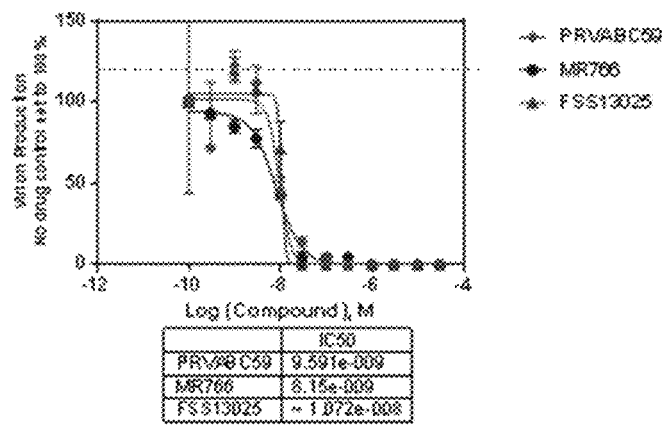
Figure 18F:
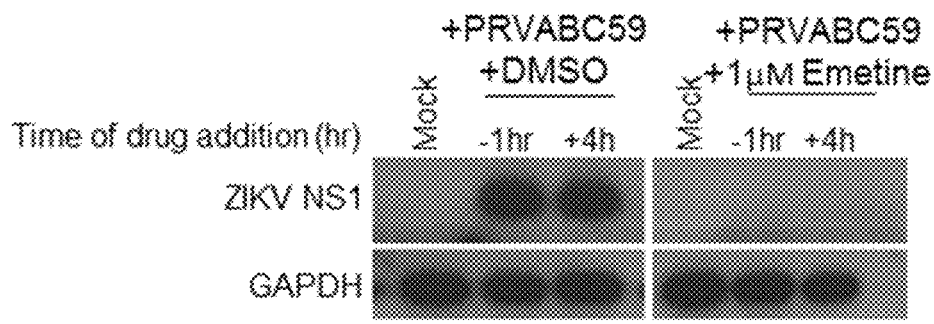
Figures 1, 18G:
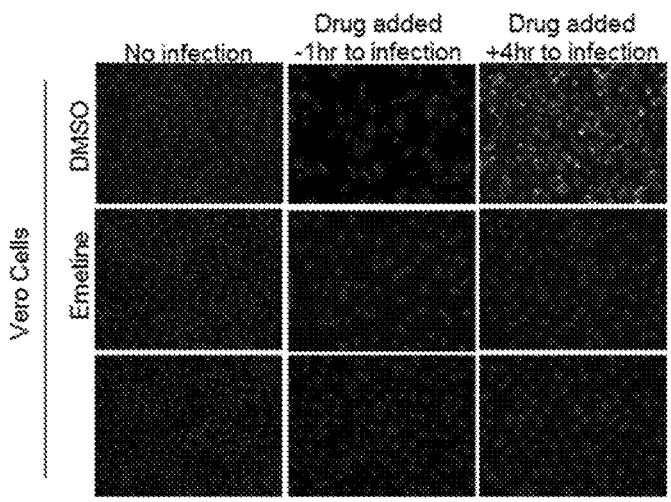
Figures 2, 18G:
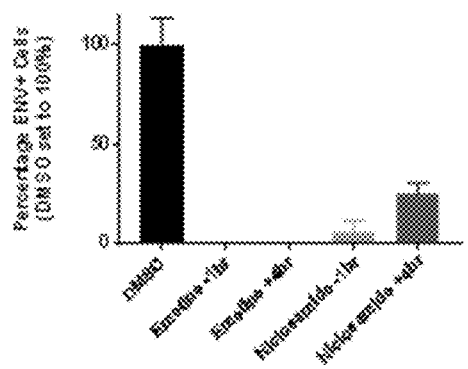

FIGS. 18A, 18B, 18C-1, 18C-2, 18D, 18E, 18F, 18G-1, and 18G-2. Antiviral activity of emetine against ZIKV infection. ZIKV production from human glioblastoma SNB-19 cells treated with increasing concentration of emetine. 24 hours post infection, supernatants from SNB-19 cells were titrated onto naïve vero cells plated in a monolayer in 96-well plates for infectious focus-forming unit assay as previously described and focus forming units quantified [47]. Results are shown in FIG. 18A. The chemical structure of emetine is shown in FIG. 18B. Emetine reduces ZIKV infection in a dosage dependent manner. Immunofluorescence (IF) staining (FIG. 18C-1) and quantification (FIG. 18C-2) of ZIKV positive SNB-19 cells following infection with one of three ZIKV strains and treatment with emetine at 0.01, 0.1, or 1 µM. Emetine is effective against all three ZIKV strains tested. FIG. 18D shows Western blot analysis of intracellular ZIKV NS1 levels in SNB-19 cells. FIG. 18E shows that infectious ZIKV production is reduced for all three strains of ZIKV tested in SNB-19 cells. IC50 for each strain is ≤~10 nM. Emetine is effective against ZIKV infection when added both before or after infection. FIG. 18F shows Western blot analysis of ZIKV NS1 protein levels in SNB-19 cells after a 24-hour infection. Drug was added at 1 µM either 1-hour prior to infection with PRV-ABC59-ZIKV, or 4-hours post infection with PRVABC59-ZIKV. FIG. 18G-1 shows IF staining of ZIKV-ENV vero cells after a 24-hour infection. Drug was added at 1 µM either 1-hour prior to infection with PRVABC59-ZIKV, or 4-hours post infection with PRVABC59-ZIKV. Percentage of ZIKV-ENV+ cells are shown in FIG. 18G-2.

Figure 19A:
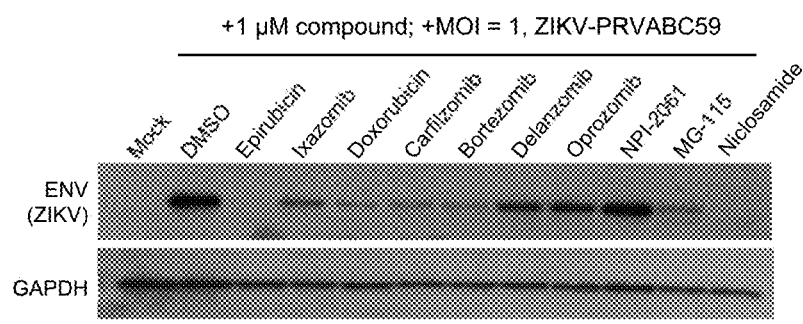
Figures 1, 19B:
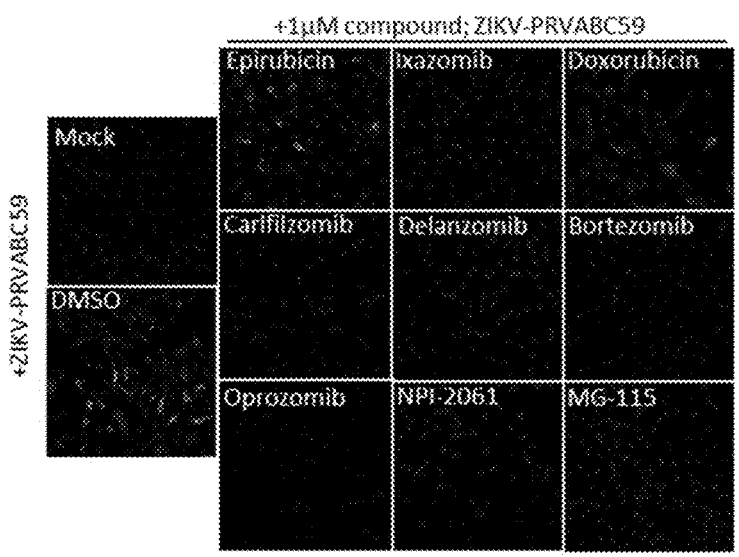
Figures 2, 19B:
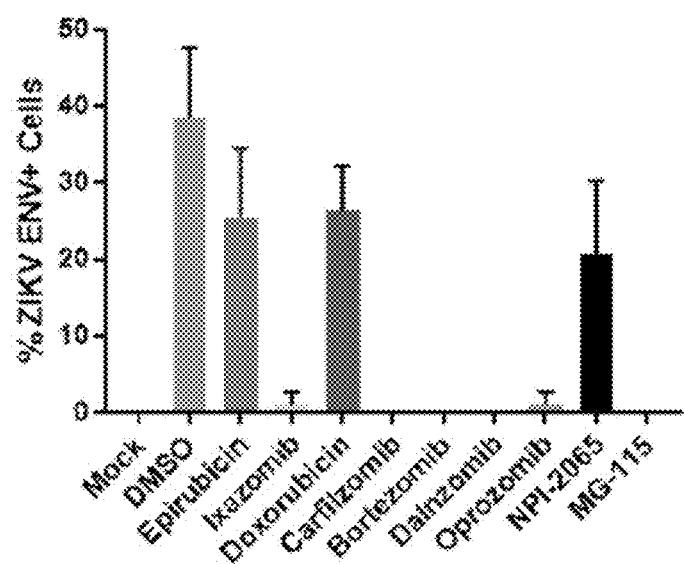
Figure 19C:
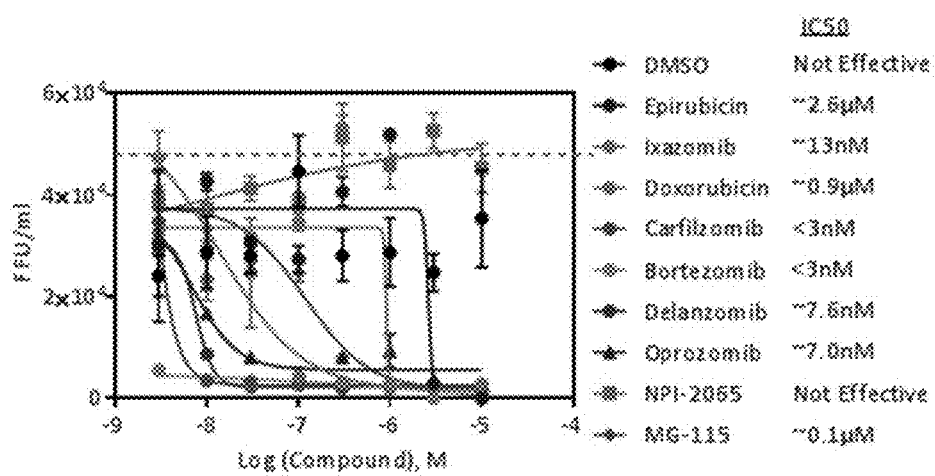
Figure 19D:
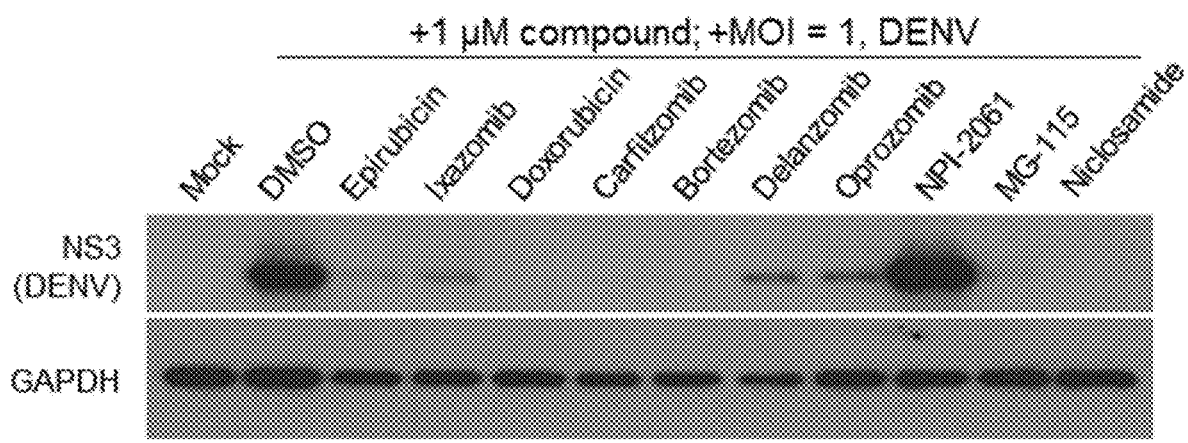
Figures 1, 19E:
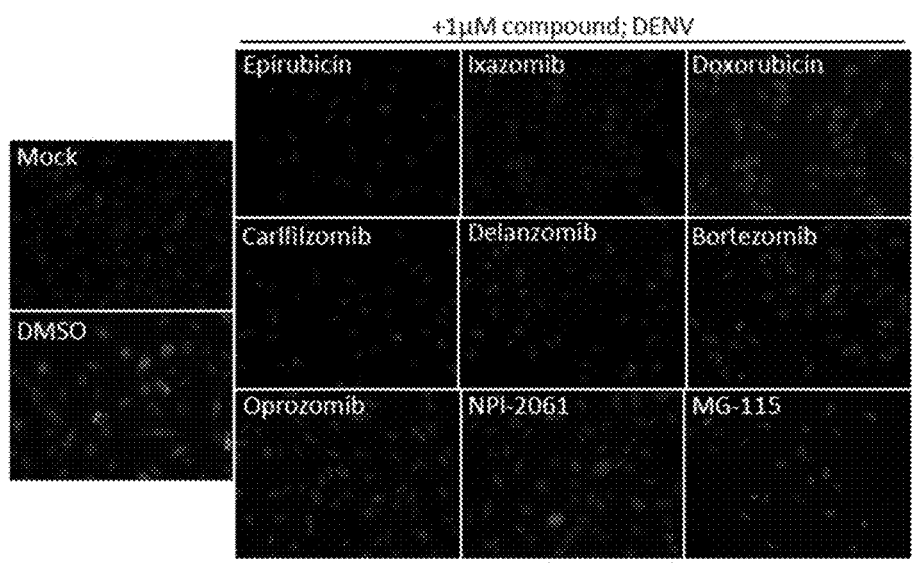
Figures 2, 19E:
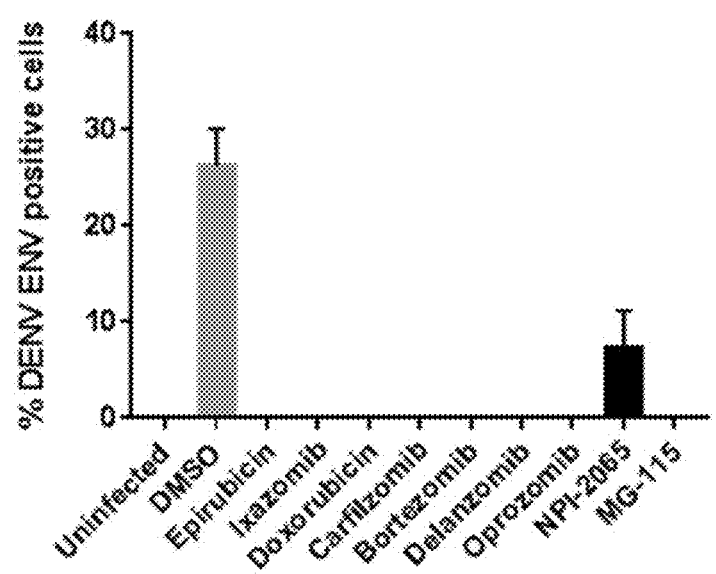

FIGS. 19A, 19B-1, 19B-2, 19C, 19D, 19E-1, and 19E-2. Antiviral activity of proteasome inhibitors against ZIKV and DENV infection. FIG. 19A shows Western blot analysis of ZIKV NS1 protein levels in SNB-19 cells after a 24-hour infection (strain PRVABC59, MOI=1). Cells were treated for 1 hour prior to addition of 1 µM indicated compound. FIG. 19B-1 shows immunofluorescence staining and quantification (FIG. 19B-2) of ZIKV-ENV positive SNB-19 cells after a 24-hour infection (strain PRVABC59, MOI=1). Cells were treated for 1 hour prior to addition of 1 µM indicated compound. ZIKV production from human glioblastoma SNB-19 cells treated with increasing concentration of indicated compound. 24-hours post infection, supernatants from SNB-19 cells were titrated onto naïve vero cells plated in a monolayer in 96-well plates for infectious focus-forming unit assay as previously described and focus forming units quantified [47], as shown in FIG. 19C. IC50s were calculated using graphpad PRISM software and listed next to the graph. FIG. 19D shows the Western blot analysis of DENV NS3 protein levels in SNB-19 cells after a 24-hour infection (DENV serotype II, MOI=0.2) Cells were treated for 1 hour prior to addition of 1 µM indicated compound. FIG. 19E-1 shows immunofluorescence staining and quantification (FIG. 19E-2) of DENV-ENV positive SNB-19 cells after a 24-hour infection (DENV serotype II, MOI=0.2). Cells were treated for 1 hour prior to addition of 1 µM indicated compound.

Figure 20:
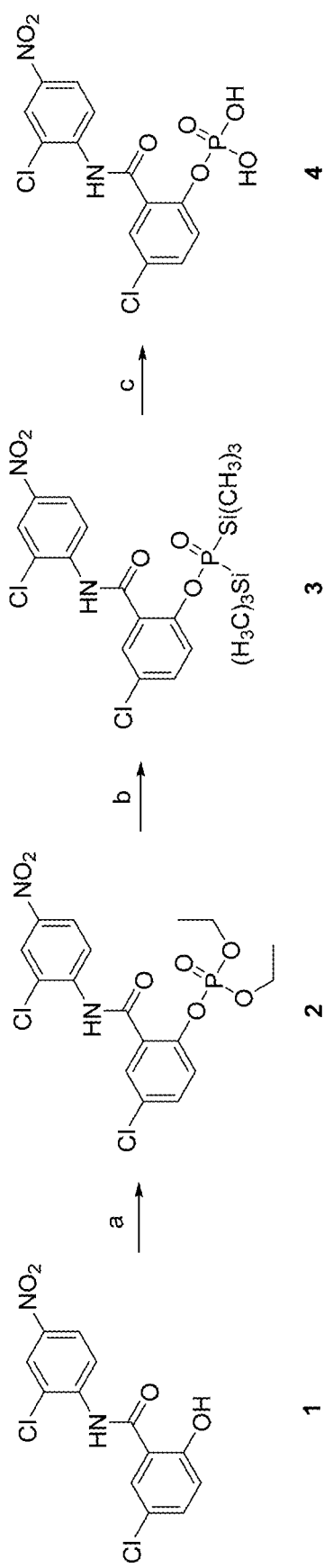

FIG. 20. Synthesis scheme for the niclosamide derivative p-niclosamide. Reagent and conditions: (a) (EtO)$_2$POH, DIPEA, CCl$_4$, DMAP, MeCN, −10° C.; (b) (CH$_3$)$_3$SiBr, CHCl$_3$, r.t.; (c) CH$_3$OH, r.t.

Figure 21:
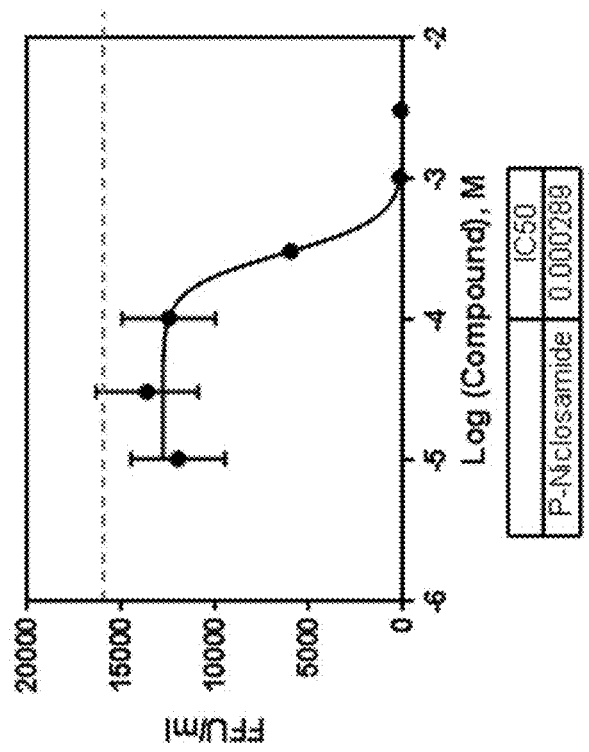

FIG. 21. Antiviral activity of p-niclosamide against ZIKV infection. Infectious PRVABC59-ZIKV production from human glioblastoma SNB-19 cells treated with increasing concentration of indicated compound. 24-hours post infection, supernatants from SNB-19 cells were titrated onto naïve vero cells plated in a monolayer in 96-well plates for infectious focus-forming unit assay as previously described and focus forming units quantified [47]. P-niclosamide IC50 in SNB-19 cell culture production of ZIKV=0.000289M. IC50's calculated using graphpad PRISM software.

Figure 22:
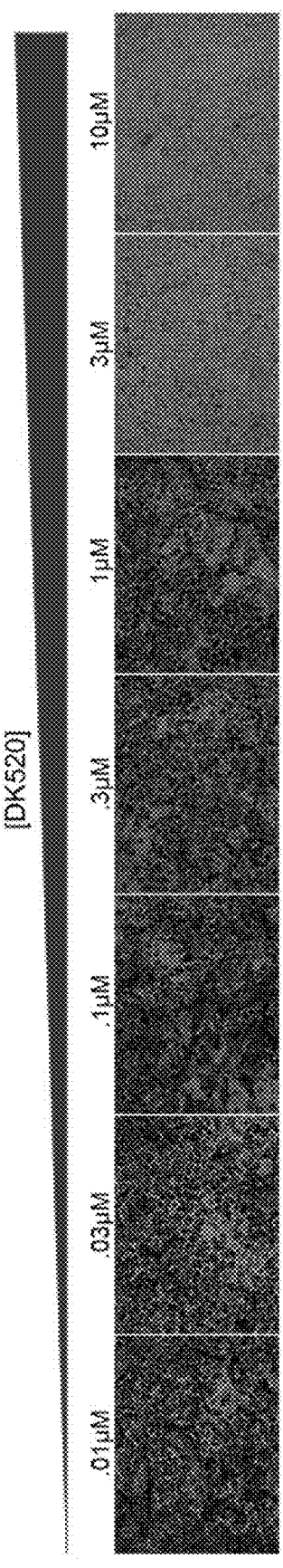

FIG. 22. Antiviral activity of DK-520 against ZIKV infection. Infectious PRVABC59-ZIKV production from human glioblastoma SNB-19 cells treated with increasing concentration of indicated compound. 24-hours post infection, supernatants from SNB-19 cells were titrated onto naïve vero cells plated in a monolayer in 96-well plates and stained for ZIKV-ENV protein and DAB substrate. Shown are phase-contrast images of ZIKV-ENV stained cells (in black). Results indicate IC50 of DK520 against ZIKV infection in human glioblastoma cell culture is <3 µM.

DETAILED DESCRIPTION OF THE INVENTION

The inventors have identified compounds useful for the treatment and prevention of Zika virus (ZIKV) infections and other Flavivirus infections based at least on their ability to inhibit Flavivirus infection in vitro or in vivo, or their ability to suppress Flaviviurs-induced capsase-3 activity (e.g., in one or more host neural cell types).

One aspect of the invention concerns a method for treating or preventing Flavivirus infection in a human or non-human animal subject, the method comprising administering an effective amount of at least one compound to a subject in need thereof, wherein the at least one compound inhibits Flavirus infection or suppresses Flavivirus-induced caspase-3 activity, and wherein the at least one compound comprises:

(a) a niclosamide compound, or (b) an emricasan compound, or (c) a cyclin-dependent kinase (CDK) inhibitor, or (d) a proteasome inhibitor, or (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

In some embodiments, a combination of two or more of the foregoing compounds from (a), (b), (c), (d), or (e) are administered.

In some embodiments, one or more compounds from Tables 7-10 or FIGS. 9-22, or a pharmaceutically acceptable salt thereof, are administered. In some embodiments, a prodrug, metabolite, or derivative of a compound of Tables 7-10, or FIGS. 9-22, is administered to the subject. In some embodiments, the compound is one that reduces virally-induced caspase activation and apoptosis by either directly preventing Zika virus-induced cell death or suppressing Zika replication in a subject.

Another aspect of the invention concerns a method for inhibiting Flavivirus infection in human or non-human animal cells in vitro or in vivo, said method comprising contacting an effective amount of at least one compound to a human or non-human animal cell in vitro or in vivo before or after exposure of the cell to Flavivirus, wherein the at least one compound inhibits Flavirus infection or suppresses Flavivirus-induced caspase-3 activity, and wherein the at least one compound comprises:

(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing. In some embodiments, the cells are contacted with a combination of two or more of the foregoing compounds from (a), (b), (c), (d), or (e). In some embodiments of the method for inhibiting Flavivirus infection in cells, the cell is a neural cell, such as a neural progenitor cell or astrocyte. Contacting of cells in vitro or in vivo with one or more of the compounds of the invention may be carried out before Flavivirus infection (pre-infection) or after Flavivirus infection (post-infection). When carried out in vivo, the one or more compounds are administered to a human or non-human animal subject. Optionally, when carried out in vivo, the method for inhibiting Flavivirus infection in cells may be treat or prevent Flavivirus infection in accordance with the method of treatment herein.

In some embodiments, the cells are contacted with one or more compounds from Tables 7-10, or FIGS. 9-22, or a pharmaceutically acceptable salt thereof. In some embodiments, the cells are contacted with a prodrug, metabolite, or derivative of a compound of Tables 7-10, or FIGS. 9-22, or a pharmaceutically acceptable salt thereof. In some embodiments, the compound is one that reduces virally-induced caspase activation and apoptosis by either directly preventing Zika virus-induced cell death or suppressing Zika replication in a subject.

In some embodiments of the methods, compositions, kits, and packaged dosage formulations of the invention, the Flavivirus infection is Zika virus, West Nile virus, dengue virus (e.g., type 1, 2, 3, or 4), tick-borne encephalitis virus, Japanese encephalitis virus, St. Louis encephalitis virus, or yellow fever virus. Other members of the genus can be found in Kuno G et al., *Journal of Virology*, 1998, "Phylogeny of the Genus Flavivirus," 72(1):73-83, which is incorporated herein by reference. In some embodiments, the Flavivirus is Zika virus. The Zika virus may be any origin or lineage (e.g., African, Asian, American, Brazilian). Examples of Zika virus strains include but are not limited to MR766 (1947 Uganda strain), FSS13025 (2010 Cambodian strain), PRVABC59 (2015 Puerto Rican strain), GZ01/2016 (2016 Chinese strain (ex Venezuela)), H/PF/2013 (2013 French Polynesian strain), IBH30656 (1968 Nigerian strain), Paraiba 2015 (2015 Brazilian strain), PLCal_ZV (2013 Canadian strain (ex Thailand)), SMGC-1 (2016 Chinese strain), SPH 2015 (2015 Brazilian strain), and SZ01 (2016 Chinese strain).

In the various methods, compositions, kits and packaged dosage formulations of the invention, the compound or compounds used may comprise:

(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Derivatives of any of the compounds can be synthesized by chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O(+)$, chlorination ($Cl_2$) bromination ($Br_2$), iodination ($I_2$), chlorohydrin formation ($Cl_2/H_2O$), bromohydrin formation ($Br_2/H_2O$), ether formation ($H^+/ROH$), oxymercuration ($Hg(OAc)_2/H_2O$), oxymercuration, ($Hg(OAc)_2/ROH$), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial, reduction ($Na/NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hoffmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $S_N2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+others), protection as silyl ethers, thiol formation ($S_N2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R-X plus catalyst), Friedel Crafts acylation (RCOX plus catalyst), iodination ($I_2$/catalyst), Side chain oxidation ($KMnO_4$), reduction of nitro groups, reduction of aromatic ketones, Side chain bromination, nucleophilic aromatic substitution ($S_NAr$), and aryne formation ($S_NAr$ via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation ($ROH/H^+$), acetal hydrolysis ($H_3O^+$), imine, formation ($RNH_2$), Enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles ($P_2O_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines ($LiAlH_4$), hydrolysis to carboxylic acids. Optionally, potential derivatives of compounds disclosed herein can be tested for caspase activity and/or the ability to inhibit virally-induced apoptosis and/or suppress viral replication using methods disclosed herein (e.g., caspase 3/7 activity assay, ATP cell viability assay) or using other methods known in the art.

The niclosamide compound may be: (a) niclosamide, (b) a niclosamide derivative, (c) a metabolite or prodrug of (a) or (b), or (d) a pharmaceutically acceptable salt of (a), (b), or (c). In some embodiments, the niclosamide or niclosamide derivative has a structure of FIG. 9A, FIG. 9B, FIG. 9C, or FIG. 9D (Formula 1, Formula 2, Formula 3, or Formula 4, respectively).

In some embodiments, the niclosamide or niclosamide derivative has a structure of FIG. 9A (Formula 1):

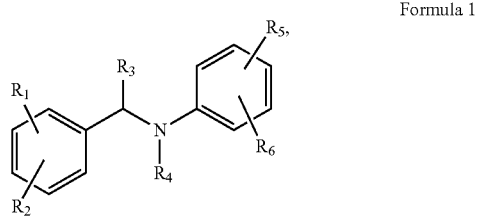

Formula 1 or a pharmaceutically acceptable salt thereof,
where $R_1$, $R_2$, $R_3$, $R_4$, $R_5$, $R_6$ can be independently selected from the group consisting of a H; F; Cl; Br; I; OH; ketone (=O); ($C_{1-6}$)alkyl, such as methyl, ethyl, n-propyl, isopropyl, n-butyl, sec-butyl, isobutyl, tert-butyl; ($C_{2-6}$)alkenyl, such as ethenyl, propenyl, butenyl, where the double bond can be located at any position in the alkenyl carbon chain, including any alkenyl conformational isomers; ($C_{2-6}$)alkynyl, where the triple bond can be located at any position in the alkenyl carbon chain, including any alkynyl conformational isomers; ether [—OR, where R can include ($C_{1-6}$) alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X can include F, Cl, Br, and I]; carbonyl [—COR, where R can include ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; aldehyde (—CHO); ester [—OC(=O)R, —ROC(=O)R', RC(=O)OR', —C(=O)OR', where R and R' can include ($C_{1-14}$)alkyl, such as methyl, ethyl, n-propyl, isopropyl, n-butyl, sec-butyl, isobutyl, tert-butyl; and ($C_{2-14}$) alkenyl, such as ethenyl, propenyl, butenyl, where the double bond can be located at any position in the alkenyl carbon chain, including any alkenyl conformational isomers]; carbonate ester [—OCOOR, where R can include ($C_{1-6}$)alkyl, such as methyl, ethyl, n-propyl, isopropyl, n-butyl, sec-butyl, isobutyl, tert-butyl; and ($C_{1-6}$)alkenyl, such as ethenyl, propenyl, butenyl, where the double bond can be located at any position in the alkenyl carbon chain, including any alkenyl conformational isomers]; carboxyl (—COOH); amide [—CONR'R", where R' and R" can be independently selected from hydrogen; alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, including any alkenyl conformational isomers]; amines [—NR'R", where R' and R" can be independently selected from hydrogen; ($C_{1-6}$) alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R"), where R can include H; ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; borinate [—B(R')(OR"), where R' and R" can be independently selected from hydrogen; ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; phosphino [—PR$_2$, where R can include hydrogen; ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; phosphate [—OP(=O)(OR)$_2$, where R can include H; ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers; phosphono [—RP(=O)(OH), where R can include ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; thiol (—SH); thioalkyl; alkylthio; sulfide [—SR, where R can include ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; disulfide [—SSR, where R can include ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers], sulfonamide; sulfinyl [—S(=O)R, where R can include ($C_{1-6}$) alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers]; sulfino (—SO$_2$H); sulfo (—SO$_3$H); thiocyanate; isothiocyanate; carbonothioyl [—C(=S)R where R can include ($C_{1-6}$)alkyl, such as methyl, ethyl, n-propyl, isopropyl, n-butyl, sec-butyl, isobutyl, tert-butyl; and ($C_{2-6}$)alkenyl, such as ethenyl, propenyl, butenyl, where the double bond can be located at any position in the alkenyl carbon chain, including any alkenyl conformational isomers];

where $R_2$ and $R_4$ can be bonded together to form an $(C_{1-8})$ alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring; and where $R_4$ and $R_6$ can be bonded together to form an $(C_{1-8})$ alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring.

In some embodiments, the niclosamide or niclosamide derivative has the structure of FIG. 9B (Formula 2):

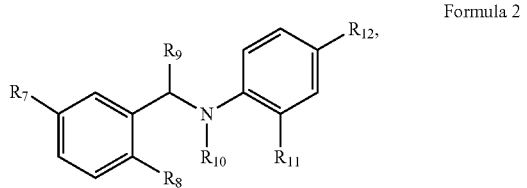

Formula 2 or a pharmaceutically acceptable salt thereof, where $R_7$, $R_8$, $R_9$, $R_{10}$, $R_{11}$, $R_{12}$ can be independently selected from the group consisting of a H; F; Cl; Br; I; OH; ketone (═O); $(C_{1-6})$alkyl, such as methyl, ethyl, n-propyl, isopropyl, n-butyl, sec-butyl, isobutyl, tert-butyl; $(C_{2-6})$alkenyl, such as ethenyl, propenyl, butenyl, where the double bond can be located at any position in the alkenyl carbon chain, including any alkenyl conformational isomers; $(C_{2-6})$alkynyl, where the triple bond can be located at any position in the alkenyl carbon chain, including any alkynyl conformational isomers; ether [—OR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X can include F, Cl, Br, and I]; carbonyl [—COR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; aldehyde (—CHO); ester [—OC(═O)R, —ROC(═O)R', RC(═O)OR', —C(═O)OR', where R and R' can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers]; carbonate ester [—OCOOR, where R can include $(C_{1-6})$alkyl, such as methyl, ethyl, n-propyl, isopropyl, n-butyl, sec-butyl, isobutyl, tert-butyl; and $(C_{1-6})$alkenyl, such as ethenyl, propenyl, butenyl, where the double bond can be located at any position in the alkenyl carbon chain, including any alkenyl conformational isomers]; carboxyl (—COOH); amide [—CONR'R", where R' and R" can be independently selected from hydrogen; alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, including any alkenyl conformational isomers]; amines [—NR'R", where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; cyanate (—OCN); isocynate (—NCO); nitrate (—ONO$_2$); nitrile (—CN); isonitrile (—NC); nitroso (—NO); oxime (—CH═NOH); borono —B(OH)$_2$; borono and boronate [—B(OR')(R"), where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; borinate [—B(R')(OR"), where R' and R" can be independently selected from hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosophino [—PR$_2$, where R can include hydrogen; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; phosphate [—OP(═O)(OR)$_2$, where R can include H; $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers; phosphono [—RP(═O)(OH), where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; thiol (—SH); thioalkyl; alkylthio; sulfide [—SR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; disulfide [—SSR, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers], sulfonamide; sulfinyl [—S(═O)R, where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers]; sulfino (—SO$_2$H); sulfo (—SO$_3$H); thiocyanate; isothiocyanate; carbonothioyl [—C(═S)R where R can include $(C_{1-6})$alkyl, such as methyl, ethyl, n-propyl, isopropyl, n-butyl, sec-butyl, isobutyl, tert-butyl; and $(C_{2-6})$alkenyl, such as ethenyl, propenyl, butenyl, where the double bond can be located at any position in the alkenyl carbon chain, including any alkenyl conformational isomers];

where $R_7$ and $R_{10}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring;

where $R_8$ and $R_{10}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring; and where $R_{10}$ and $R_{11}$ can be bonded together to form an $(C_{1-8})$alkane ring and/or $(C_{2-8})$alkene ring, such as a five-membered ring or a six-membered ring; and where $R_4$ and $R_5$ can be bonded together to form an $(C_{1-8})$alkane ring and/or $(C_{2-8})$alkene ring, such as a five-membered ring or a six-membered ring.

In some embodiments, the niclosamide or niclosamide derivative has the structure of FIG. 9C (Formula 3):

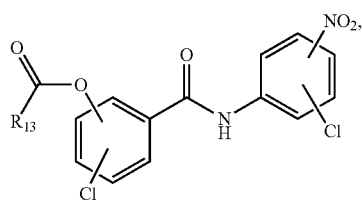

Formula 3 or a pharmaceutically acceptable salt thereof, where $R_{13}$ can include $(C_{1-14})$alkyl, such as methyl, ethyl, n-propyl, isopropyl, n-butyl, sec-butyl, isobutyl, tert-butyl; and $(C_{2-14})$alkenyl, such as ethenyl, propenyl, butenyl, where the double bond can be located at any position in the alkenyl carbon chain, including any alkenyl conformational isomers.

In some embodiments, the niclosamide or niclosamide derivative has the structure of FIG. 9D (Formula 4):

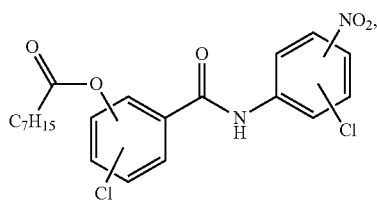

Formula 4 or a pharmaceutically acceptable salt thereof.

In some embodiments, the compound is a derivative of niclosamide such as p-niclosamide [48], which is incorporated herein by reference in its entirety, or an acyl derivative of niclosamide, such as DK-520 [49], which is incorporated herein by reference in its entirety, or a pharmaceutically acceptable salt thereof.

The emricasan compound may comprise: (a) emricasan, (b) an emricasan derivative, (c) a metabolite or prodrug of (a) or (b), or (d) a pharmaceutically acceptable salt of (a), (b), or (c). In some embodiments, the emricasan or emricasan derivative has the structure of FIG. 10 (Formula 5):

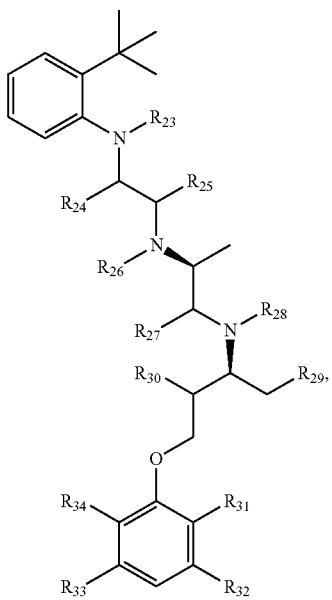

Formula 5 or a pharmaceutically acceptable salt thereof, where $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$, can be independently selected from the group consisting of: H; F; Cl; Br; I; OH; ketone (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; phosophino [—$PR_2$, where R can include hydrogen, methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; sulfino (—$SO_2H$); sulfo (—$SO_3H$); thiocyanate; isothiocyanate; carbonothioyl [—C(=S)R where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers;

where $R_{23}$ and $R_{24}$ can be bonded together to form an ($C_{2-8}$)alkane ring and/or ($C_{2-8}$)alkene ring, such as a five-membered ring or a six-membered ring; where $R_{23}$ and $R_{25}$ can be bonded together to form an ($C_{2-8}$)alkane ring and/or ($C_{2-8}$)alkene ring, such as a five-membered ring or a six-membered ring, where $R_{24}$ and $R_{26}$ can be bonded together to form an ($C_{2-8}$)alkane ring and/or ($C_{2-8}$)alkene ring, such as a five-membered ring or a six-membered ring; where $R_{27}$ and $R_{30}$ can be bonded together to form an ($C_{2-8}$)alkane ring and/or ($C_{2-8}$)alkene ring, such as a five-membered ring or a six-membered ring; where $R_{28}$ and $R_{29}$ can be bonded together to form an ($C_{2-8}$)alkane ring and/or ($C_{2-8}$)alkene ring, such as a five-membered ring or a six-membered ring; where $R_{27}$ and $R_{30}$ can be bonded together to form an ($C_{2-8}$)alkane ring and/or ($C_{2-8}$)alkene ring, such as a five-membered ring or a six-membered ring; and where $R_{29}$ and $R_{30}$ can be bonded together to form an ($C_{2-8}$)alkane ring and/or ($C_{2-8}$)alkene ring, such as a five-membered ring or a six-membered ring.

The compounds of the invention (e.g., niclosamide compounds; emricasan compounds; CDK inhibitors; proteasome inhibitors; compounds in Tables 7-10 and FIGS. 9-22, or a prodrug, metabolite, or derivative thereof) may be administered to the subject in combinations of two or more. For example, in some embodiments, the at least one compound comprises a combination of the niclosamide compound and the emricasan compound, and the niclosamide compound and the emricasan compound are administered simultaneously, together within the same composition or in separate compositions. In other embodiments, the at least one compound comprises a combination of the niclosamide compound and the emricasan compound, and wherein the niclosamide compound and the emricasan compound are administered consecutively in any order.

Figure 11:
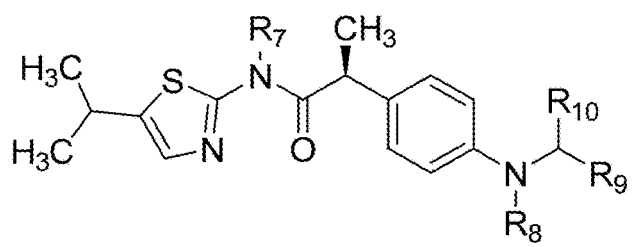
FIG. 11. Formula encompassing the CDK inhibitor PHA-690509 and derivatives of PHA-690509 (Formula 6).

In some embodiments, the at least one compound comprises the CDK inhibitor, and the CDK inhibitor has a structure shown in FIG. 11 (PHA-690509 or a derivative thereof; Formula 6), FIG. 12 (Alvocidib or a derivative thereof; Formula 7), FIG. 13 (PHA-793887 or a derivative thereof; Formula 8), FIG. 14 (Dinaciclib or a derivative thereof; Formula 9), FIG. 15 (Seliciclib or a derivative thereof; Formula 10), or a pharmaceutically acceptable salt of any of the foregoing.

In some embodiments, the CDK inhibitor has the structure shown in FIG. 11 (Formula 6, which encompasses the CDK inhibitor PHA-690509 and derivatives of PHA-690509):

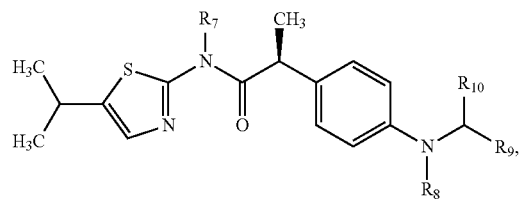

Formula 6 or a pharmaceutically acceptable salt thereof,
where $R_7$, $R_8$, $R_9$, $R_{10}$ can be independently selected from the group consisting of H; F; Cl; Br; I; OH; ketone (=O); ether [—OR, where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R''), where R' and R'' can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; borinate [—B(R')(OR''), where R' and R'' can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; (C$_{1-4}$)alkyl, such as methyl, ethyl, n-propyl, isopropyl, n-butyl, sec-butyl, isobutyl, tert-butyl; and (C$_{2-4}$)alkenyl, such as ethenyl, propenyl, butenyl, where the double bond can be located at any position in the alkenyl carbon chain, and including any alkenyl conformational isomers; and where R$_8$ and R$_9$ can be bonded together to form a (C$_{2-8}$)lactam ring with or without a double carbon-carbon bond.

Figure 12:
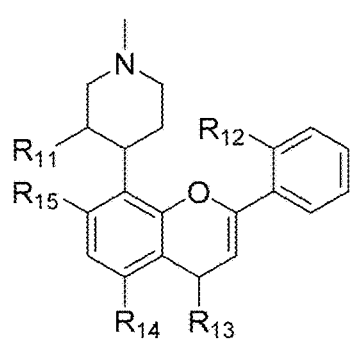
FIG. 12. Formula encompassing the CDK inhibitor Alvocidib and derivatives of Alvocidib (Formula 7).

In some embodiments, the CDK inhibitor has the structure shown in FIG. 12 (Formula 7, encompassing the CDK inhibitor Alvocidib and derivatives of Alvocidib):

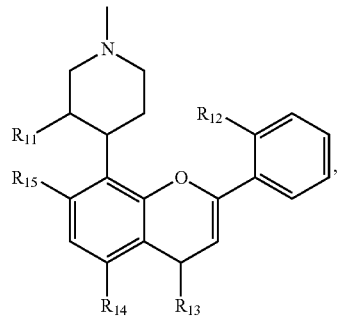

Formula 7 or a pharmaceutically acceptable salt thereof, where R$_{11}$, R$_{12}$, R$_{13}$, R$_{14}$ and R$_{15}$ can be independently selected from a group consisting of H; F; Cl; Br; I; OH; ketone (=O); ether [—OR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; carboxyl (—COOH); amide [—CONR'R'', where R' and R'' can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; amines [—NR'R'', where R' and R'' can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R''), where R' and R'' can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; borinate [—B(R')(OR''), where R' and R'' can be independently selected from hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; (C$_{2-4}$)alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; where $R_{11}$ and $R_{15}$ can be bonded together to form an $(C_{2-8})$alkane ring and/or $(C_{2-8})$ alkene ring, such as a five-membered ring or a six-membered ring; and where $R_{13}$ and $R_{14}$ can be bonded together to form an $(C_{2-8})$alkane ring and/or $(C_{2-8})$alkene ring, such as a five-membered ring or a six-membered ring.

Figure 13:
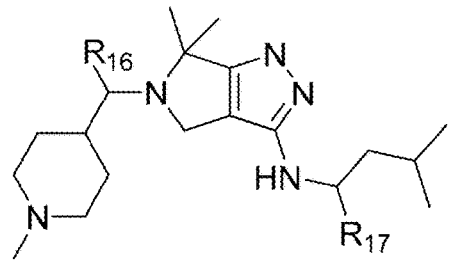
FIG. 13. Formula encompassing the CDK inhibitor PHA-793887 and derivatives of PHA-793887 (Formula 8).

In some embodiments, the CDK inhibitor has the structure shown in FIG. 13 (Formula 8, which encompasses the CDK inhibitor PHA-793887 and derivatives of PHA-793887:

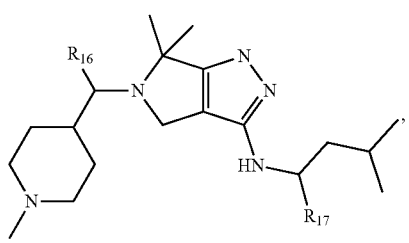

Formula 8 or a pharmaceutically acceptable salt thereof,
where $R_{16}$ and $R_{17}$ can be independently selected from a group consisting of H; F; Cl; Br; I; OH; ketone (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; and $(C_{2-4})$alkenyl, such as ethenyl, propenyl, butenyl, where the double bond can be located at any position in the alkenyl carbon chain, and including any alkenyl conformational isomers.

Figure 14:
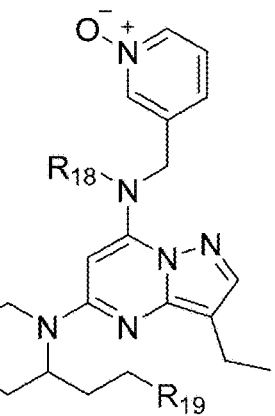
FIG. 14. Formula encompassing the CDK inhibitor Dinaciclib and derivatives of Dinaciclib (Formula 9).

In some embodiments, the CDK inhibitor has the structure shown in FIG. 14 (Formula 9, which encompasses the CDK inhibitor Dinaciclib and derivatives of Dinaciclib):

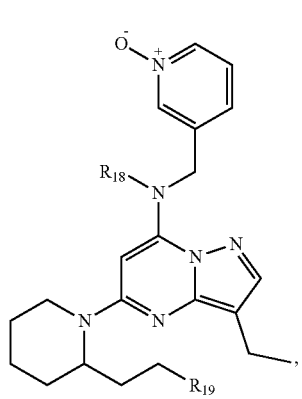

Formula 9 or a pharmaceutically acceptable salt thereof, where $R_{18}$ and $R_{19}$ can be selected from the group consisting of H; F; Cl; Br; I; OH; ketone (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—ONO$_2$); nitrile (—CN); isonitrile (—NC); nitroso (—NO); oxime (—CH=NOH); borono —B(OH)$_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—PR$_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)$_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—SO$_2$H); sulfo (—SO$_3$H); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; and $(C_{2-4})$alkenyl, such as ethenyl, propenyl, butenyl, where the double bond can be located at any position in the alkenyl carbon chain, and including any alkenyl conformational isomers.

Figure 15:
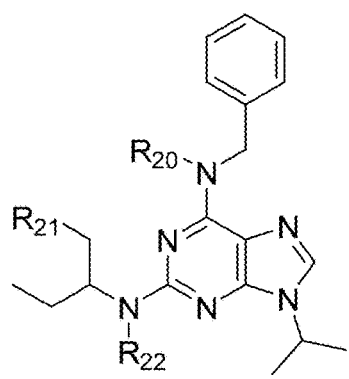
FIG. 15. Formula encompassing the CDK inhibitor Selicicib and derivatives of Selicicib (Formula 10).

In some embodiments, the CDK inhibitor as the structure shown in FIG. 15 (Formula 10, which encompasses the CDK inhibitor Selicicib and derivatives of Selicicib:

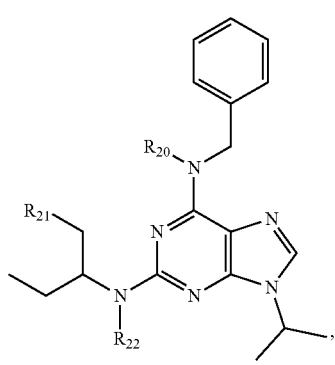

Formula 10 or a pharmaceutically acceptable salt thereof,
where $R_{20}$, $R_{21}$, $R_{22}$ can be selected from the group consisting of H; F; Cl; Br; I; OH; ketone (=O); ether [—OR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; acyl halide (—COX); carbonyl [—COR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; aldehyde (—CHO); carbonate ester [—OCOOR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; carboxyl (—COOH); amide [—CONR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; amines [—NR'R", where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; cyanate (—OCN); isocynate (—NCO); nitrate (—$ONO_2$); nitrile (—CN); isonitrile (—NC); nitroso (—NO); oxime (—CH=NOH); borono —$B(OH)_2$; boronare [—B(OR')(R"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; borinate [—B(R')(OR"), where R' and R" can be independently selected from hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosophino [—$PR_2$, where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphono [—P(=O)(OH)(R), where R can include hydrogen, methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; phosphate (—OP(=O)(OH)_2$; thiol (—SH); sulfide [—SR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; disulfide [—SSR, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers], sulfinyl [—S(=O)R, where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; sulfino (—$SO_2H$); sulfo (—$SO_3H$); thiocyanate; isothiocyanate; carbonothioyl [—C(=S)R where R can include methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers]; $(C_{1-4})$alkyl, such as methyl, ethyl, n-propyl, isopropyl, n-butyl, sec-butyl, isobutyl, tert-butyl; and $(C_{2-4})$alkenyl, such as ethenyl, propenyl, butenyl, where the double bond can be located at any position in the alkenyl carbon chain, and including any alkenyl conformational isomers.

In some embodiments, the at least one compound comprises the CDK inhibitor, and the CDK inhibitor has a structure shown in FIG. 16, or a pharmaceutically acceptable salt thereof.

In some embodiments, the at least one compound comprises a combination of the CDK inhibitor and the emricasan compound, and wherein the CDK inhibitor and the emricasan compound are administered simultaneously, together within the same composition or in separate compositions. In other embodiments, the at least one compound comprises a combination of the CDK inhibitor and an emricasan compound, and wherein the CDK inhibitor and the emricasan compound are administered consecutively in any order.

In some embodiments, the at least one compound is selected from among SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Dinaciclib, Vincristine, Idarubicin, Thapsigargin, Lexibulin, Ixazomib, Cephalomannine, Mitoxantrone, MLN-2238, Demecolcine, RGB-286147, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, 7-Hydroxystaurosporine, CGP-60474, Floxuridine, Go-6976, OSU-03012, a prodrug of any of the foregoing, a metabolite of any of the foregoing, a derivative of any of the foregoing, or a pharmaceutically acceptable salt of any of the foregoing.

The methods of the invention may be used to treat an existing Flavivirus infection in a subject, or the methods of the invention may be used prophylactically to prevent a Flavivirus infection in a subject. As used herein, in this context, the term "prevent" or "prevention" is inclusive of delaying the onset of infection and/or one or more symptoms of infection, and precluding the occurrence or reoccurrence of infection and/or one or more symptoms of infection. Thus, in some embodiments, the subject has the Flavivirus infection at the time the at least one compound is administered, and the at least one compound is administered as therapy.

In some embodiments, the methods further comprise, prior to administering the at least one compound to the subject, identifying the subject as having the Flavivirus infection. The identifying step may comprise assaying a biological sample (e.g., blood, saliva, or urine) obtained from the subject for the presence of Flavivirus nucleic acids or Flavivirus proteins (e.g., Zika virus nucleic acids or Zika virus proteins). In some embodiments, assaying includes the use of reverse transcriptase-polymerase chain reaction (RT-PCR), immunological assay (e.g., ELISA), or Plaque-reduction neutralization testing (PRNT).

One or more compounds of the invention (also referred to herein as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the subject. In some embodiments, at least one compound of the invention is administered orally, nasally, rectally, parenterally, subcutaneously, intramuscularly, or intravascularly (e.g., intravenously).

In some embodiments, the methods further comprise administering an additional agent for treating or preventing Flavivirus infection, or a symptom thereof, in the same formulation as the at least one compound, or in a separate formulation before, during, or after administration of the at least one compound. The additional agent may be one or more compounds of the invention, or one or more different agents, or both.

In some embodiments, at least one compound of the invention is administered to the subject in a composition, wherein the composition comprises the at least one compound and a pharmaceutically acceptable buffer, carrier, or diluent.

Another aspect of the invention concerns a composition comprising a combination of two or more of the following:
(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Another aspect of the invention concerns a composition comprising:
(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing; and
an additional agent effective for the treatment of one or more symptoms of Flavivirus infection. In some embodiments, the Flavivirus infection is Zika virus infection.

Another aspect of the invention concerns a packaged dosage formulation comprising at least one compound in a pharmaceutically acceptable dosage in one or more packages, packets, or containers, wherein the at least one compound comprises:
(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

In some embodiments, the packaged dosage formulation comprises a combination of two or more of the foregoing compounds from (a), (b), (c), (d), or (e).

Another aspect of the invention concerns a kit comprising, in one or more containers, at least one compound comprising:
 (a) a niclosamide compound, or
 (b) an emricasan compound, or
 (c) a cyclin-dependent kinase (CDK) inhibitor, or
 (d) a proteasome inhibitor, or
 (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

In some embodiments, the kit comprises a combination of two or more of the foregoing compounds from (a), (b), (c), (d), or (e). In some embodiments, the kit further comprises an additional agent effective for the treatment or prevention of Flavivirus virus infection. In some embodiments, the kit further comprises an additional agent effective for the treatment of one or more symptoms of Flavivirus infection.

As with the methods of the invention, in the compositions, packaged dosage formulations, and kits of the invention, the niclosamide compound may be: (a) niclosamide, (b) a niclosamide derivative, (c) a metabolite or prodrug of (a) or (b), or (d) a pharmaceutically acceptable salt of (a), (b), or (c); the emricasan compound may comprise: (a) emricasan, (b) an emricasan derivative, (c) a metabolite or prodrug of (a) or (b), or (d) a pharmaceutically acceptable salt of (a), (b), or (c); the CDK inhibitor may comprise, for example: a compound having the structure shown in FIG. 11 (PHA-690509 or a derivative thereof), FIG. 12 (Alvocidib or a derivative thereof), FIG. 13 (PHA-793887 or a derivative thereof), FIG. 14 (Dinaciclib or a derivative thereof), FIG. 15 (Seliciclib or a derivative thereof), or a pharmaceutically acceptable salt of any of the foregoing, or a compound having a structure shown in FIG. 16, or a pharmaceutically acceptable salt thereof; and a proteasome inhibitor may comprise, for example, the proteasome inhibitors in FIGS. 19A to 19E-2.

Various techniques may be used to increase bioavailability of the compounds of the invention (e.g., compounds of in Tables 7-10, and FIGS. 9-22, niclosamide compounds, emricasan compounds, CDK inhibitors, and protease inhibitors). For example, prodrugs of compounds can be prepared. Prodrugs employ various physical and chemical modifications to improve features of the active drug, and in some embodiments may be viewed as pharmacologically inactive prodrug functional groups that undergo a chemical transformation or enzymatic cleavage to liberate the active parent drug and produce the desired effect in the body. Utilizing a prodrug approach can yield benefits such as enhanced solubility, improved selective targeting of drugs to anatomical sites, protection from rapid metabolism and elimination, reduction toxic effects of an active drug on other parts of the body, and enhanced patient compliance.

Non-limiting examples of techniques useful for enhancing the bioavailability of BCS Class II drugs include use of co-solvents, hydrotropy, micronization, change in dielectric constant of solvent, amorphous forms, chemical modification of the drug, use of surfactants, inclusion complex, alteration of pH of solvent, use of hydrates or solvates, use of soluble prodrugs, application of ultrasonic waves, functional polymer technology, controlled precipitation technology, evaporative precipitation in aqueous solution, use of precipitation inhibitors, solvent deposition, precipitation, selective adsorption on insoluble carriers, size reduction technologies, lipid based delivery systems, micellar technologies, porous micro particle technology, solid dispersion technique, and various types of solid dispersion systems.

For example, a method for synthesizing a phosphate prodrug of niclosamide (p-niclosamide) with improved water solubility is described in Pan J-X et al., "Niclosamide, an antihelminthic agent, demonstrates antitumor activity by blocking multiple signaling pathways of cancer stem cells," *Chin J Cancer,* 2012, 31(4):178-184, which is incorporated by reference in its entirety (see, for example, Scheme 1 at page 183). This method can be used to prepare pro-drugs of niclosamide compounds and other compounds of the invention, such as compounds in Table 7 and FIG. 16.

Other methods for enhancement of bioavailability (e.g., by enhancement of solubility) are described in Reddy M S et al., "Solubility enhancement of fenofibrate, a BCS class II drug, by self emulsifying drug delivery systems," *International Research Journal of Pharmacy,* 2011, 2(11):173-177; Khamkar G S, "Self micro emulsifying drug delivery system (SMEED) o/w microemulsion for BCS Class II drugs: an approach to enhance oral bioavailability," *International Journal of Pharmacy and Pharmaceutical Sciences,* 2011, 3(3):1-3; Elgart A et al., "Improved oral bioavailability of BCS class 2 compounds by self nano-emulsifying drug delivery systems (SNEDDS): the underlying mechanisms for amiodarone and talinolol", *Pharm Res.*, 2013 December; 30(12):3029-44; Singh N. et al. "Techniques for bioavailability enhancement of BCS class II drugs: a review," *International Journal of Pharmaceutical and Chemical Science*, 2013, 2(2): 1092-1101; Elkihel L et al., "Synthesis and orally macrofilaricidal evaluation of niclosamide lymphotropic prodrugs," *Arzneimittelforschung*, 1994, 44(11): 1259-64; and Kansara H. et al., "Techniques used to enhance bioavailability of BCS class II drugs: a review," *Int. J. Drug Dev. & Res.*, 2015, 7(1):82-93, which are each incorporated herein by reference in its entirety.

International Patent Publication WO 2016/004166 (Wang G et al.), which is incorporated herein by reference in its entirety, describes boron-based prodrugs of phenol- or aromatic hydroxyl group-containing therapeutic molecules, including niclosamide (Table 1, page 15). The boron-prodrug platform can be utilized to make prodrugs of compounds disclosed herein.

International Patent Publication WO 2009/143297 (Naweed Muhammad et al.), which is incorporated herein by reference in its entirety, describes carbonate prodrugs which comprise a carbonic phosphoric anhydride prodrug moiety attached to the hydroxyl or carboxyl group of a parent drug moiety.

Chemical reactions, reactants, and reagents that may be utilized to enhance solubility and make prodrugs of compounds are described in *March's Advanced Organic Chemistry*, 7$^{th}$ edition, 2013, Michael B. Smith, which is incorporated herein by reference in its entirety.

Compounds, and compositions comprising them, useful in the methods of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of at least one compound of the invention is combined with a suitable carrier or diluent in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the compounds of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide or polynucleotide based on the weight of the total composition including carrier or diluent.

The compounds of the subject invention can also be administered utilizing liposome technology, slow release capsules, implantable pumps, and biodegradable containers. These delivery methods can, advantageously, provide a uniform dosage over an extended period of time.

The compounds of the invention can also be modified by the addition of chemical groups, such as PEG (polyethylene glycol). PEGylated compounds can exhibit extended half-lives in vivo in comparison to compounds that are not PEGylated when administered in vivo. Compounds can also be modified to improve cell membrane permeability. In one embodiment, cell membrane permeability can be improved by attaching a lipophilic moiety, such as a steroid, to the compound. In another embodiment, compounds of the invention can be coupled to a cell-penetrating peptide (CPP). CPPs are typically short peptides that are highly cationic and typically include several arginine and/or lysine amino acids. CPPs can be classified as hydrophilic, amphiphilic, or periodic sequence.

The subject invention also concerns a packaged dosage formulation comprising in one or more containers at least compound, and/or composition of the subject invention formulated in a pharmaceutically acceptable dosage. The package can contain discrete quantities of the dosage formulation, such as tablet, capsules, lozenge, and powders. The quantity of compound in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

Optionally, the methods include, prior to administration of at least one compound of the invention, or re-administration of at least one compound of the invention, determining whether the subject has a Flavivirus infection (e.g., a Zika virus infection) or one or more symptoms consistent with a Flavivirus infection. In the case of Zika virus, during the first week after onset of symptoms, viral RNA can often be identified in serum; thus, Zika virus disease can be diagnosed by performing reverse transcriptase-polymerase chain reaction (RT-PCR) on serum. Urine and saliva samples may also be used for detection of Zika virus (Gourinat A-C et al. (2015) *Emerg Infect Dis*, vol. 21, no. 1, pp. 84-86; and Musso D et al. (2015) *J Clin Virol*, vol. 68, pp. 53-55).

Virus-specific IgM and neutralizing antibodies typically develop toward the end of the first week of illness; cross-reaction with related flaviviruses (e.g., dengue and yellow fever viruses) is common and may be difficult to discern. Plaque-reduction neutralization testing (PRNT) can be performed to measure virus-specific neutralizing antibodies and discriminate between cross-reacting antibodies in primary flavivirus infections.

In the case of Zika virus, some infected individuals will not know they have the disease because they will not have symptoms. The most common symptoms of Zika virus infection are fever, maculo-papular rash (often spreading from face to body), joint pain, retro-orbital pain, or conjunctivitis (red eyes). Other common symptoms include general non-specific such as myalgia, asthenia, and headache. The incubation period (the time from exposure to symptoms) for Zika virus disease is not known, but is likely to be a few days to a week. The illness is usually mild with symptoms lasting for several days to a week after being bitten by an infected mosquito. The Zika virus usually remains in the blood of an infected person for approximately a week but it can be found longer in some individuals.

Treatment methods optionally include steps of advising that the subject get plenty of rest and drink fluids for hydration and administration of agents that alleviate symptoms of Flavivirus infection (e.g., Zika virus infection), such as those that reduce fever and pain (e.g., acetaminophen and/or paracetamol). The methods may include administration of the fluids to the subject for hydration.

The subject may be any age or gender. In some embodiments, the subject is male. In some embodiments, the subject is female. In some embodiments, the subject is a post-pubescent female. In some embodiments, the subject is a post-pubescent, pre-menopausal female. In some embodiments, the subject is a non-pregnant female. In some embodiments, the subject is a pregnant female. In some embodiments, the subject has Guillain-Barré syndrome or another condition that is associated with ZIKV infection.

The invention further provides kits, including at least one compound of the invention (e.g., compound of Tables 7-10, or FIGS. 9-22, or prodrug, or metabolite, or derivative or pharmaceutically acceptable salt of a compound of Tables 7-10 or FIGS. 9-22; a niclosamide compound; emricasan compound; CDK inhibitor; proteasome inhibitor, or a combination of two or more of the foregoing) and pharmaceutical formulations, packaged into suitable packaging material, optionally in combination with instructions for using the kit components, e.g., instructions for performing a method of the invention. In one embodiment, a kit includes an amount of at least one compound of the invention, and instructions for administering at least one compound of the invention to a subject in need of treatment on a label or packaging insert. In further embodiments, a kit includes an article of manufacture, for delivering at least one compound of the invention into a subject locally, regionally or systemically, for example.

As used herein, the term "packaging material" refers to a physical structure housing the components of the kit. The packaging material can maintain the components in a sterile state, and can be made of material commonly used for such purposes (e.g., paper, corrugated fiber, glass, plastic, foil, ampules, etc.). The label or packaging insert can include appropriate printed and/or digital instructions, for example, for practicing a method of the invention, e.g., treating a Flavivirus infection (e.g., Zika virus infection), an assay for identifying a subject having a Flavivirus infection (e.g., Zika virus infection), etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a Flavivirus infection (e.g., Zika virus infection). Instructions may additionally include indications of a satisfactory clinical endpoint or any adverse symptoms that may occur, storage information, expiration date, or any information required by regulatory agencies such as the Food and Drug Administration or European Medicines Agency for use in a human subject.

The instructions may be digital or on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing at least one compound of the invention. The kit can also include components for assaying for the presence of Zika virus or other Flavivirus, e.g., an antibody or antibody fragment specific for a Zika virus or other Flavivirus antigen, one or more primers specific for Zika virus or other Flavivirus nucleic acids, a control sample or a standard. Each component of the kit can be enclosed within an individual container or in a mixture and all of the various containers can be within single or multiple packages.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compounds for treating or preventing Zika virus or other Flavivirus infection. Non-limiting examples of such materials include, but not limited to, buffers, diluents, carrier, package, container, vial and/or tube labels listing contents and/or instructions for use, and package inserts with instructions for use.

A label can be on or associated with a container containing a compound of the invention. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the compound(s) of the invention can be presented in a pack or dispenser device which can contain one or more unit dosage forms containing a compound disclosed herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Another aspect of the invention concerns an in vitro screening method to identify compounds as potential treatments for Flavivirus infection (e.g., Zika virus infection), as described herein. The screening method comprises determining the presence or absence of caspase activity and determining whether the compounds reduce virally-induced apoptosis and/or suppress viral replication.

EXEMPLIFIED EMBODIMENTS

Examples of claimed embodiments of the invention include, but are not limited to:

Embodiment 1

A method for treating or preventing Flavivirus infection in a human or non-human animal subject, said method comprising administering an effective amount of at least one compound to a subject in need thereof, wherein the at least one compound inhibits Flavirus infection or suppresses Flavivirus-induced caspase-3 activity, and wherein the at least one compound comprises:
  (a) a niclosamide compound, or
  (b) an emricasan compound, or
  (c) a cyclin-dependent kinase (CDK) inhibitor, or
  (d) a proteasome inhibitor, or
  (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Embodiment 2

The method of embodiment 1, wherein the at least one compound comprises a combination of two or more of the compounds.

Embodiment 3

The method of embodiment 1 or 2, wherein the Flavivirus infection is Zika virus infection.

Embodiment 4

The method of any one of embodiments 1 to 3, wherein the at least one compound comprises a compound in Table 7, or a prodrug, metabolite, or derivative thereof, or a pharmaceutically acceptable salt of any of the foregoing.

Embodiment 5

The method of any one of embodiments 1 to 4, wherein the at least one compound comprises the niclosamide compound, and the niclosamide compound comprises:
  (a) niclosamide,
  (b) a niclosamide derivative,
  (c) a prodrug or metabolite of (a) or (b), or
  (d) a pharmaceutically acceptable salt of (a), (b), or (c).

Embodiment 6

The method of embodiment 5, wherein the niclosamide or niclosamide derivative has the structure of Formula 1:

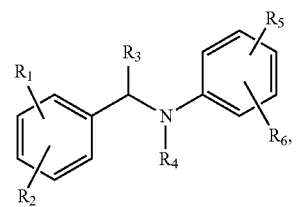

Formula 1 or a pharmaceutically acceptable salt thereof,
  wherein $R_1$, $R_2$, $R_3$, $R_4$, $R_5$, $R_6$ are independently selected from the group consisting of a H; F; Cl; Br; I; OH; ketone (=O); $(C_{1-6})$alkyl; $(C_{2-6})$alkenyl; $(C_{2-6})$alkynyl; ether [—OR, where R can include $(C_{1-6})$alkyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X is selected from F, Cl, Br, and I]; carbonyl [—COR, where R selected from $(C_{1-6})$alkyl; and $(C_{2-6})$alkenyl]; aldehyde (—CHO); ester [—OC(=O)R, —ROC(=O)R', RC(=O)OR', —C(=O)OR', where R and R' is selected from $(C_{1-14})$alkyland $(C_{2-14})$alkenyl; carbonate ester [—OCOOR, where R is selected from $(C_{1-6})$alkyland $(C_{1-6})$alkenyl; carboxyl (—COOH); amide [—CONR'R", where R' and R" is selected from hydrogen; alkyl, such as methyl, ethyl, n-propyl, isopropyl, n-butyl, sec-butyl, isobutyl, tert-butyl; $(C_{2-4})$alkenyl; amines [—NR'R", where R' and R" is selected from hydrogen; $(C_{1-6})$alkyland $(C_{2-6})$alkenyl; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R"), where R is selected from H; $(C_{1-6})$alkyl; and $(C_{2-6})$alkenyl; borinate [—B(R')(OR"), where R' and R" is selected from H; $(C_{1-6})$alkyl and $(C_{2-6})$alkenyl; phosophino [—PR$_2$, where R is selected from H; $(C_{1-6})$alkyl; and $(C_{2-6})$alkenyl; phosphate [—OP(=O)(OR)$_2$, where R is selected from H; $(C_{1-6})$alkyl; and $(C_{2-6})$alkenyl; phosphono [—RP(=O)(OH), where R is selected from $(C_{1-6})$alkyl and $(C_{2-6})$alkenyl; thiol (—SH); thioalkyl; alkylthio; sulfide [—SR, where R is selected from $(C_{1-6})$alkyland $(C_{2-6})$alkenyl; disulfide [—SSR, where R is selected from $(C_{1-6})$ alkyland (C$_{2-6}$)alkenyl, sulfonamide; sulfinyl [—S(=O)R, where R is selected from (C$_{1-6}$)alkyland (C$_{2-6}$)alkenyl; sulfino (—SO$_2$H); sulfo (—SO$_3$H); thiocyanate; isothiocyanate; carbonothioyl [—C(=S)R where R is selected from (C$_{1-6}$)alkyland (C$_{2-6}$)alkenyl;

wherein R$_2$ and R$_4$ can be bonded together to form an (C$_{1-8}$)alkane ring and/or (C$_{2-8}$)alkene ring; wherein R$_4$ and R$_5$ can be bonded together to form an (C$_{1-8}$)alkane ring and/or (C$_{2-8}$)alkene ring;

wherein R$_4$ and R$_6$ can be bonded together to form an (C$_{1-8}$)alkane ring and/or (C$_{2-8}$)alkene ring; and wherein R$_4$ and R$_5$ can be bonded together to form an (C$_{1-8}$)alkane ring and/or (C$_{2-8}$)alkene ring.

Embodiment 7

The method of embodiment 5, wherein the niclosamide or niclosamide derivative has the structure of Formula 2:

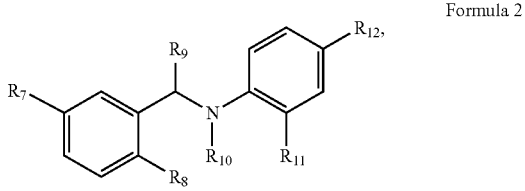

Formula 2 or a pharmaceutically acceptable salt thereof, where R$_7$, R$_8$, R$_9$, R$_{10}$, R$_{11}$, R$_{12}$ are independently selected from the group consisting of a H; F; Cl; Br; I; OH; ketone (=O); (C$_{1-6}$)alkyl; (C$_{2-6}$)alkenyl; (C$_{2-6}$)alkynyl; ether [—OR, where R can include (C$_{1-6}$)alkyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X is selected from F, Cl, Br, and I]; carbonyl [—COR, where R selected from (C$_{1-6}$)alkyl; and (C$_{2-6}$)alkenyl]; aldehyde (—CHO); ester [—OC(=O)R, —ROC(=O)R', RC(=O)OR', —C(=O)OR', where R and R' is selected from (C$_{1-14}$)alkyland (C$_{2-14}$)alkenyl; carbonate ester [—OCOOR, where R is selected from (C$_{1-6}$)alkyland (C$_{1-6}$)alkenyl; carboxyl (—COOH); amide [—CONR'R", where R' and R" is selected from hydrogen; alkyl, such as methyl, ethyl, n-propyl, isopropyl, n-butyl, sec-butyl, isobutyl, tert-butyl; (C$_{2-4}$)alkenyl; amines [—NR'R", where R' and R" is selected from hydrogen; (C$_{1-6}$)alkyland (C$_{2-6}$)alkenyl; cyanate (—OCN); isocynate (—NCO); nitrate (—ONO$_2$); nitrile (—CN); isonitrile (—NC); nitroso (—NO); oxime (—CH=NOH); borono —B(OH)$_2$; borono and boronate [—B(OR')(R"), where R is selected from H; (C$_{1-6}$)alkyl; and (C$_{2-6}$)alkenyl; borinate [—B(R')(OR"), where R' and R" is selected from H; (C$_{1-6}$)alkyl and (C$_{2-6}$)alkenyl; phosophino [—PR$_2$, where R is selected from H; (C$_{1-6}$)alkyl; and (C$_{2-6}$)alkenyl; phosphate [—OP(=O)(OR)$_2$, where R is selected from H; (C$_{1-6}$)alkyl; and (C$_{2-6}$)alkenyl; phosphono [—RP(=O)(OH), where R is selected from (C$_{1-6}$)alkyl and (C$_{2-6}$)alkenyl; thiol (—SH); thioalkyl; alkylthio; sulfide [—SR, where R is selected from (C$_{1-6}$)alkyland (C$_{2-6}$)alkenyl; disulfide [—SSR, where R is selected from (C$_{1-6}$)

alkyland (C$_{2-6}$)alkenyl, sulfonamide; sulfinyl [—S(=O)R, where R is selected from (C$_{1-6}$)alkyland (C$_{2-6}$)alkenyl; sulfino (—SO$_2$H); sulfo (—SO$_3$H); thiocyanate; isothiocyanate; carbonothioyl [—C(=S)R where R is selected from (C$_{1-6}$)alkyland (C$_{2-6}$)alkenyl;

wherein R$_7$ and R$_{10}$ can be bonded together to form an (C$_{1-8}$)alkane ring and/or (C$_{2-8}$)alkene ring; and wherein R$_4$ and R$_5$ can be bonded together to form an (C$_{1-8}$)alkane ring and/or (C$_{2-8}$)alkene ring;

wherein R$_8$ and R$_{10}$ can be bonded together to form an (C$_{1-8}$)alkane ring and/or (C$_{2-8}$)alkene ring; wherein R$_4$ and R$_5$ can be bonded together to form an (C$_{1-8}$)alkane ring and/or (C$_{2-8}$)alkene ring;

wherein R$_{10}$ and R$_{11}$ can be bonded together to form an (C$_{1-8}$)alkane ring and/or (C$_{2-8}$)alkene ring; and wherein R$_4$ and R$_5$ can be bonded together to form an (C$_{1-8}$)alkane ring and/or (C$_{2-8}$)alkene ring.

Embodiment 8

The method of embodiment 5, wherein the niclosamide or niclosamide derivative has the structure of Formula 3:

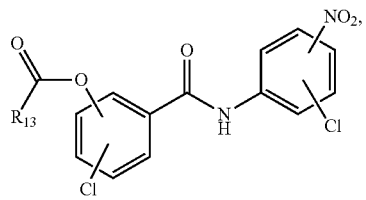

Formula 3 or a pharmaceutically acceptable salt thereof, where R$_{13}$ can include (C$_{1-14}$)alkyl, such as methyl, ethyl, n-propyl, isopropyl, n-butyl, sec-butyl, isobutyl, tert-butyl; and (C$_{2-14}$)alkenyl, such as ethenyl, propenyl, butenyl, where the double bond can be located at any position in the alkenyl carbon chain, including any alkenyl conformational isomers.

Embodiment 9

The method of embodiment 5, wherein the niclosamide or niclosamide derivative has the structure of Formula 4:

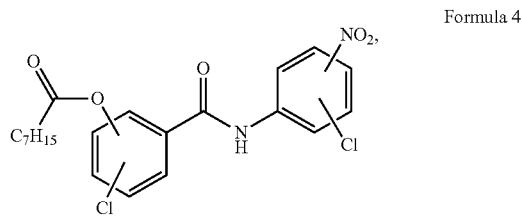

Formula 4 or a pharmaceutically acceptable salt thereof.

Embodiment 10

The method of any one of embodiments 1 to 3, wherein the at least one compound comprises an emricasan compound, and wherein the emricasan compound comprises:
(a) emricasan,
(b) an emricasan derivative, (c) a prodrug or metabolite of (a) or (b), or
(d) a pharmaceutically acceptable salt of (a), (b), or (c).

Embodiment 11

The method of embodiment 10, wherein the emricasan or emricasan derivative has the structure of Formula 5:

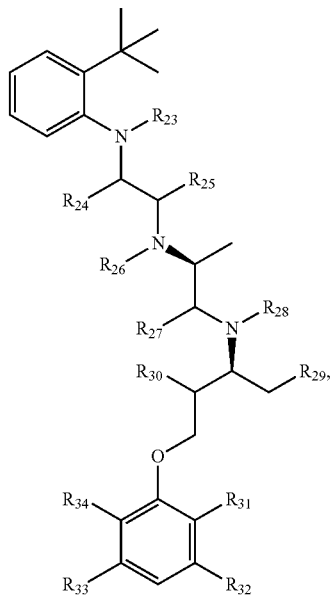

Formula 5 or a pharmaceutically acceptable salt thereof,
where $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$ are independently selected from the group consisting of a H; F; Cl; Br; I; OH; ketone (═O); $(C_{1-6})$alkyl; $(C_{2-6})$alkenyl; $(C_{2-6})$alkynyl; ether [—OR, where R can include $(C_{1-6})$alkyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; alkoxy; alkoxyalkyl; aryloxy; arylalkoxy; acyloxy; nitro; carbamoyl; trifluoromethyl; phenoxy; benzyloxy; alkaryl; arylalkyl; carbamate; amino; alkylamino; arylamino; dialkylamino; alkylarylamino; diarylamino; heteroalkyl; alkyltriphenylphosphonium; heterocyclyl; acyl halide [—COX, where X is selected from F, Cl, Br, and I]; carbonyl [—COR, where R selected from $(C_{1-6})$alkyl; and $(C_{2-6})$alkenyl]; aldehyde (—CHO); ester [—OC(═O)R, —ROC(═O)R', RC(═O)OR', —C(═O)OR', where R and R' is selected from $(C_{1-14})$alkyl and $(C_{2-14})$alkenyl; carbonate ester [—OCOOR, where R is selected from $(C_{1-6})$alkyl and $(C_{1-6})$alkenyl; carboxyl (—COOH); amide [—CONR'R", where R' and R" is selected from hydrogen; alkyl, such as methyl, ethyl, n-propyl, isopropyl, n-butyl, sec-butyl, isobutyl, tert-butyl; $(C_{2-4})$alkenyl; amines [—NR'R", where R' and R" is selected from hydrogen; $(C_{1-6})$alkyl and $(C_{2-6})$alkenyl; cyanate (—OCN); isocyanate (—NCO); nitrate (—ONO$_2$); nitrile (—CN); isonitrile (—NC); nitroso (—NO); oxime (—CH═NOH); borono —B(OH)$_2$; borono and boronate [—B(OR')(R"), where R is selected from H; $(C_{1-6})$alkyl; and $(C_{2-6})$alkenyl; borinate [—B(R')(OR"), where R' and R" is selected from H; $(C_{1-6})$alkyl and $(C_{2-6})$alkenyl; phosophino [—PR$_2$, where R is selected from H; $(C_{1-6})$alkyl and $(C_{2-6})$alkenyl; phosphate [—OP(═O)(OR)$_2$, where R is selected from H; $(C_{1-6})$alkyl; and $(C_{2-6})$alkenyl; phosphono [—RP(═O)(OH), where R is selected from $(C_{1-6})$alkyl and $(C_{2-6})$alkenyl; thiol (—SH); thioalkyl; alkylthio; sulfide [—SR, where R is selected from $(C_{1-6})$alkyl and $(C_{2-6})$alkenyl; disulfide [—SSR, where R is selected from $(C_{1-6})$alkyl and $(C_{2-6})$alkenyl, sulfonamide; sulfinyl [—S(═O)R, where R is selected from $(C_{1-6})$alkyl and $(C_{2-6})$alkenyl; sulfino (—SO$_2$H); sulfo (—SO$_3$H); thiocyanate; isothiocyanate; carbonothioyl [—C(═S)R where R is selected from $(C_{1-6})$alkyl and $(C_{2-6})$alkenyl;

wherein $R_{23}$ and $R_{24}$ can be bonded together to form an $(C_{2-8})$alkane ring and/or $(C_{2-8})$alkene ring; wherein $R_{23}$ and $R_{25}$ can be bonded together to form an $(C_{2-8})$alkane ring and/or $(C_{2-8})$alkene ring; where $R_{24}$ and $R_{26}$ can be bonded together to form an $(C_{2-8})$alkane ring and/or $(C_{2-8})$alkene ring; wherein $R_{27}$ and $R_{30}$ can be bonded together to form an $(C_{2-8})$alkane ring and/or $(C_{2-8})$alkene; wherein $R_{28}$ and $R_{29}$ can be bonded together to form an $(C_{2-8})$alkane ring and/or $(C_{2-8})$alkene ring; and wherein $R_{27}$ and $R_{30}$ can be bonded together to form an $(C_{2-8})$alkane ring and/or $(C_{2-8})$alkene ring, such as a five-membered ring or a six-membered ring; and wherein $R_{29}$ and $R_{30}$ can be bonded together to form an $(C_{2-8})$alkane ring and/or $(C_{2-8})$alkene ring.

Embodiment 12

The method of any one of embodiments 1 to 3, wherein the at least one compound comprises a combination of the niclosamide compound and the emricasan compound, and wherein the niclosamide compound and the emricasan compound are administered simultaneously, together within the same composition or in separate compositions.

Embodiment 13

The method of any one of embodiments 1 to 3, wherein the at least one compound comprises a combination of the niclosamide compound and the emricasan compound, and wherein the niclosamide compound and the emricasan compound are administered consecutively in any order.

Embodiment 14

The method of any one of embodiments 1 to 3, wherein the at least one compound comprises the CDK inhibitor, and the CDK inhibitor has a structure shown in FIG. 11 (PHA-690509 or a derivative thereof), FIG. 12 (Alvocidib or a derivative thereof), FIG. 13 (PHA-793887 or a derivative thereof), FIG. 14 (Dinaciclib or a derivative thereof), FIG. 15 (Seliciclib or a derivative thereof), or a pharmaceutically acceptable salt of any of the foregoing.

Embodiment 15

The method of any one of embodiments 1 to 3, wherein the at least one compound comprises the CDK inhibitor, and the CDK inhibitor has a structure shown in FIG. 16, or a pharmaceutically acceptable salt thereof.

Embodiment 16

The method of any one of embodiments 1 to 3, wherein the at least one compound comprises a CDK inhibitor, and the CDK inhibitor is selected from among Alvocidib, Kenpaullone, Olomoucine, Purvalanol A, Purvalanol B, Seliciclib, NU-6027, Indirubin, Flavopiridol, AT7519, PD-0332991, SNS-032, PHA-793887, PHA-690509, RGB- 286147, BS-194, BS-181, AZD-5438, R-547, Dinaciclib, Milciclib, BMS-265246, 7-Hydroxystaurosporine, CGP-60474, CDK9 inhibitor, NU-6102, Fascaplysin, Cdk4/6 Inhibitor IV, or a prodrug, metabolite, derivative, or pharmaceutically acceptable salt of any of the foregoing.

Embodiment 17

The method of any one of embodiments 1 to 3, wherein the at least one compound comprises a combination of the CDK inhibitor and the emricasan compound, and wherein the CDK inhibitor and the emricasan compound are administered simultaneously, together within the same composition or in separate compositions.

Embodiment 18

The method of any one of embodiments 1 to 3, wherein the at least one compound comprises a combination of the CDK inhibitor and an emricasan compound, and wherein the CDK inhibitor and the emricasan compound are administered consecutively in any order.

Embodiment 19

The method of any one of embodiments 1 to 18, wherein the subject has the Flavivirus infection at the time of said administering, and the at least one compound is administered as therapy.

Embodiment 20

The method of 19, further comprising, prior to said administering, identifying the subject as having the Flavivirus infection.

Embodiment 21

The method of embodiment 20, wherein said identifying comprises assaying a biological sample (e.g., blood, saliva, or urine) obtained from the subject for the presence of Flavivirus nucleic acids or Flavivirus proteins.

Embodiment 22

The method of embodiment 21, wherein said assaying comprises use of reverse transcriptase-polymerase chain reaction (RT-PCR), immunological assay (e.g., ELISA), or Plaque-reduction neutralization testing (PRNT).

Embodiment 23

The method of any one of embodiments 1 to 18, wherein the subject does not have the Flavivirus infection at the time of said administering, and the at least one compound is administered as prophylaxis.

Embodiment 24

The method of any one of embodiments 1 to 23, wherein the at least one compound is administered orally, nasally, rectally, parenterally, subcutaneously, intramuscularly, or intravascularly (e.g., intravenously).

Embodiment 25

The method of any one of embodiments 1 to 24, further comprising administering an additional agent for treating or preventing Flavivirus infection, or a symptom thereof, in the same formulation as at least one compound, or in a separate formulation before, during, or after administration of the at least one compound.

Embodiment 26

The method of any one of embodiments 1 to 25, wherein said administering comprises administering a composition to the subject, wherein the composition comprises the at least one compound and a pharmaceutically acceptable buffer, carrier, or diluent.

Embodiment 27

A method for inhibiting Flavivirus infection in human or non-human animal cells in vitro or in vivo, said method comprising contacting an effective amount of at least one compound to a human or non-human animal cell in vitro or in vivo before or after exposure of the cell to Flavivirus, wherein the at least one compound inhibits Flavirus infection or suppresses Flavivirus-induced caspase-3 activity, and wherein the at least one compound comprises:
  (a) a niclosamide compound, or
  (b) an emricasan compound, or
  (c) a cyclin-dependent kinase (CDK) inhibitor, or
  (d) a proteasome inhibitor, or
  (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxyethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Embodiment 28

The method of embodiment 27, wherein the at least one compound comprises a combination of two or more of the compounds.

Embodiment 29

The method of embodiment 27 or 28, wherein the Flavivirus is Zika virus.

Embodiment 30

A composition comprising a combination of two or more of the following:
(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Embodiment 31

A composition comprising:
(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing, and
an additional agent effective for the treatment of one or more symptoms of Flavivirus infection.

Embodiment 32

The composition of embodiment 31, wherein the Flavivirus infection is Zika virus infection.

Embodiment 33

A packaged dosage formulation comprising at least one compound in a pharmaceutically acceptable dosage in one or more packages, packets, or containers, wherein the at least one compound comprises:
(a) a niclosamide compound, or
(b) an emricasan compound, or
(c) a cyclin-dependent kinase (CDK) inhibitor, or
(d) a proteasome inhibitor, or
(e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Embodiment 34

The packaged dose formulation of embodiment 33, wherein the packaged dose formulation comprises a combination of two or more of the compounds.

Embodiment 35

A kit comprising, in one or more containers, at least one compound comprising:

(a) a niclosamide compound, or (b) an emricasan compound, or (c) a cyclin-dependent kinase (CDK) inhibitor, or (d) a proteasome inhibitor, or (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

Embodiment 36

The kit of embodiment 35, wherein the packaged dose formulation comprises a combination of two or more of the compounds.

Embodiment 37

The kit of embodiment 35 or 36, further comprising an additional agent effective for the treatment or prevention of Flavivirus virus infection.

Embodiment 38

The kit of embodiment 35 or 36, further comprising an additional agent effective for the treatment of one or more symptoms of Flavivirus infection.

Definitions

The terms "compounds of the invention" or "compounds of the present invention" (unless specifically identified otherwise), and grammatical variations thereof, refer to the compounds and classes of compounds disclosed herein, such as the compounds in Tables 7-10, and FIGS. 9-22, or a prodrug, metabolite, or derivative thereof; niclosamide compounds; emricasan compounds; cyclin-dependent kinase (CDK) inhibitors, individually or combinations of two or more, including pharmaceutically acceptable salts of any of the foregoing, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates). For purposes of this invention, solvates and hydrates are generally considered compositions.

For example, in some embodiments, a compound of the invention is:

(a) a niclosamide compound, or (b) an emricasan compound, or (c) a cyclin-dependent kinase (CDK) inhibitor, or (d) a proteasome inhibitor, or (e) a compound selected from among Teriflunomide, Hydroxocobalamin, Ensulizole, Tenonitrozole, Isoliquiritigenin, Nitazoxanide, Febuxostat, Leflunomide, Vidofludimus, SB-366791, Emodin, Diphenyl isophthalate, Benzoylpas, Fenobam, Indobufen, 2-(2H-Benzotriazol-2-yl)-4-methylphenol, Tiaprofenic acid, Flufenamic acid, Vitamin B12, Cinanserin, 5-Nitro-2-(3-phenylpropylamino)benzoic acid, Veliflapon, Thiabendazole, SIB 1893, Anethole trithione, Naringenin, Phenazopyridine, Fanetizole, Terazosin, Diacerein, CAY10505, Hesperetin, Suprofen, Ketorolac tromethamine, Piperine, Pirarubicin, Piraxostat, Albendazole oxide, Tyrphostin AG 494, Genistin, Fenbufen, Apatinib, RITA, BF-170 hydrochloride, OSI-930, Tribromsalan, Pifexole, Formononetin, Ebselen, Tranilast, Benzylparaben, 2-Ethoxylethyl-p-methoxycinnamate, Baicalein, Nemorubicin, Rutaecarpine, 2-Methyl-6-(phenylethynyl)pyridine (MPEP), 5,7-Dihydroxyflavone, Vitamin B12, Pipofezine, Flurbiprofen axetil, 2-Amino-6-nitrobenzothiazole, Malachite green oxalate, Enfenamic acid, Fenaminosulf, AS-252424, Phenserine, Epalrestat, Alizarin, Dalcetrapib, SN-38, Echinomycin, (S)-(+)-Camptothecin, BI-2536, 10-hydroxycamptothecin, Topotecan, Delanzomib, Volasertib, Ispinesib, Paclitaxel, FK-506, Emetine, AVN-944, Digoxin, Vincristine, Idarubicin, Thapsigargin, Lexibulin, Ixazomib, Cephalomannine, Mitoxantrone, MLN-2238, Demecolcine, Vinorelbine, Bardoxolone methyl, Cycloheximide, Actinomycin D, AZD-7762, PF-184, CHIR-124, Cyanein, Triptolide, KX-01, PF-477736, Epirubicin, Mycophenolate (mycophenolic acid), Daunorubicin, PIK-75, Vindesine, Torin-2, Floxuridine, Go-6976, OSU-03012, or a prodrug, metabolite, or derivative of any of the foregoing, or a pharmaceutically acceptable salt of any of the foregoing.

In some embodiments, the compound of the invention is any compound in Tables 7-10, or FIGS. 9-22, or a prodrug, metabolite, or derivative thereof. In some embodiments, the compound of the invention is a pharmaceutically acceptable salt of a compound of Tables 7-10, or FIGS. 9-22, or prodrug, or metabolite, or derivative of a compound of Tables 7-10 or FIGS. 9-22.

In some embodiments, a compound of the invention is a niclosamide compound. In some embodiments, the niclosamide compound is niclosamide, or a pharmaceutically acceptable salt thereof. In some embodiments, the niclosamide compound is a prodrug, metabolite, or derivative of niclosamide. In some embodiments, the niclosamide compound is a compound having a chemical structure of any of FIGS. 9A-D, or a pharmaceutically acceptable salt thereof. In some embodiments, the niclosamide compound is a prodrug of niclosamide or a prodrug of a compound having a chemical structure of any of FIGS. 9A-D. In some embodiments, the compound of the invention is a derivative of niclosamide, such as p-niclosamide or an acyl derivative of niclosamide such as DK-520.

In some embodiments, a compound of the invention is an emricasan compound. In some embodiments, the emricisan compound is emricasan, or a pharmaceutically acceptable salt thereof. In some embodiments, the emricasan compound is a prodrug, metabolite, or derivative of emricasan. In some embodiments, the emricasan compound is a compound having the chemical structure of FIG. 10, or a pharmaceutically acceptable salt thereof. In some embodiments, the emricasan compound is a prodrug of emricasan or a prodrug of a compound having the chemical structure of FIG. 10.

In some embodiments, a compound of the invention is a CDK inhibitor. A CDK inhibitor is an agent, such as a peptide or chemical compound, that inhibits the function of one or more cyclin-dependent kinases. The CDK inhibitor may be a broad CDK inhibitor, targeting multiple types of CDKs or may be a specific CDK inhibitor, targeting a specific type of CDK (see, for example, [50-52], which are incorporated herein by reference in their entirety). In some embodiments, the CDK inhibitor is PHA-690509, Alvocidib, PHA-793887, Dinaciclib, Seliciclib, a compound of FIG. 16, or a pharmaceutically acceptable salt of any of the foregoing. In some embodiments, the CDK inhibitor is a prodrug, metabolite, or derivative of PHA-690509, Alvocidib, PHA-793887, Dinaciclib, Seliciclib, or of a compound of FIG. 16. In some embodiments, the CDK inhibitor is a compound having the chemical structure of FIG. 11, FIG. 12, FIG. 13, FIG. 14, FIG. 15, or a pharmaceutically acceptable salt of any of the foregoing. In some embodiments, the CDK inhibitor is a prodrug of PHA-690509, Alvocidib, PHA-793887, Dinaciclib, Seliciclib, or a prodrug of a compound of FIG. 16. In some embodiments, the CDK inhibitor is a prodrug of a compound having the chemical structure of FIG. 11, FIG. 12, FIG. 13, FIG. 14, or FIG. 15.

In some embodiments, a compound of the invention is a proteasome inhibitor. A proteasome inhibitor is an agent, such as a peptide or chemical compound, that inhibits the action of one or more types of proteasome. (see, for example, [53, 54], which are incorporated herein by reference in their entirety). In some embodiments, the proteasome inhibitor Epirubicin, Ixazoomib, Doxorubicin, Carflizomib, Bortezomib, Delanzomib, Oprozomib, NPI-206, MG-115, Niclosamide, or pharmaceutically acceptable salt of any of the foregoing.

The term "a," "an," "the" and similar terms used in the context of the present invention (especially in the context of the claims) are to be construed to cover both the singular and plural unless otherwise indicated herein or clearly contradicted by the context. Thus, for example, reference "a cell" or "a compound" should be construed to cover both a singular cell or singular compound and a plurality of cells and a plurality of compounds unless indicated otherwise or clearly contradicted by the context.

The term "isolated," when used as a modifier of a composition, means that the compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide).

The present invention includes derivatives of identified compounds, also referred to herein as pharmaceutically active derivatives. "Pharmaceutically active derivative" refers to any compound that upon administration to the subject or cell, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting Flavivirus (e.g., Zika virus) inhibitory activity and/or protective activity against effects of Flavivirus (e.g., Zika virus) that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g., by oxidation, reduction, hydrolysis or the like, each of which is carried out enzymatically. These compounds can be produced from compounds of the invention according to well-known methods. The term "indirectly" also encompasses metabolites of compounds according to the invention. Chemical reactions, reactants, and reagents useful for making derivatives can be found, for example, in *March's Advanced Organic Chemistry*, 7th edition, 2013, Michael B. Smith, which is incorporated herein by reference in its entirety.

The term "metabolite" refers to all molecules derived from any of the compounds according to the invention in a cell or organism, preferably mammal. Pharmaceutically active metabolites of the compounds of the invention may be administered to a subject or contacted with a cell in vitro or in vivo.

The term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastro-intestinal fluids or in the circulation system (Wu, Kuei-Meng, "A New Classification of Prodrugs: Regulatory Perspectives, *Pharmaceuticals*, 2009, 2(3):77-81, which is incorporated by reference herein in its entirety).

Pharmaceutical formulations include "pharmaceutically acceptable" and "physiologically acceptable" carriers, diluents or excipients. As used herein the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions. The phrase "pharmaceutically acceptable" indicates that the substance or composition must be compatible chemically and/or toxicologically, with the other ingredients comprising a formulation, and/or the mammal being treated therewith.

The phrase "effective amount", in the context of a subject, means an amount of at least one compound of the invention that (i) treats or prevents the particular disease, condition, or disorder (e.g., Zika or other Flavivirus infection) in a subject, (ii) attenuates, ameliorates, or eliminates one or more symptoms of the particular disease, condition, or disorder (e.g., Zika or other Flavivirus infection) in a subject, or (iii) prevents or delays the onset of one or more symptoms of the particular disease, condition, or disorder described herein (e.g., Zika or other Flavivirus infection) in a subject.

The phrase "effective amount", in the context of a cell in vitro or in vivo, means an amount of at least one compound of the invention that (i) treats or prevents the particular disease, condition, or disorder (e.g., Zika or other Flavivirus infection) in a cell, (ii) attenuates, ameliorates, or eliminates one or more effects of the particular disease, condition, or disorder (e.g., Zika or other Flavivirus infection) in a cell, or (iii) prevents or delays the onset of one or more effects of the particular disease, condition, or disorder described herein (e.g., Zika or other Flavivirus infection) in a subject.

Niclosamide compounds, proteasome inhibitors, and CDK inhibitors of the invention can inhibit or reduce Zika virus or other Flavivirus replication (e.g., Zika virus infection), and thus represent one class of compounds of the invention. Emricasan compounds of the invention are pan-caspase inhibitors, which inhibit Flavivirus-induced increase in caspase-3 activity, and reduce cell death, and represent another class of compounds of the invention. A combination of one class of compounds (e.g., Niclosamide compound, and/or CDK inhibitor, and/or proteasome inhibitor) with the other class of compounds (e.g., Emricasan compound) can exhibit a synergistic effect in protecting neural cells from Flavivirus-induced (e.g., Zika virus-induced) cell death.

As used herein, a subject is "in need of" a treatment if such human or non-human animal subject would benefit biologically, medically or in quality of life from such treatment (preferably, a human). In some embodiments, the subject has a Flavivirus infection and is in need of therapy. In other embodiments, the subject does not have a Flavivirus infection and is in need of prophylaxis. In some embodiments, the subject in need of prophylaxis is at risk of becoming infected with the Flavivirus. In some embodiments, the subject is at increased risk of becoming infected with the Flavivirus relative to others in the population.

As used herein, the term "inhibit", "inhibition" or "inhibiting" refers to the reduction or suppression of a given condition, symptom, or disorder, or disease (e.g., Zika virus or other Flavivirus infection, or Zika viral or other Flavivirus load or titer), or a significant decrease in the baseline activity of a biological activity or process (inhibits or suppresses Zika or other Flavivirus infection, or inhibits or suppresses Zika or other Flavivirus replication, or inhibits or suppresses Zika-induced or other Flavivirus-induced neural cell death, or inhibits or suppresses infection-induced caspase-3 activity in neural cell types).

As used herein, the terms "subject", "patient", and "individual" refer to a human or non-human animal. Typically, the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. The subject may be any age or gender. For example, in some embodiments, the subject is a female. In some embodiments, the subject is a post-pubescent female or a post-pubescent female. In some embodiments, the subject is a pregnant female.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

As used herein, the term "contacting" in the context of contacting a cell with at least one compound of the invention in vitro or in vivo means bringing at least one compound into contact with the cell, or vice-versa, or any other manner of causing the compound and the cell to come into contact. In those embodiments of the method for inhibiting Flavivirus infection in human or non-human animal cells in vitro or in vivo, when a cell is contacted with a compound in vivo, the compound is administered to a subject, and the administration may occur by any route (e.g., topical, oral, parenteral, subcutaneous, transdermal, transbuccal, intravascular (e.g., intravenous or intra-arterial), intramuscular, subcutaneous, intranasal, and intra-ocular administration).

The compounds of the present invention can be formulated into pharmaceutically-acceptable salt forms. Pharmaceutically-acceptable salts of the compounds of the invention can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydramabine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods

Human Forebrain-Specific NPCs, Astrocytes, Organoids and Cell Line Cultures.

The human iPSC line (C1-2 line) was previously generated from a skin biopsy sample of a healthy male newborn and has been fully characterized and passaged on MEF feeder layers [41]. The BJ line were derived from healthy control fibroblasts obtained from the American Type Culture Collection (CRL-2522, male, neonatal). All studies followed institutional IRB protocols approved by Johns Hopkins University School of Medicine and Florida State University. Human iPSCs were differentiated into forebrain-specific hNPCs following the previously established protocol [41]. Briefly, human iPSC colonies were detached from the feeder layer with 1 mg/ml collagenase treatment for 1 h and suspended in embryonic body (EB) medium, consisting of FGF-2-free iPSC medium supplemented with 2 µM Dorsomorphin and 2 µM A-83 in non-treated polystyrene plates for 4 days with a daily medium change. After 4 days, EB medium was replaced by neural induction medium (NPC medium) consisting of DMEM/F12, N2 supplement, NEAA, 2 µg/ml heparin, and 2 µM cyclopamine. Floating EBs were then transferred to Matrigel-coated 6-well plates at day 7 to form neural tube-like rosettes. Attached rosettes were kept for 15 d with NPC medium change every other day. On day 22, rosettes were picked mechanically and transferred to low attachment plates (Corning) to form neurospheres in NPC medium containing B27. Neurospheres were then dissociated with Accutase at 37° C. for 10 min and placed onto Matrigel-coated 6-well plates at day 24 to form monolayer hNPCs in NPC medium containing B27. These hNPCs expressed forebrain-specific progenitor markers, including NESTIN, PAX6, EMX-1, FOXG1, and OTX2 [41].

Human BJ iPSC line and forebrain NPCs were derived as described previously [42,43]. hNPCs were differentiated to astrocytes and cultured on Matrigel-coated plates in astrocyte medium (ScienCell). Human iPSC-derived forebrain NPCs were maintained at high density, grown on Matrigel (BD bioscience) in NPC media (DMEM/F12, 1×N2, 1×B27-RA (Invitrogen), 1 µg/ml laminin (Invitrogen) and 20 ng/ml FGF2 (Invitrogen)) and split approximately 1:3-1:4 every week with Accutase (Millipore). hNPCs were differentiated to astrocytes and cultured on Matrigel-coated plates in astrocyte medium (Lonza or ScienCell). Astrocytes were split 1:3 every week with Accutase and cultured up to 120 days.

Forebrain-specific organoids were generated from the C2-1 human iPSC line as previously described [44]. Briefly, human iPSC colonies were detached 7 days after passage with Collagenase Type IV, washed with fresh stem cell medium and cultured in a 15 ml conical tube. On day 1, detached and washed iPSC colonies were transferred to an ultra-low attachment 6-well plate (Corning Costar), containing 3 ml of stem cell medium (without FGF-2), plus 2 µM Dorsomorphine (Sigma) and 2 µM A83-01 (Tocris). On days 5-6, half of the medium was replaced with induction medium consisting of DMEM:F12, 1×N2 Supplement (Invitrogen), 10 µg/ml Heparin (Sigma), 1×Penicillin/Streptomycin, 1× Non-essential Amino Acids, 1× Glutamax, 4 ng/ml WNT-3A (R&D Systems), 1 µM CHIR99021 (Cellagentech), and 1 µM SB-431542 (Cellagentech). On day 7, organoids were embedded in Matrigel (BD Biosciences) and continued to grow in induction medium for 6 more days. On day 14, embedded organoids were mechanically dissociated from Matrigel by pipetting up and down onto the plate with a 5 ml pipette tip. Typically, 10-20 organoids were transferred to each well of a 12-well spinning bioreactor (Spine) containing differentiation medium, consisting of DMEM:F12, 1×N2 and B27 Supplements (Invitrogen), 1× Penicillin/Streptomycin, 1×2-Mercaptoenthanol, 1× Non-essential Amino Acids, 2.5 µg/ml Insulin (Sigma).

The glioblastoma SNB-19 cell line (part of the National Cancer Institute 60 human tumor cell line) was a gift from Dr. David Meckes (Florida State University, Tallahassee, Fla.). SNB-19 cells were maintained at 37° C. in 5% $CO_2$ in RPMI-60, 1× penicillin/streptomycin, and 10% fetal bovine serum (Invitrogen). The *Aedes albopictus* C6/36 cell line (ATCC) was maintained at 28° C. in 5% $CO_2$.

Preparation of ZIKV and Cell Infection.

The MR766-ZIKV stock with the titer of 1×10$^5$ Tissue Culture Infective Dose (TCID)/ml in the form of culture fluid from an infected rhesus *Macaca* cell line LLC-MK2, was originally obtained from ZeptoMetrix (Buffalo, N.Y.). The FSS13025-ZIKV strain was obtained from Drs. Robert Tesh and Pei-Yong Shi (University of Texas Medical Branch, Galveston, Tex.). The PRVABC59 strain was obtained from ATCC (Manassas, Va.). Original viral stocks were then amplified in *Aedes albopictus* clone C6/36 cells. Briefly, C6/36 cells were inoculated with viral inoculum for one hour at 28° C. in low volume of media (3 ml per T-75 flask), with rocking every 15 minutes, before addition of 17 ml media. Viral inoculated cells were incubated at 28° C. for 6-7 days before harvesting of supernatant. C6/36-amplified ZIKV titer was determined by infecting Vero cells for 48 hours with a methyl-cellulose overlay and analyzed for focus-forming units per mL (FFU/ml). In mock infections, an equal volume of spent uninfected C6/36 culture medium was used. For infections, cells were seeded into 12-well plates with/without coverslips one day prior to virus addition. For all cell types, compound was added 1 hour prior to viral addition unless otherwise specified. Cells were harvested at 24-72 hours post-infection.

Immunocytochemistry.

Cells were fixed with 4% paraformaldehyde (Sigma) for 15 min at room temperature. Samples were permeabilized and blocked with 0.25% Triton X-100 (Sigma) and 10% donkey or goat serum in PBS for 20 min as previously described (Chiang et al., 2011; [41]; Yoon et al., 2014). Samples were then incubated with primary antibodies at 4° C. overnight, followed by multiple PBST washes and incubation with secondary antibodies for 1 h at room temperature. Slides were mounted using VECTASHIELD with DAPI (Vectorlabs, Burlingame, Calif.). The following primary antibodies were used: anti-flavivirus group antigen (clone D1-4G2-4-15; mouse; 1:500; Millipore), and anti-cleaved caspase-3 (Asp15; Rabbit; 1:500; Cell Signaling Technology). Antibodies were prepared in PBS containing 0.25% Triton X-100 and 10% donkey serum. Images were taken by Zeiss LSM 700 and 880 confocal microscopes, Olympus BX61, or Zeiss Axiovert 200M microscope.

Western Blot.

Cells were harvested by trypsinization, pelleting, and subsequent lysis in 1× Laemlli buffer and boiled, or directly lysed in 1× Laemlli buffer and boiled. Antibodies used were anti-ZIKV NS1 (1:2000; BF-1225-36, BioFront Technologies, Tallahassee, Fla.) or GAPDH (Santa Cruz Biotechnology, Texas).

NS1 ELISA.

The anti-ZIKV NS1 ELISA (ZKV-NS1-EK) was obtained from BioFront Technologies (Tallahassee, Fla.) and used according to the manufacturer's protocol.

Compound Libraries.

The Library of Pharmacologically Active Compounds (LOPAC), consisting of 1280 compounds, was purchased from Sigma-Aldrich. The NCATS pharmaceutical collection, a collection consisting of 2816 clinically approved and investigational drugs, was internally established in 2011 [45]. All compounds were dissolved in DMSO as 10 mM stock solutions, then diluted in DMSO at a 1:3 ratio in 384-well plates, followed by reformatting into 1536-well compound plates use in high-throughput screening (HTS).

Caspase 3/7 Assay.

Caspase-Glo 3/7 assay kit (catalog number G8092; Promega, Madison, Wis.) was used to detect caspase 3/7 activity. Reagents were reconstituted as described in the protocol from the manufacturer. Polystyrene plates (384-well and 1536-well; regular tissue culture treated and PDL coated) were purchased from Greiner Bio-One (Monroe, N.C.). Cells were seeded in 384- and 1536-well assay plates and cultured at 37° C. with 5% $CO_2$ for 16 hours. ZIKV solution was added to cells, followed by incubation at 37° C. with 5% $CO_2$ for 6 hours. Caspase-Glo 3/7 was added to each well, unless otherwise specified, and incubated at room temperature for 30 minutes. The luminescence intensity of the assay plates was measured using a ViewLux plate reader (PerkinElmer). Data were normalized by using the cell-containing wells without ZIKV as a negative control (0% induction of caspase 3/7 activity) and wells containing ZIKV infected cells that induced caspase 3/7 activity were used as a positive control (100% induction of caspase 3/7 activity).

ATP Content Assay for Cell Viability and Compound Cytotoxicity.

The ATPlite luminescence assay system assay kit (catalog number 6016731; PerkinElmer) was used to determine cell viability. The reagent was reconstituted and prepared as described by the manufacturer. In order to measure the cell death caused by ZIKV infection, cells were cultured for 16 hours at 37° C. with 5% $CO_2$ in assay plates, followed by the addition of ZIKV solution and incubation at 37° C. with 5% $CO_2$ for 72 hours. ATPlite, the ATP monitoring reagent, was then added to the assay plates and they were incubated for 15 minutes. The resulting luminescence was measured using the ViewLux plate reader (Perkin Elmer). Data were normalized using the wells without cells as a control for 100% cell killing, and cell-containing wells without ZIKV infection were used as full cell viability (0% cell killing).

Large-Scale Compound Screening.

Human NPCs were seeded onto PDL coated 1536-well assay plates at 250 cells per 3 µl/well and incubated at 37° C. in 5% $CO_2$ for 16 hours. Test compounds dissolved in DMSO were transferred to assay plates at a volume of 23 nl/well by an automated pintool workstation (Wako Automation, San Diego, Calif.). Compounds were incubated with cells for 30 minutes at 37° C. in 5% $CO_2$, immediately followed by the addition of 2 µl/well of ZIKV. Incubation time of compound-treated cells with ZIKV varied based on assay format. Experiments measuring virus-induced caspase 3/7 activity required a 6 hour incubation of ZIKV in the presence compounds at 37° C. in 5% $CO_2$. Following this incubation, 3.5 µl/well of caspase 3/7 reagent mixture was added to assay plates. The plates were incubated for 30 minutes at room temperature, and the resultant luminescence signal was measured using a ViewLux plate reader (Perkin Elmer). Experiments measuring virus-induced cell death required a 72-hour incubation of ZIKV in the presence of compounds at 37° C. in 5% $CO_2$. Following this incubation, 3.5 µl/well of ATP content detection reagent was added to assay plates, incubated for 30 minutes at the room temperature, and the resultant luminescence signal was measured in a ViewLux plate reader. Step-by-step assay protocols are listed in Tables 4 and 5.

Because compound cytotoxicity could nonspecifically reduce the caspase activity induced by ZIKV, the inventors also used the ATP content assay to measure compound cytotoxicity in the absence of ZIKV infection. The cells were seeded in the same way as described above in 1536-well assay plates. After a 6-hour incubation with compounds in the absence of ZIKV, 3.5 µl/well of ATP content reagent mixture was added to the assay plates and incubated for 30 minute at room temperature. The luminescence signal in the assay plates was measured using a ViewLux plate reader (Table 6). Any compounds that exhibited cytotoxicity were eliminated as false positive compounds.

Antiviral Compound Analysis.

SNB-19 cells, BJ astrocytes, or hNPCs were seeded in 12-well plates at approximately 3e5 cells/well. The next day, cells were treated with compound at 1-10×$IC_{50}$ or indicated concentration for 1 hour prior to inoculation with ZIKV at MOI=0.5-1. Cells and supernatant were harvested 24-48 hours post infection and analyzed by western blot or IFA. Western blot bands were quantified and IFA images counted using ImageJ (NIH, Bethesda, Md.).

Data Analysis and Statistics.

The primary screen data and concentration response curves were analyzed using software developed internally [46]. The concentration-response curves and $IC_{50}$ values of compound confirmation data were calculated using Prism software (GraphPad Software, Inc. San Diego, Calif.). All values are expressed as the mean±s.d. unless specified otherwise. Western blots and IFA images were quantified using ImageJ (NIH, Bethesda, Md.).

TABLE 1

Protocol of caspase 3/7 activity assay.

| | | value | | |
|---|---|---|---|---|
| Step | parameter | 384-well | 1536-well | Description |
| 1 | Cell plating | 20 µl/well | 3 µl/well | PDL-coated plates used for NPCs/astrocytes |
| 2 | Incubation | overnight | | at 37° C. with 5% $CO_2$ |
| 3 | Compound addition | 10 µl/well | 23 µl/well | in DMSO solution |
| 4 | Incubation | 30 minutes | | at 37° C. with 5% $CO_2$ |
| 5 | Zika virus addition | | 2 µl/well | |
| 6 | Incubation | 6 hours | | at 37° C. with 5% $CO_2$ |
| 7 | Reagent addition | | 3 µl/well | Caspase 3/7 assay mixture (Promega) |
| 8 | Incubation | 30 minutes | | at room temperature |
| 9 | Plate reading | luminescence mode | | ViewLux plate reader (PerkinElmer) |

TABLE 2

Protocol of ATP cell viability assay for Zika virus induced cell death.

| | | value | | |
|---|---|---|---|---|
| Step | parameter | 384-well | 1536-well | Description |
| 1 | Cell plating | 20 µl/well | 3 µl/well | PDL-coated plates used for NPCs/astrocytes |
| 2 | Incubation | overnight | | at 37° C. with 5% $CO_2$ |
| 3 | Compound addition | 10 µl/well | 23 µl/well | in DMSO solution |
| 4 | Incubation | 30 minutes | | at 37° C. with 5% $CO_2$ |
| 5 | Zika virus addition | | 2 µl/well | |
| 6 | Incubation | 3 days | | at 37° C. with 5% $CO_2$ |
| 7 | Reagent addition | | 3 µl/well | ATP content assay mixture (PerkinElmer) |
| 8 | Incubation | 30 minutes | | at room temperature |
| 9 | Plate reading | luminescence mode | | ViewLux plate reader (PerkinElmer) |

TABLE 3

Protocol of ATP content cell viability assay for compound cytotoxicity.

| | | value | | |
|---|---|---|---|---|
| Step | parameter | 384-well | 1536-well | Description |
| 1 | Cell plating | 20 µl/well | 3 µl/well | PDL-coated plates used for NPCs/astrocytes |
| 2 | Incubation | Overnight | | at 37° C. with 5% $CO_2$ |
| 3 | Compound addition | 10 µl/well | 23 µl/well | in DMSO solution |
| 4 | Incubation | 30 minutes | | at 37° C. with 5% $CO_2$ |
| 5 | Incubation | 6 hours | | at 37° C. with 5% $CO_2$ |
| 6 | Reagent addition | 3 µl/well | | ATP content assay mixture |
| 7 | Incubation | 30 minutes | | at room temperature |
| 8 | Plate reading | luminescence mode | | ViewLux plate reader (PerkinElmer) |

Note:
no Zika virus was added to assay plate in this experiment that was differed from that described in Table 1 and 2.

Example 1—Anti-Zika Virus Screen and Anti-Zika Compounds

Although ZIKV only recently became a global health concern, rapid progress has already been made in understanding its pathogenesis and developing animal models [10-17]. Following clinical observations that ZIKV could be found in fetus brains of infected pregnant women [18,19], the inventors reported that ZIKV can efficiently infect forebrain-specific human neural progenitor cells (hNPCs) and attenuate their growth [10]. These results provide a potential mechanism for ZIKV-induced microcephaly as hNPCs drive the development of human cortex, which is underdeveloped in microcephalic fetuses. Furthermore, the inventors and others have shown that ZIKV infection of brain organoids, 3D cellular models of human brain development, leads to reduced ventricular zone thickness, enlarged lumen, and an overall reduction in organoid size [11,12,15,20], again consistent with features of microcephaly. These results have also been recapitulated in mouse models [15,16]. Despite these advancements in understanding how ZIKV causes developmental abnormalities, there is currently no drug or vaccine available to treat or prevent ZIKV infection.

The inventors performed a drug repurposing screen to identify compounds that either inhibit ZIKV infection or suppress infection-induced caspase-3 activity in neural cell types. A screening of 6,000 compounds that included approved drugs, clinical trial drug candidates and pharmacologically active compounds, identified compounds in both categories. Among these, Emricasan, a pan-caspase inhibitor, potently inhibits ZIKV-induced increase in caspase-3 activity and reduces cell death. The inventors confirmed its efficacy to protect human cortical neural progenitors in both monolayer and organoid cultures. PHA-690509, a cyclin-dependent kinase (CDK) inhibitor, and four structurally unrelated CDK inhibitors, inhibit ZIKV replication in human cells in a dose-dependent manner. In addition, Niclosamide, an FDA approved category B anthelmintic drug, inhibits ZIKV replication at sub-micromolar concentrations. Both CDK inhibitors and Niclosamide are effective in reducing ZIKV replication when added either before or after ZIKV exposure. Finally, a combination of two classes of compounds showed a synergistic effect in protecting human neural cells from ZIKV-induced cell death. The results demonstrate the effectiveness of this compound screening strategy and provide compounds for anti-Zika drug development.

Figure 5A:
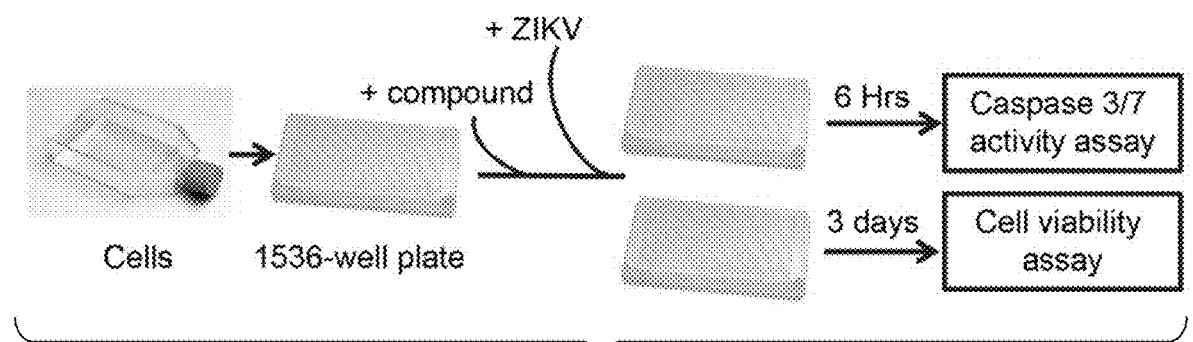
FIGS. 5A-5F. Two high-throughput assays that measure increased caspase-3 activity and reduced cell viability of ZIKV infected cells.

Drug repurposing screens have recently emerged as an alternative approach to accelerate drug development [21, 22]. Following a repurposing phenotypic screen, new indications for existing drugs may be rapidly identified and clinical trials can be carried out quickly, which is of critical importance for rapidly spreading infectious diseases [21,22]. For example, recent drug repurposing screens have led to discoveries of potential new candidate therapies for Ebola virus disease [23,24], Giardiasis [25], *Entamoeba histolytica* infection [26], malaria gametocytes [27], *Exserohilum rostratum* infection [28], and hepatitis C virus infection [29]. Based on the previous finding that ZIKV infection of hNPCs results in an increase of caspase-3 activation, followed by cell death [10], the inventors designed a compound screening approach using caspase-3 activity as the primary screen assay and a cell viability assay for confirmation (FIG. 5A). The inventors identified two classes of effective compounds, one being antiviral and another capable of protecting neural cells from ZIKV-induced cell death. Because ZIKV infects neural cells and causes their death, neuroprotective compounds may provide additional benefits when combined with drugs that inhibit ZIKV replication.

Figure 5B:
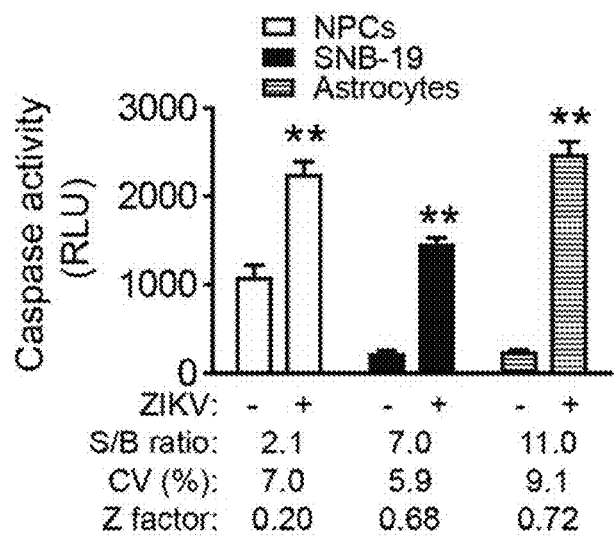

The inventors first quantified caspase-3 activity and cell viability of hNPCs and astrocytes derived from human induced pluripotent stem cells (iPSCs), as well as glioblastoma SNB-19 cells, after ZIKV infection in a 1536-well plate format (Table 4). The prototypic ZIKV strain, MR766, was used in the primary screen because it produced the strongest cell death signal in cell culture experiments. The signal-to-basal (SB) ratio and coefficient of variation (CV) obtained in the caspase-3 activity assay after 6-hour ZIKV exposure were 2.1-fold and 7.0% for hNPCs, 7.0-fold and 5.9% for SNB-19 cells, and 11.0-fold and 9.1% for astrocytes (FIG. 5B). The Z' factors for hNPCs, SNB-19, and human astrocytes were 0.20, 0.68, and 0.72, respectively. Since a Z' factor over 0.5 indicates a robust screening assay [30], the caspase assay using SNB-19 cells or astrocytes is suitable for high-throughput screening of compound collections.

Figure 5C:
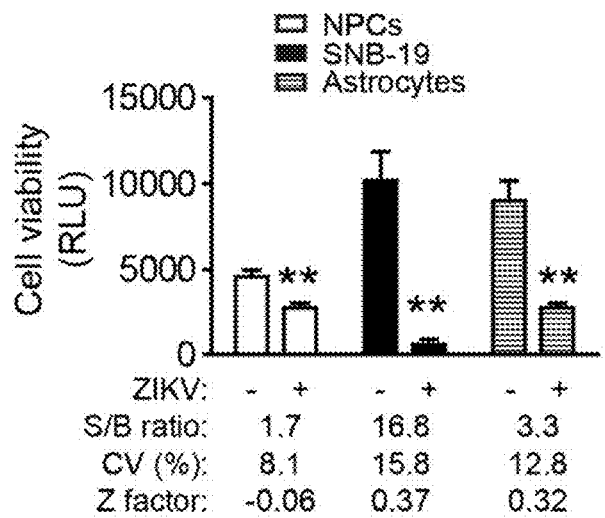

To measure cell viability following ZIKV infection for 3 days, the inventors applied an ATP content assay in a 1536-well plate format (FIG. 5A and Table 5). Cell viability was reduced by 39%, 82%, and 69% in hNPCs, SNB-19 cells, and human astrocytes, respectively (FIG. 5C). The Z' factors in these three cell types were −0.06, 0.37 and 0.32, respectively. Together, the results indicated the caspase-3 activity assay is a better option for high-throughput compound screening than the cell viability assay.

The inventors carried out a screening campaign using the caspase-3 activity assay and SNB-19 cells with the Library of Pharmacologically Active Compounds (LOPAC, 1280 compounds), the NCATS Pharmaceutical Collection of approved drugs (2816 compounds), and a collection of clinical candidate compounds (2000 compounds). Primary hits included a total of 116 compounds that suppressed ZIKV-induced caspase 3 activity in SNB-19 cells. The inventors also carried out an independent primary screen using hNPCs with the same libraries. This second screen resulted in 173 primary hits that included all 116 compounds from the first caspase-3 screen in SNB-19 cells. All results of the primary screen of the approved drug collection and hit confirmation were deposited into the open-access PubChem database (pubchem.ncbi.nlm.nih.gov).

Figure 5D:
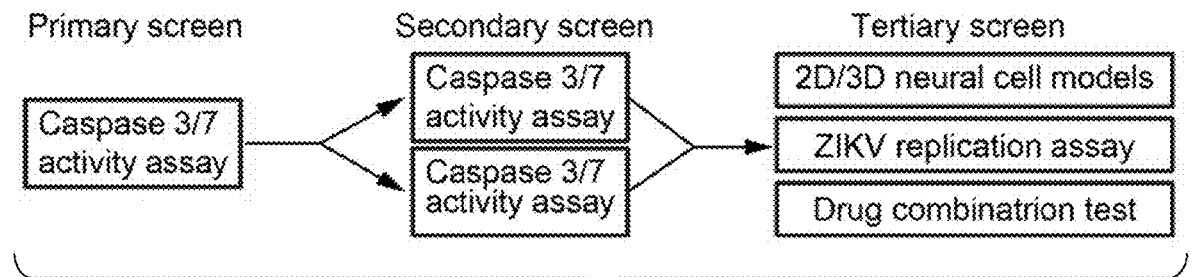

Next, the activity of these primary hits in the caspase-3 activity assay was evaluated in ZIKV-infected SNB-19 cells, hNPCs, and astrocytes in parallel with the compound cytotoxicity assay (FIGS. 5C-5D and Table 6). Cytotoxic compounds were then eliminated from the confirmed compound list. Consistent with the screening design, the inventors identified compounds that reduced virally-induced caspase activation and apoptosis by either directly preventing ZIKV-induced cell death or suppressing ZIKV replication (Table 7).

Figures 1, 1A, 2, 3:
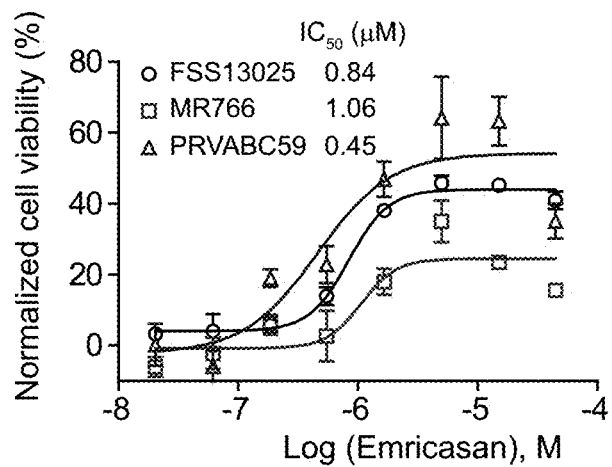
Figures 1, 1B:
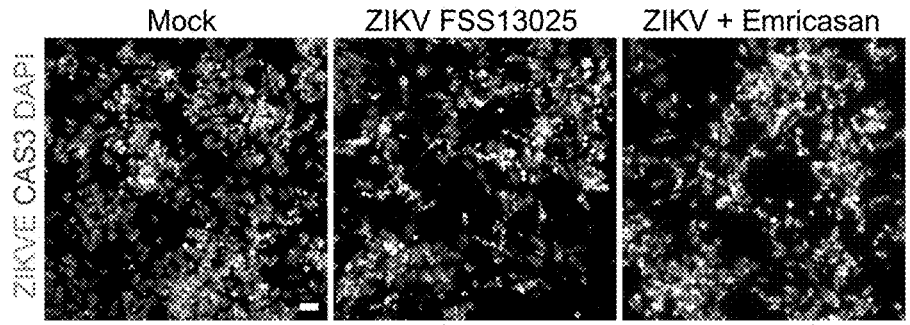
Figures 1, 1B, 2:
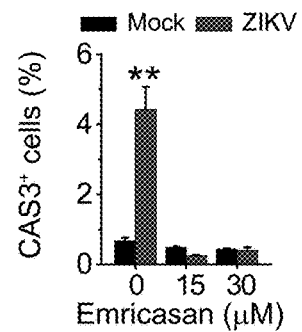
Figures 1, 1C:
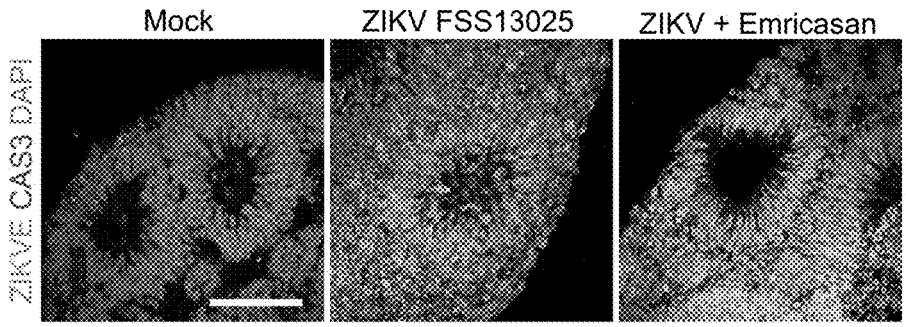
Figures 1, 1C, 2:
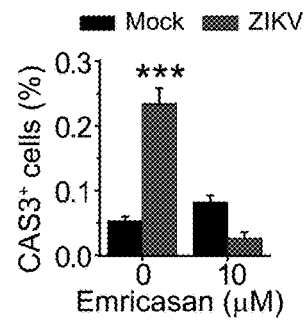
Figures 1, 2E:
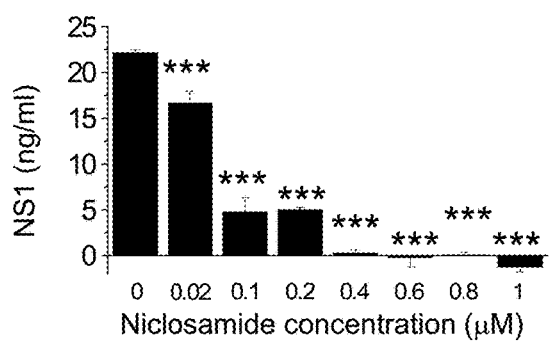
Figures 2, 2E:
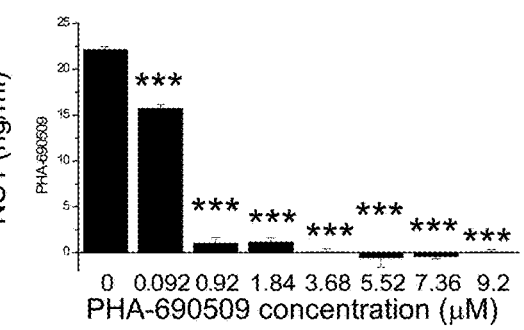
Figure 2F:
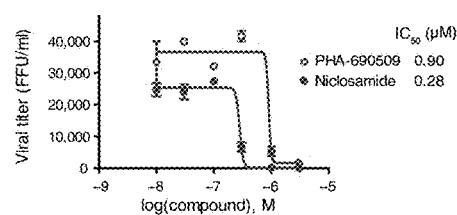
Figure 5E:
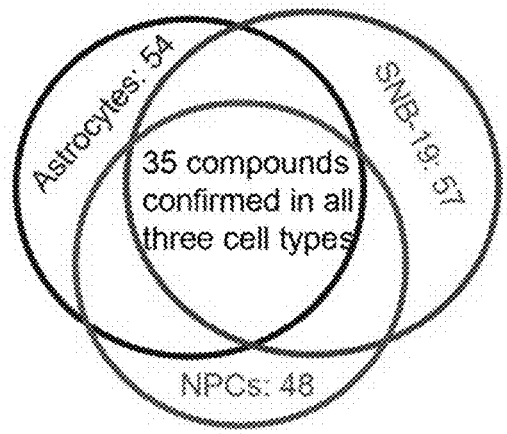
Figure 5F:
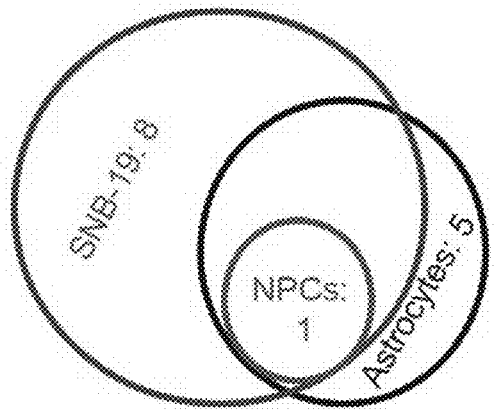
Figure 6A:
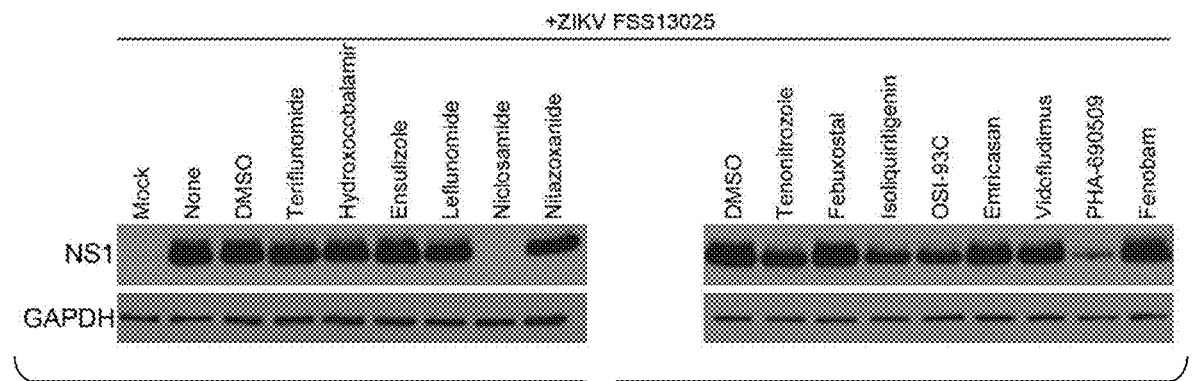
FIGS. 6A-6F. Niclosamide and PHA-690509 inhibit ZIKV infection in a dose-dependent manner.
Figure 6B:
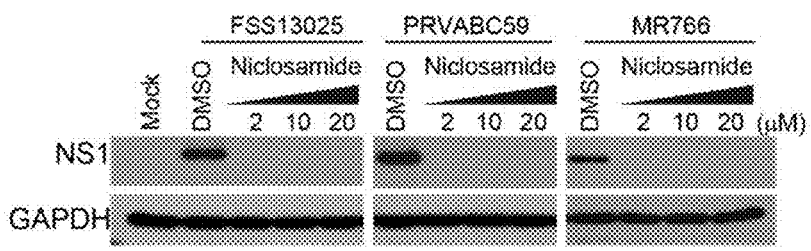
Figure 6C:
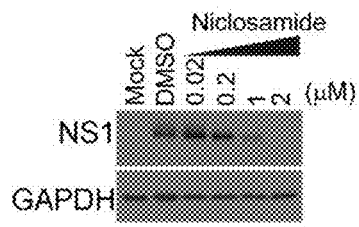
Figure 6D:
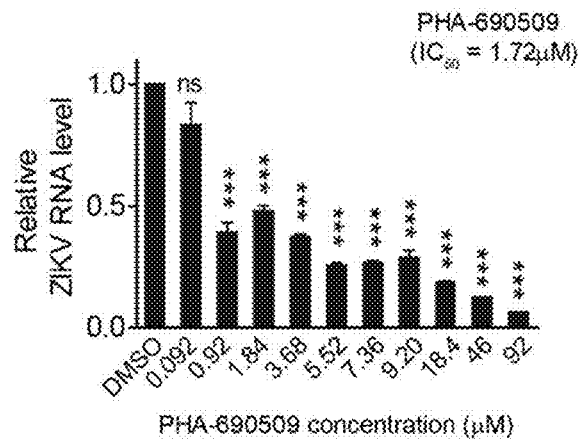
Figure 6E:
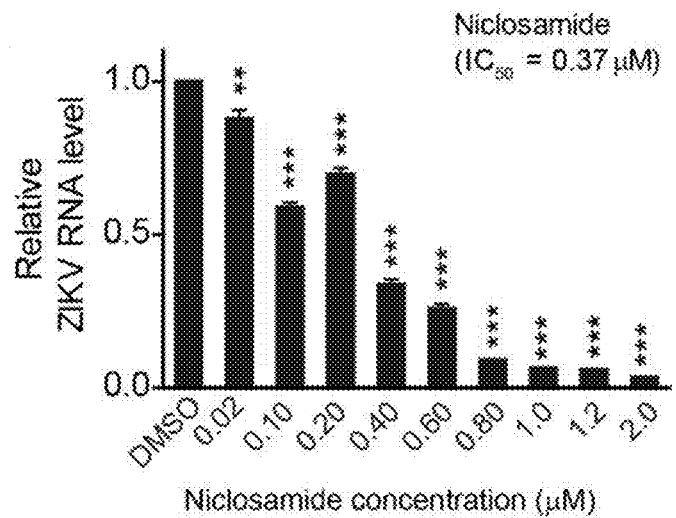
Figure 6F:
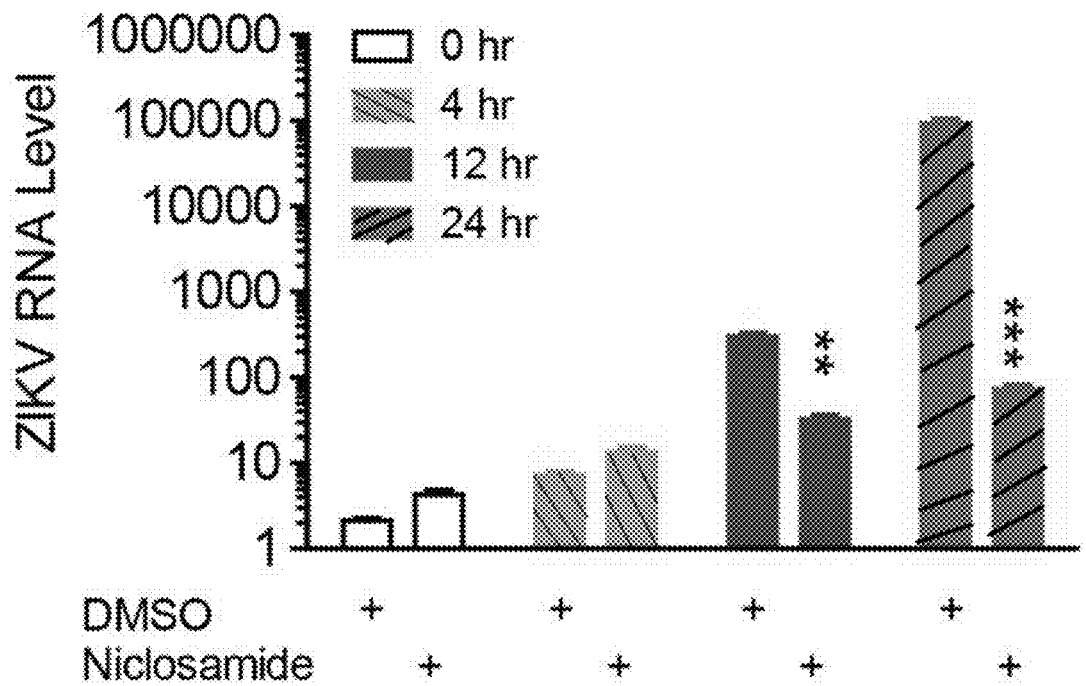

Emricasan, a pan-caspase inhibitor, was identified as the most potent anti-death compound with $IC_{50}$ values of 0.13-0.9 µM in both the caspase activity assay and the cell viability assay in SNB-19 cells against three ZIKV strains: MR766 (1947 Uganda strain), FSS13025 (2010 Cambodian strain), and PRVABC59 (2015 Puerto Rican strain) (FIG. 1A). It was also active in all three cell types tested (FIG. 5E and Table 8). Finally, Emricasan reduced the number of active (cleaved) caspase-3-expressing forebrain-specific hNPCs infected by FSS13025 in both monolayer and 3D organoid cultures (FIGS. 1B-1C). ZIKV antigen persisted in both 2D and 3D cultures after Emricasan treatment (FIGS. 1B-1C). Therefore, Emricasan displays protective activity for hNPCs, but does not suppress ZIKV replication.

Using ZIKV protein NS1 expression as a read-out for testing anti-ZIKV activity, the inventors identified two compounds that significantly inhibited ZIKV infection in SNB-19 cells (FIG. 2A). The first was Niclosamide, an FDA-approved drug for treating worm infections in both humans and domestic livestock; the other was PHA-690509, an investigational compound and an inhibitor of cyclin-dependent kinases (CDKs). Both compounds inhibited all three strains of ZIKV in a dose-dependent manner, with $IC_{50}$ values of 12 to 36 µM for PHA-690509 and over ten-fold lower at 0.5-2 µM for Niclosamide (FIGS. 2B-2E and FIGS. 6A-6B). To explore the mechanism of action for these compounds, the inventors performed time-of-addition experiments (FIG. 3A). Both compounds effectively inhibited ZIKV infection when added either 1 hour before or 4 hours after virus inoculation (FIG. 3B). In contrast, a monoclonal antibody against AXL, a putative ZIKV entry factor [31,32], was only effective when added prior to inoculation (FIG. 3B). Together, these results indicate that Niclosamide and PHA-690509 inhibit ZIKV infection at a post-entry stag.

Figures 1, 3C:
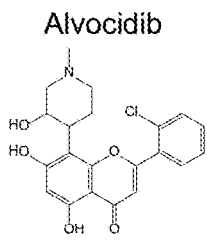
Figures 2, 3C:
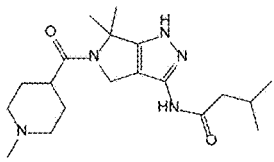
Figures 3, 3C:
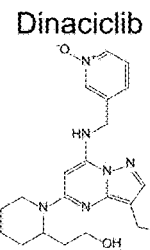
Figure 7A:
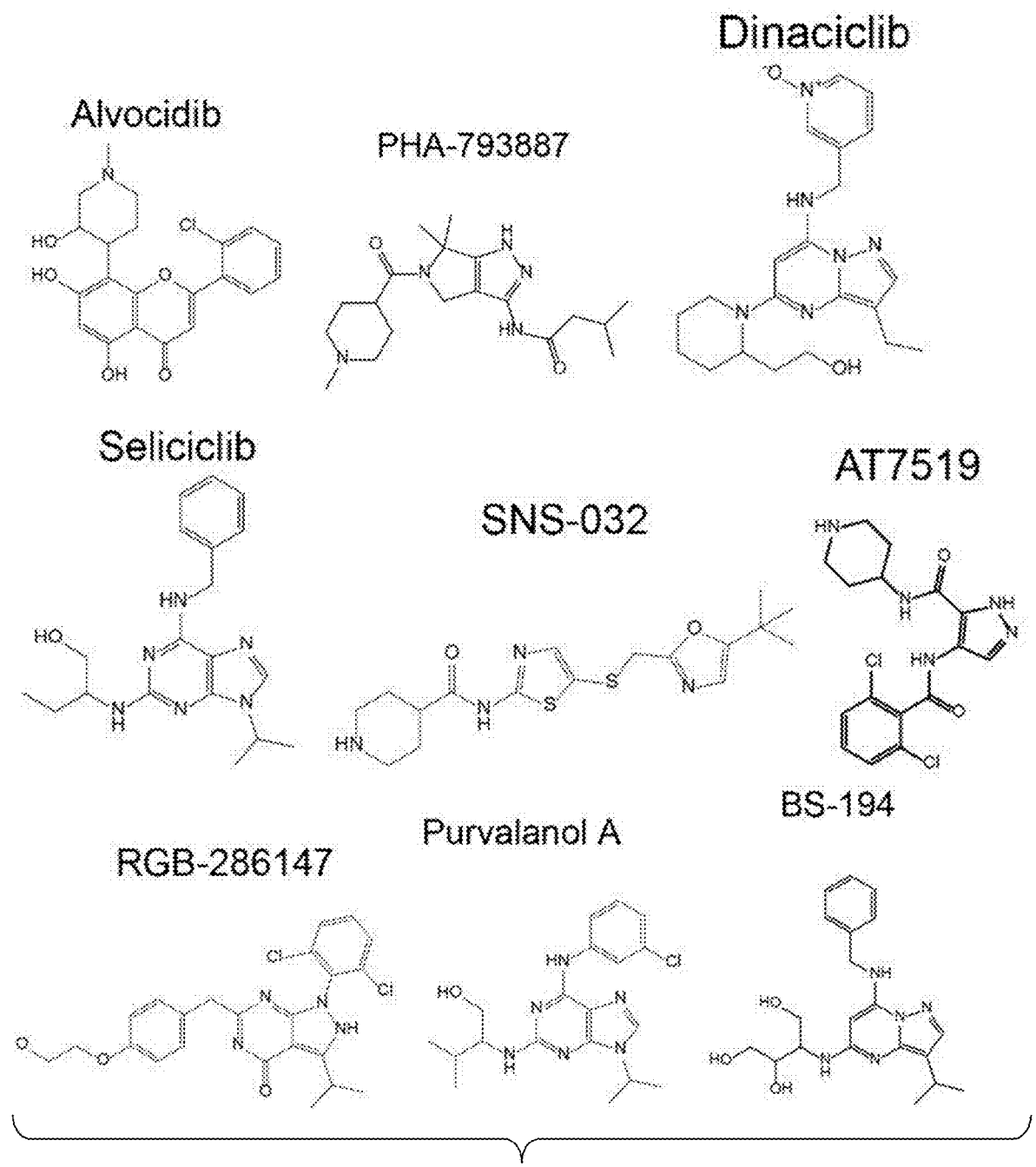
Figures 1, 7B:
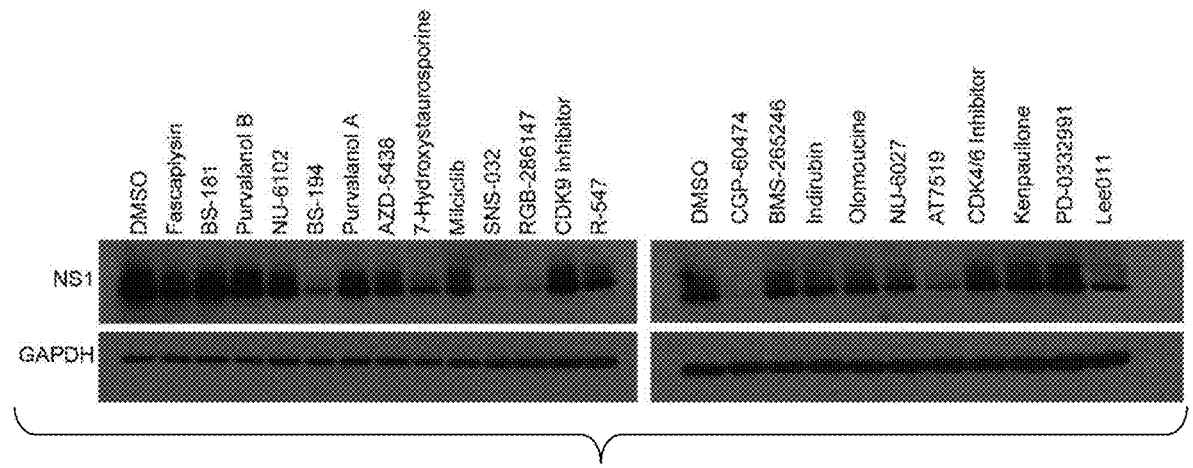
Figures 2, 7B:
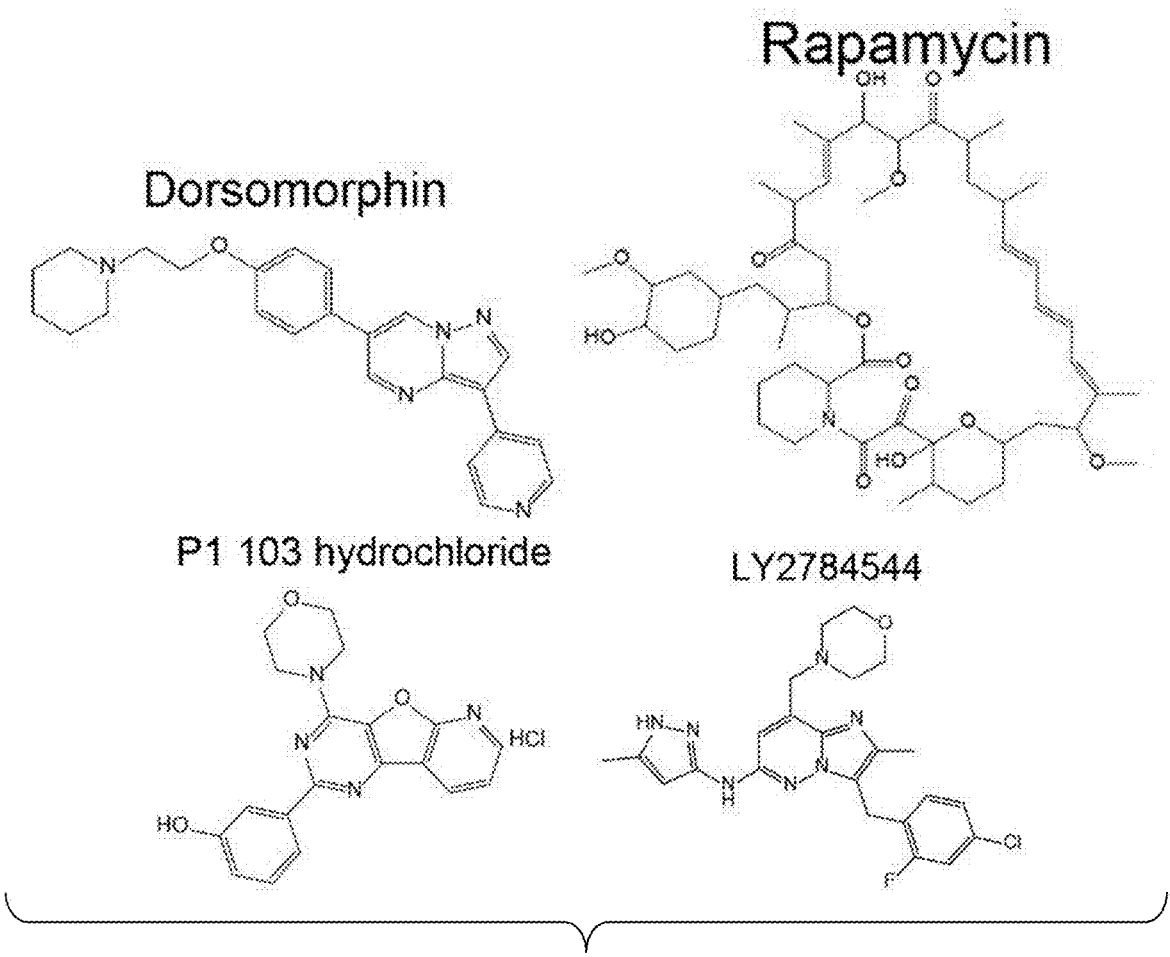
Figures 3, 7B:
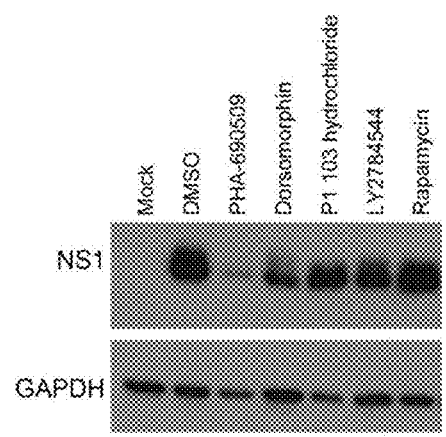

Pharmacological CDK inhibitors have been shown to inhibit replication of diverse viruses in culture, including herpes viruses and HIV [33], but identification of a CDK inhibitor is particularly intriguing given the recent observation that ZIKV infection and cell cycle regulation are closely connected [10]. The inventors therefore tested four additional structurally distinct CDK inhibitors for ZIKV inhibition (FIG. 3C). All four CDK inhibitors effectively inhibited ZIKV (FIG. 3D), whereas four other non-CDK kinase inhibitors exhibited minimal anti-ZIKV activity in SNB-19 cells (FIGS. 7A-7B). The inventors also examined whether these compounds could inhibit ZIKV infection in hNPCs and astrocytes using the clinical isolate from the 2015 Puerto Rico Zika outbreak, PRVABC59. Niclosamide and PHA-690509 inhibited $ZIKV^{PR}$ infection in these central nervous system cells (FIGS. 4A-4B), both of which are target cells for ZIKV infection in the fetal brain [34].

Figures 3, 3C, 4:
Figures 3, 3C, 4, 5:
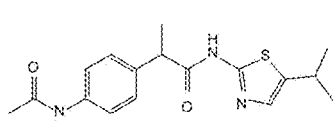
Figures 1, 3D:
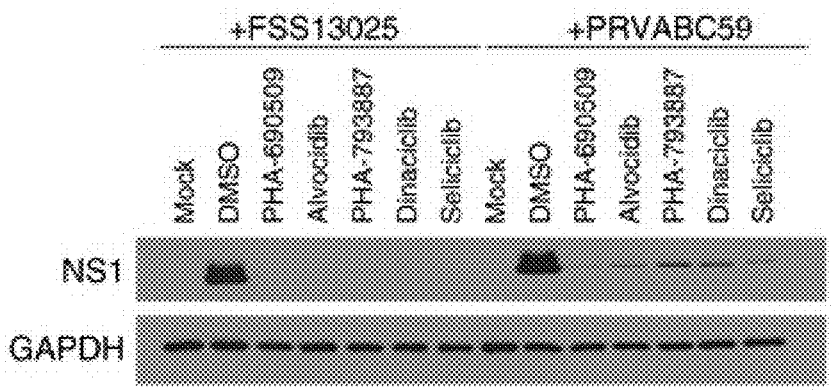
Figures 2, 3D:
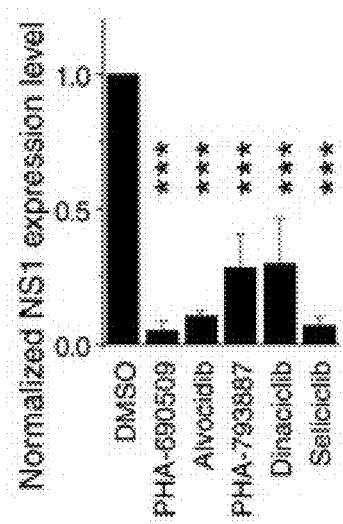
Figure 8A:
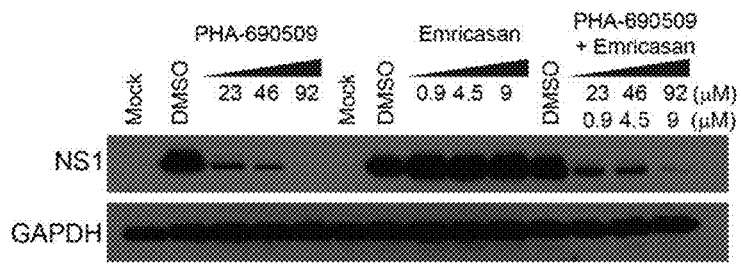
Figure 8B:
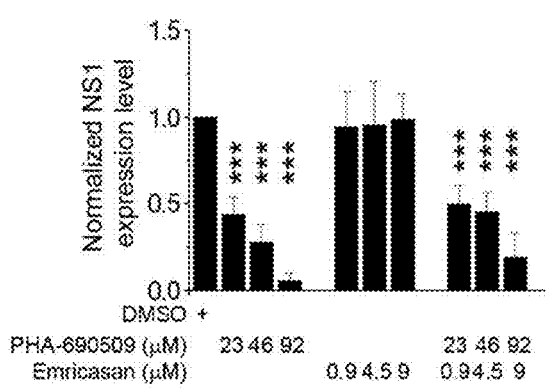
Figure 8C:
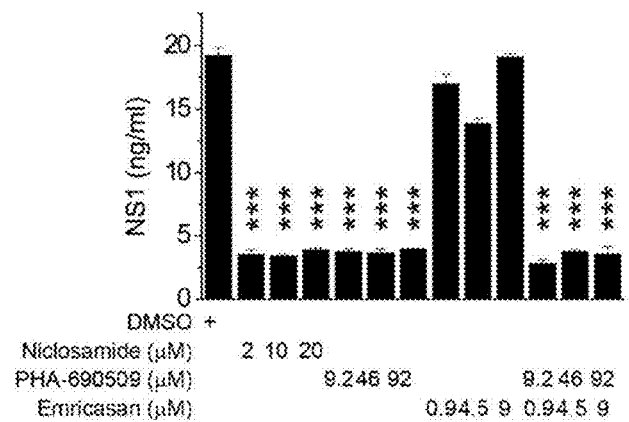
Figure 10:
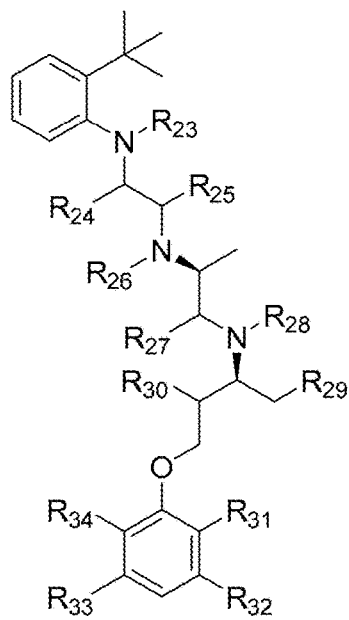
FIG. 10. Formula encompassing Emricasan and derivatives of Emricasan, (Formula 5).

Finally, the inventors tested a combination of these two classes (anti-death and antiviral) of compounds for synergistic effects in protecting neural cells from ZIKV-induced death. The inventors found that in the two-drug combination of Emricasan and PHA-690509, much lower concentrations of each drug were needed for inhibiting caspase-3 activity (FIG. 4C). A similar synergistic effect to preserve neural cell viability after ZIKV infection was also observed (FIG. 4D). Importantly, Emricasan did not interfere with PHA's ability to inhibit ZIKV infection in the combination (FIGS. 8A-8C).

Emricasan, also named IDN-6556 or PF-03491390, is a pan-caspase inhibitor that reduces liver injury and fibrosis in a murine model of non-alcoholic steatohepatitis [35], where hepatocyte apoptosis is a hallmark of the disease [35]. When evaluated in clinical trials for chronic Hepatitis C patients, Emricasan reduced liver injury and was tolerated over 12 weeks [36,37]. It was reported that the overall (AUC) and maximum (Cmax) concentration of Emricasan in human blood (oral, BID, ×4 days) were 1.90 µg/ml (3.35 µM) and 2.36 µg/ml (4.15 respectively. Therefore, Emricasan's plasma concentration in humans could be suitable for protecting cells from ZIKV infection-induced death.

PHA-690509 and the other four CDK inhibitors are all in clinical trials for other indications. The inventors show that these additional CDK inhibitors with unrelated structures also inhibit ZIKV replication, supporting a role for CDKs in the life cycle of ZIKV in human cells. As flaviviruses are not known to encode any CDKs, these results suggest that one or more of cellular CDKs in the host may be important for ZIKV replication. Further studies on target identification for PHA-690509, including targeted kinome siRNA or CRISPR screens, may reveal additional insights into the mechanism of these inhibitors.

Niclosamide is an FDA-approved drug that is currently prescribed to treat worm infections, but it has been reported to inhibit viruses in culture systems [38-40]. Its broad antiviral activity has been attributed to its ability to neutralize endo-lysosomal pH and interfere with pH-dependent membrane fusion [39], which is an essential step in the common virus entry pathway. The data indicate that Niclosamide suppresses ZIKV infection when added 4 hours after virus inoculation, suggesting significant inhibition at a post-entry step, such as replication. Regardless of the mechanism of action, Niclosamide is a category B drug, for which no risk to fetus has been found in animal studies; it therefore represents a promising candidate for a drug to be repurposed for reducing ZIKV viral load in pregnant women.

Given the significant time needed to develop and test effective vaccines, countermeasures against ZIKV, including small molecule therapeutics, are urgently needed. The inventors have developed two ultra-high throughput assays that measure ZIKV-induced caspase 3 activity and reduced cell viability and screened approximately 6,000 approved drugs and drug candidate compounds. The inventors' efforts so far have led to the identification of small molecules that either protect against cell death or suppress ZIKV replication. The two groups of antiviral compounds, Niclosamide and CDK inhibitors, likely act via distinct mechanisms to inhibit ZIKV, and thus present an opportunity for a combination treatment regimen. The structural diversity of effective CDK inhibitors provides multiple chemical scaffolds to which medicinal chemistry could be applied. The findings and tools provided here will significantly advance the current ZIKV research and have an immediate impact on the development of anti-ZIKV therapeutics.

Further details concerning the screen and identified compounds can be found in [47], which is incorporated herein by reference in its entirety.

Supplemental Information—Expanded Materials and Methods

Cell Lines.

Human iPSCs were cultured and differentiated into cortical neural progenitor cells as described previously [41]. The human iPSC line was previously generated from a skin biopsy sample of a male newborn (C1-2 line), and has been fully characterized and passaged on MEF feeder layers [41]. All studies followed institutional IRB protocols approved by Johns Hopkins University School of Medicine and Florida State University. Human iPSCs were differentiated into forebrain-specific hNPCs and immature neurons following the previously established protocol [41]. Briefly, hiPSC colonies were detached from the feeder layer with 1 mg/ml collagenase treatment for 1 h and suspended in embryonic body (EB) medium, consisting of FGF-2-free iPSC medium supplemented with 2 µM Dorsomorphin and 2 µM A-83 in non-treated polystyrene plates for 4 days with a daily medium change. After 4 days, EB medium was replaced by neural induction medium (NPC medium) consisting of DMEM/F12, N2 supplement, NEAA, 2 µg/ml heparin, and 2 µM cyclopamine. Floating EBs were then transferred to Matrigel-coated 6-well plates at day 7 to form neural tube-like rosettes. Attached rosettes were kept for 15 d with NPC medium change every other day. On day 22, rosettes were picked mechanically and transferred to low attachment plates (Corning) to form neurospheres in NPC medium containing B27. Neurospheres were then dissociated with Accutase at 37° C. for 10 min and placed onto Matrigel-coated 6-well plates at day 24 to form monolayer hNPCs in NPC medium containing B27. These hNPCs expressed forebrain-specific progenitor markers, including NESTIN, PAX6, EMX-1, FOXG1, and OTX2 [41].

The human astrocytes (BJ line) were derived from healthy control fibroblasts which were obtained from the American Type Culture Collection (CRL-2522, male, neonatal). hiPSC and forebrain NPCs were derived as described previously [42,43] hNPCs were differentiated to astrocytes and cultured on Matrigel-coated plates in astrocyte medium (ScienCell). Astrocytes were split 1:3 every week with Accutase and could be expanded up to 120 days in astrocyte medium. Human astrocytes and neural progenitor cells were differentiated from human induced pluripotent stem cells as described previously.

Human cerebral organoids were culture as described previously [44]. To generate forebrain-specific organoids, human iPSC colonies were detached 7 days after passage with Collagenase Type IV, washed with fresh stem cell medium and cultured in a 15 ml conical tube. On day 1, detached and washed iPSC colonies were transferred to an Ultra-Low attachment 6-well plate (Corning Costar), containing 3 ml of stem cell medium (without FGF-2), plus 2 µM Dorsomorphine (Sigma) and 2 µM A83-01 (Tocris). On days 5-6, half of the medium was replaced with induction medium consisting of DMEM:F12, 1×N2 Supplement (Invitrogen), 10 µg/ml Heparin (Sigma), 1× Penicillin/Streptomycin, 1× Non-essential Amino Acids, 1× Glutamax, 4 ng/ml WNT-3A (R&D Systems), 1 µM CHIR99021 (Cellagentech), and 1 µM SB-431542 (Cellagentech). On day 7, organoids were embedded in Matrigel (BD Biosciences) and continued to grow in induction medium for 6 more days. On day 14, embedded organoids were mechanically dissociated from Matrigel by pipetting up and down onto the plate with a 5 ml pipette tip. Typically, 10-20 organoids were transferred to each well of a 12-well spinning bioreactor (Spine) containing differentiation medium, consisting of DMEM:F12, 1×N2 and B27 Supplements (Invitrogen), 1× Penicillin/Streptomycin, 1×2-Mercaptoenthanol, 1× Non-essential Amino Acids, 2.5 µg/ml Insulin (Sigma).

The glioblastoma SNB-19 cell line (part of the National Cancer Institute 60 human tumor cell line) was a gift from Dr. David Meckes (FSU, Tallahassee, Fla.). SNB-19 cells were maintained at 37° C. in 5% $CO_2$ in RPMI-60, 1× penicillin/streptomycin, and 10% fetal bovine serum (Invitrogen). The *Aedes albopictus* C6/36 cell line (ATCC) was maintained at 28° C. in 5% $CO_2$.

Human astrocytes and neural progenitor cells were differentiated from human induced pluripotent stem cells as described previously [41]. Luminescence caspase 3/7 activity assay kits (catalog number G8092) were obtained from Promega (Madison, Wis.). ATPlite 1 step Luminescence Assay System kits (catalog number 6016731) for the ATP content cell viability assay were purchased from PerkinElmer. Polystyrene plates (384-well and 1536-well; regular tissue culture treated and PDL coated) were purchased from Greiner Bio-One (Monroe, N.C.).

Preparation of ZIKV and Cell Infection.

The MR766-ZIKV stock with the titer of $1\times10^5$ Tissue Culture Infective Dose (TCID)/ml in the form of culture fluid from an infected rhesus *Macaca* cell line LLC-MK2, was originally obtained from ZeptoMetrix (Buffalo, N.Y.). The F5513025-ZIKV strain was shared by Drs. Robert Tesh and Pei-Yong Shi (University of Texas Medical Branch, Galveston, Tex.). The PRVABC59 strain was obtained from ATCC (Manassas, Va.). Original viral stocks were then amplified in *Aedes albopictus* clone C6/36 cells. Briefly, C6/36 cells were inoculated with viral inoculum for one hour at 28° C. in low volume of media (3 mL per T-75 flask), with rocking every 15 minutes, before addition of 17 mL media. Viral inoculated cells were incubated at 28° C. for 6-7 days before harvesting of supernatant. C6/36-amplified ZIKV titer was determined by infecting vero cells for 48 hours with a methyl-cellulose overlay and analyzed for focus-forming units per mL (FFU/mL). In mock infections, an equal volume of spent uninfected C6/36 culture medium was used. For infections, cells were seeded into 12-well plates with/without coverslips one day prior to virus addition. For all cell types, compound was added 1 hr prior to viral addition unless otherwise specified. For neural progenitor cell infections, viral inoculum was added for 2 hours before being removed and replaced with fresh media. Cells were harvested at 24-72 hours post-infection.

Immunocytochemistry.

Cells were fixed with 4% paraformaldehyde (Sigma) for 15 min at room temperature. Samples were permeabilized and blocked with 0.25% Triton X-100 (Sigma) and 10% donkey or goat serum in PBS for 20 min as previously described (Chiang et al., 2011; [41]; Yoon et al., 2014). Samples were then incubated with primary antibodies at 4° C. overnight, followed by multiple PBST washes and incubation with secondary antibodies for 1 h at room temperature. Slides were mounted using VECTASHIELD with DAPI (Vectorlabs, Burlingame, Calif.). The following primary antibodies were used: anti-Flavivirus Group Antigen (clone D1-4G2-4-15; mouse; 1:500; Millipore), and anti-Cleaved caspase-3 (Asp15; Rabbit; 1:500; Cell Signaling Technology). Antibodies were prepared in PBS containing 0.25% Triton X-100 and 10% donkey serum. Images were taken by Zeiss LSM 700 and 880 confocal microscopes, Olympus BX61, or Zeiss Axiovert 200M microscope.

Western Blot.

Cells were harvested by trypsinization, pelleting, and subsequent lysis in 1× Laemlli buffer and boiled, or directly lysed in 1× Laemlli buffer and boiled. Antibodies used were anti-ZIKV NS1 (1:2000; BF-1225-36, BioFront Technologies, Tallahassee, Fla.) or GAPDH (Santa Cruz Biotechnology, Texas).

NS1 ELISA.

The anti-ZIKV NS1 ELISA (ZKV-NS1-EK) was obtained from BioFront Technologies (Tallahassee, Fla.) and used according to the manufacturer's protocol.

Compound Libraries.

The Library of Pharmacologically Active Compounds (LOPAC), consisting of 1280 compounds, was purchased from Sigma-Aldrich. The NCGC pharmaceutical collection, a collection consisting of 2816 clinically approved drugs, was internally established in 2011 [16]. All compounds were dissolved in DMSO as 10 mM stock solutions, then diluted in DMSO at a 1:3 ratio in 384-well plates, followed by reformatting into 1536-well compound plates use in high-throughput screening (HTS).

Caspase 3/7 Assay.

Caspase-Glo 3/7 assay kit (Promega) was used to detect caspase 3/7 activity. Reagents were reconstituted as described in the protocol from the manufacturer. Cells were seeded in 384- and 1536-well assay plates and cultured at 37° C. with 5% $CO_2$ for 16 hours. ZIKV solution was added to cells, followed by incubation at 37° C. with 5% $CO_2$ for 6 hours. Caspase-Glo 3/7 was added to each well at a 1:1 ratio, unless otherwise specified, and incubated at room temperature for 30 minutes. The luminescence intensity of the assay plates was measured using a ViewLux plate reader (PerkinElmer). Data was normalized by using the cell-containing wells without ZIKV as a negative (0% induction of caspase 3/7 activity) control and wells containing ZIKV infected cells that induced caspase 3/7 activity were used as a positive control (100% induction of caspase 3/7 activity).

ATP Content Assay for Cell Viability and Compound Cytotoxicity.

The ATPlite luminescence assay system assay kit (PerkinElmer) was used to determine cell viability. The reagent was reconstituted and prepared as described by the manufacture. In order to measure the cell death caused by ZIKV infection, cells were cultured for 16 hours at 37° C. with 5% $CO_2$ in assay plates, followed by addition of ZIKV solution and incubation at 37° C. with 5% $CO_2$ for 72 hours. ATPlite, the ATP monitoring reagent, was then added to the assay plates and incubated for 15 minutes. The resulting luminescence was measured using the ViewLux plate reader (Perkin Elmer). Data was normalized using the wells without cells as a control for 100% cell killing, and cell-containing wells without ZIKV infection were used as full cell viability (0% cell killing).

Large-Scale Compound Screening.

Human NPCs were seeded onto PDL coated 1536-well assay plates at 250 cells per 3 µl/well and incubated at 37° C. in 5% $CO_2$ for 16 hours. Test compounds dissolved in DMSO were transferred to assay plates at a volume of 23 nl/well by an automated pintool workstation (Wako Automation, San Diego, Calif.). Compounds were incubated with cells for 30 minutes at 37° C. in 5% $CO_2$, immediately followed by the addition of 2 μl/well of ZIKV. Incubation time of compound-treated cells with ZIKV varied based on assay format. Experiments measuring virus induced caspase 3/7 activity required a 6 hour incubation of ZIKV in the presence compounds at 37° C. in 5% $CO_2$. Following this incubation, 3 μl/well of caspase 3/7 reagent mixture was added to assay plates, incubated for 30 minute at room temperature, and the resultant luminescence signal was measured using a ViewLux plate reader (Perkin Elmer). Experiments measuring the virus induced cell death required a 72 hour incubation of ZIKV in the presence of compounds at 37° C. in 5% $CO_2$. Following this incubation, 3 μl/well of ATP content detection reagent was added to assay plates, incubated for 30 minute at room temperature, and the resultant luminescence signal was measured in a ViewLux plate reader. Step-by-step assay protocols are listed in Table 1 and Table 2.

Because compound cytotoxicity could nonspecifically reduce the caspase activity induced by ZIKV, the inventors also used the ATP content assay to measure compound cytotoxicity in the absence of ZIKV infection. The cells were seeded in the same way as described above in 1536-well assay plates. After a 6 hour incubation with compounds in the absence of ZIKV, 3 μl/well of ATP content reagent mixture was added to the assay plates and incubated for 30 minute at room temperature. The luminescence signal in the assay plates was measured using a ViewLux plate reader (Table 3). Any compounds that exhibited cytotoxicity were eliminated as false positive compounds.

Antiviral Compound Analysis.

SNB-19, BJ astrocyte, or NPCs were seeded in 12-well plates at approximately 3e5 cells/well. The next day, cells were treated with compound at 1-10×$IC_{50}$ or indicated concentration for 1 hour prior to inoculation with virus at MOI=0.5-1. Cells and supernatant were harvested 24-48 hours post infection and analyzed by western blot or IFA. Western blot bands were quantified and IFA images counted using ImageJ (NIH, Bethesda, Md.).

Data Analysis and Statistics.

The primary screen data and curve fitting were analyzed using software developed internally [17]. The concentration-response curves and $IC_{50}$ values of compound confirmation data were calculated using Prism software (GraphPad Software, Inc. San Diego, Calif.). All values are expressed as the mean+/−SD (n≥3) unless it was specified. Western blots and IFA images were quantified using ImageJ (NIH, Bethesda, Md.).

TABLE 4

Protocol of caspase 3/7 activity assay.

| | | Value | | |
|---|---|---|---|---|
| Step | Parameter | 384-well | 1536-well | Description |
| 1 | Cell plating | 20 μl/well | 3 μl/well | PDL-coated plates used for hNPCs/astrocytes |
| 2 | Incubation | overnight | | at 37° C. with 5% $CO_2$ |
| 3 | Compound addition | 6 μl/well | 0.023 μl/well | in DMSO solution |
| 4 | Incubation | 30 minutes | | at 37° C. with 5% $CO_2$ |
| 5 | Zika virus addition | 4 μl/well | 2 μl/well | |
| 6 | Incubation | 6 hours | | at 37° C. with 5% $CO_2$ |

TABLE 4-continued

Protocol of caspase 3/7 activity assay.

| | | Value | | |
|---|---|---|---|---|
| Step | Parameter | 384-well | 1536-well | Description |
| 7 | Reagent addition | 30 μl/well | 3.5 μl/well | Caspase 3/7 assay mixture |
| 8 | Incubation | 30 minutes | | at room temperature |
| 9 | Plate reading | luminescence mode | | ViewLux plate reader |

TABLE 5

Protocol of ATP cell viability assay for ZIKV-induced cell death.

| | | Value | | |
|---|---|---|---|---|
| Step | parameter | 384-well | 1536-well | Description |
| 1 | Cell plating | 20 μl/well | 3 μl/well | PDL-coated plates used for hNPCs/astrocytes |
| 2 | Incubation | overnight | | at 37° C. with 5% $CO_2$ |
| 3 | Compound addition | 6 μl/well | 0.023 μl/well | in DMSO solution |
| 4 | Incubation | 30 minutes | | at 37° C. with 5% $CO_2$ |
| 5 | Zika virus addition | 4 μl/well | 2 μl/well | |
| 6 | Incubation | 3 days | | at 37° C. with 5% $CO_2$ |
| 7 | Reagent addition | 30 μl/well | 3.5 μl/well | ATP content assay mixture |
| 8 | Incubation | 15 minutes | | at room temperature |
| 9 | Plate reading | luminescence mode | | ViewLux plate reader |

TABLE 6

Protocol of ATP content cell viability assay for compound cytotoxicity.

| | | Value | | |
|---|---|---|---|---|
| Step | parameter | 384-well | 1536-well | Description |
| 1 | Cell plating | 24 μl/well | 5 μl/well | PDL-coated plates used for NPCs/astrocytes |
| 2 | Incubation | Overnight | | at 37° C. with 5% $CO_2$ |
| 3 | Compound addition | 6 μl/well | 0.023 μl/well | in DMSO solution |
| 4 | Incubation | 30 minutes | | at 37° C. with 5% $CO_2$ |
| 5 | Incubation | 6 hours | | at 37° C. with 5% $CO_2$ |
| 6 | Reagent addition | 30 μl/well | 3.5 μl/well | ATP content assay mixture |
| 7 | Incubation | 15 minutes | | at room temperature |
| 8 | Plate reading | luminescence mode | | ViewLux plate reader |

Note:
no Zika virus was added to assay plate in this experiment.

TABLE 7

List of compounds including 35 confirmed compounds determined in the
caspase 3/7 assay with hNPCs, SNB-19 cells, and human astrocytes.

| SampleID | Name | Library | Caspase 3 (IC50, uM) | | | Cell viability (IC50, uM) | | | Caspase 3 (efficacy, %) | | | Cell viability (efficacy, %) | | |
|---|---|---|---|---|---|---|---|---|---|---|---|---|---|---|
| | | | Astrocyte | SNB-19 | NPCs | Astrocyte | SNB-19 | NPCs | Astrocyte | SNB-19 | NPCs | Astrocyte | SNB-19 | NPCs |
| NCGC00346477-01 | Emricasan | C | 0.46 | 0.62 | 0.37 | 4.11 | 0.87 | 3.88 | 77.1 | 97.6 | 85.3 | 98.7 | 194 | 54.4 |
| NCGC00263218-02 | Teriflunomide | C | 1.30 | 1.03 | 0.92 | — | — | — | 86.9 | 93.1 | 94.5 | 0.0 | 0.0 | −86.9 |
| NCGC00346732-02 | Hydroxocobalamin | C | 0.97 | 1.46 | 0.87 | — | — | — | 83.4 | 85.7 | 67.4 | 0.0 | 0.0 | 0.0 |
| NCGC00166262-03 | Ensulizole | B | 1.95 | 1.84 | 1.38 | — | — | — | 82.7 | 73.3 | 80.6 | 0.0 | 0.0 | 0.0 |
| NCGC00160655-03 | Tenonitrozole | B | 2.06 | 1.95 | 1.30 | — | — | — | 88.8 | 81.7 | 81.5 | 0.0 | 0.0 | −47.2 |
| NCGC00090504-08 | Isoliquiritigenin | A | 3.08 | 2.18 | 1.84 | — | 3.08 | — | 95.1 | 96.9 | 89.0 | 0.0 | 36.3 | −46.1 |
| NCGC00090774-03 | Nitazoxanide | B | 2.00 | 2.24 | 1.26 | 31.6 | 23.7 | — | 90.3 | 86.4 | 82.3 | 53.6 | 62.1 | −68.9 |
| NCGC00182059-02 | Febuxostat | B | 2.31 | 2.91 | 3.88 | — | 3.66 | — | 84.8 | 104 | 83.2 | 0.0 | 68.4 | −43.8 |
| NCGC00015610-12 | Leflunomide | B | 4.35 | 3.27 | 1.38 | — | — | — | 98.1 | 106 | 97.8 | 0.0 | 0.0 | −55.6 |
| NCGC00345056-01 | Vidofludimus | C | 2.91 | 3.66 | 2.45 | — | — | — | 101 | 101 | 87.8 | 0.0 | 0.0 | 0.0 |
| NCGC00094344-03 | SB-366791 | A | 4.11 | 3.66 | 2.91 | — | — | — | 93.9 | 93.3 | 89.9 | 0.0 | 0.0 | −42.0 |
| NCGC00015420-08 | Emodin | A | 3.27 | 4.35 | 2.59 | — | — | — | 86.4 | 83.3 | 82.1 | 0.0 | 0.0 | 0.0 |
| NCGC00164168-02 | Diphenyl isophthalate | B | 6.68 | 4.73 | 4.47 | — | — | — | 104 | 92.8 | 89.4 | 0.0 | 0.0 | 0.0 |
| NCGC00164513-02 | Benzoylpas | B | 5.81 | 6.90 | 4.89 | — | — | — | 94.9 | 92.8 | 85.4 | 0.0 | 0.0 | 0.0 |
| NCGC00092384-03 | Fenobam | B | 9.20 | 7.31 | 5.48 | — | 1.73 | — | 97.2 | 110 | 108 | 0.0 | 60.5 | 0.0 |
| NCGC00253758-01 | Indobufen | B | 6.52 | 7.74 | 6.15 | — | — | — | 86.3 | 85.8 | 81.3 | 0.0 | 0.0 | 0.0 |
| NCGC00166243-03 | 2-(2H-Benzotriazol-2-yl)-4-methylphenol | B | 9.20 | 8.69 | 4.89 | — | — | — | 68.5 | 80.1 | 77.6 | 0.0 | 0.0 | 0.0 |
| NCGC00263191-01 | PHA-690509 | C | 13.0 | 9.20 | 19.5 | 7.74 | 10.9 | — | 71.6 | 74.6 | 73.0 | 81.9 | 165 | −60.6 |
| NCGC00179573-03 | Tiaprofenic acid | B | 6.15 | 10.3 | 8.69 | — | — | — | 88.2 | 96.2 | 86.7 | 0.0 | 0.0 | 0.0 |
| NCGC00016490-12 | Flufenamic acid | B | 8.69 | 10.9 | 17.3 | — | — | — | 71.9 | 61.5 | 68.1 | 0.0 | 0.0 | 0.0 |
| NCGC00249888-01 | Vitamin B12 | B | 8.69 | 11.6 | 6.90 | — | — | — | 77.1 | 101 | 94.7 | 0.0 | 0.0 | 0.0 |
| NCGC00024599-04 | Cinanserin | B | 15.5 | 12.3 | 17.3 | — | 19.5 | — | 80.2 | 92.0 | 80.4 | 0.0 | 56.9 | 0.0 |
| NCGC00015740-10 | 5-Nitro-2-(3-phenylpropylamino) benzoic acid | A | 9.75 | 13.0 | 8.69 | — | — | — | 82.1 | 82.9 | 59.8 | 0.0 | 0.0 | 0.0 |
| NCGC00250411-01 | Veliflapon | C | 9.20 | 13.8 | 9.75 | — | — | — | 65.9 | 70.0 | 74.3 | 0.0 | 0.0 | −36.0 |
| NCGC00016410-13 | Thiabendazole | B | 10.3 | 14.6 | 9.75 | — | — | — | 81.0 | 89.4 | 83.4 | 0.0 | 0.0 | 0.0 |
| NCGC00025046-05 | SIB 1893 | A | 12.3 | 15.5 | 8.69 | — | — | — | 96.2 | 105 | 95.2 | 0.0 | 0.0 | 0.0 |
| NCGC00167471-02 | Anethole trithione | B | 13.8 | 15.5 | 13.0 | — | — | — | 62.7 | 85.5 | 70.3 | 0.0 | 0.0 | 0.0 |
| NCGC00016457-03 | Naringenin | C | 17.3 | 15.5 | 15.5 | — | — | — | 65.2 | 66.3 | 63.4 | 0.0 | 0.0 | −32.5 |
| NCGC00018130-09 | Phenazopyridine hydrochloride | B | 15.5 | 16.4 | 11.6 | — | 27.5 | — | 69.9 | 73.7 | 72.5 | 0.0 | 35.3 | −38.1 |
| NCGC00160438-02 | Fanetizole | B | 10.9 | 17.3 | 14.6 | — | — | — | 72.9 | 78.1 | 81.8 | 0.0 | 0.0 | 0.0 |
| NCGC00016026-08 | Terazosin hydrochloride | B | 12.3 | 17.3 | 10.9 | — | — | — | 88.9 | 77.3 | 84.4 | 0.0 | 0.0 | 0.0 |
| NCGC00018274-05 | Diacerein | B | 15.5 | 17.3 | 15.5 | 30.8 | — | — | 72.9 | 63.2 | 56.5 | 35.2 | 0.0 | 0.0 |
| NCGC00346625-01 | CAY10505 | C | 16.4 | 17.3 | 10.9 | — | — | — | 80.1 | 91.2 | 83.5 | 0.0 | 0.0 | 0.0 |
| NCGC00163540-03 | Hesperetin | C | 16.4 | 17.3 | 10.9 | — | — | — | 72.7 | 86.0 | 79.6 | 0.0 | 0.0 | −52.8 |
| NCGC00094916-06 | Suprofen | B | 19.5 | 17.3 | 15.5 | — | — | — | 64.5 | 65.6 | 59.1 | 0.0 | 0.0 | 0.0 |
| NCGC00185990-01 | Ketorolac tromethamine | B | 21.8 | 17.3 | 10.3 | — | — | — | 61.7 | 84.5 | 75.0 | 0.0 | 0.0 | 0.0 |
| NCGC00094872-08 | Piperine | C | 20.6 | 19.5 | 13.8 | — | — | — | 73.9 | 75.5 | 66.0 | 0.0 | 0.0 | −44.4 |
| NCGC00344543-01 | Pirarubicin | B | 13.8 | 20.6 | — | — | — | — | 59.8 | 63.9 | 51.5 | 0.0 | 0.0 | −87.7 |
| NCGC00263135-01 | Piraxostat | C | 8.91 | 21.1 | 15.8 | 63.1 | 5.01 | — | 70.5 | 63.5 | 67.1 | 34.7 | 60.3 | −39.7 |
| NCGC00253760-01 | Albendazole oxide | B | 15.5 | 21.8 | 12.3 | — | — | — | 78.8 | 86.0 | 88.1 | 0.0 | 0.0 | −62.1 |
| NCGC00016019-06 | Tyrphostin AG 494 | A | 18.4 | 21.8 | 17.3 | — | 30.8 | — | 72.5 | 55.6 | 72.8 | 0.0 | 45.6 | −62.9 |
| NCGC00346737-01 | Genistin | C | 25.9 | 23.1 | 17.3 | — | — | — | 60.2 | 58.1 | 58.6 | 0.0 | 0.0 | −80.6 |
| NCGC00016834-07 | Fenbufen | B | 21.8 | 24.5 | 19.5 | — | — | — | 81.5 | 76.3 | 72.5 | 0.0 | 0.0 | 0.0 |
| NCGC00249393-01 | Apatinib | C | 19.5 | 24.5 | — | — | — | — | 57.9 | 61.2 | 0.0 | 0.0 | 0.0 | 0.0 |
| NCGC00159570-01 | RITA | C | 27.5 | 0.22 | 14.6 | 5.81 | — | — | 41.2 | 101 | 50.9 | 81.7 | 0.0 | −91.4 |
| NCGC00015735-08 | Niclosamide | B | 1.84 | 2.06 | 1.84 | 1.73 | 1.95 | — | 96.8 | 93.9 | 87.5 | 51.2 | 97.3 | −77.4 |
| NCGC00162305-03 | BF-170 hydrochloride | A | 4.61 | 6.15 | 4.11 | 6.15 | — | — | 118 | 104 | 92.7 | 65.8 | 0.0 | −61.1 |
| NCGC00263159-01 | OSI-930 | C | 8.20 | 6.90 | 6.90 | — | 3.08 | — | 91.5 | 114 | 96.9 | 0.0 | 71.2 | −56.2 |
| NCGC00159476-09 | Tribromsalan | B | 6.90 | 7.74 | 13.8 | — | — | — | 102 | 107 | 108 | 0.0 | 0.0 | −35.7 |
| NCGC00014684-04 | Pifexole | B | 6.90 | 8.20 | 4.61 | — | — | — | 86.3 | 83.6 | 92.2 | 0.0 | 0.0 | −35.3 |
| NCGC00017269-06 | Formononetin | C | 14.6 | 12.3 | 10.9 | — | — | — | 94.7 | 104 | 88.3 | 0.0 | 0.0 | −56.0 |
| NCGC00015412-13 | Ebselen | A | 8.20 | 17.3 | 8.20 | — | — | — | 93.8 | 117 | 109 | 0.0 | 0.0 | −82.0 |
| NCGC00018185-07 | Tranilast | C | 17.3 | 17.3 | 19.5 | — | — | — | 71.6 | 70.3 | 107 | 0.0 | 0.0 | −54.5 |
| NCGC00164155-02 | Benzylparaben | B | 17.3 | 19.5 | 15.5 | — | — | — | 62.8 | 91.8 | 56.0 | 0.0 | 0.0 | 0.0 |
| NCGC00249899-01 | 2-Ethoxyethyl-p-methoxycinnamate | B | — | 27.5 | 18.4 | — | — | — | 0.0 | 53.0 | 56.0 | 0.0 | 0.0 | 0.0 |
| NCGC00017236-08 | Baicalein | C | — | 29.1 | 18.4 | — | — | — | 0.0 | 50.6 | 57.5 | 0.0 | 0.0 | −69.3 |
| NCGC00319019-01 | Nemorubicin | B | 15.5 | 30.8 | — | 0.87 | 0.41 | — | 42.6 | 53.1 | 82.9 | 146 | 117 | −57.2 |
| NCGC00015892-05 | Rutaecarpine | A | 4.89 | 5.18 | 4.61 | — | — | — | 89.5 | 86.4 | 87.5 | 0.0 | 0.0 | −44.7 |
| NCGC00015682-02 | MPEP | A | 5.81 | 5.18 | 4.11 | — | — | — | 118 | 98.6 | 96.1 | 0.0 | 0.0 | 0.0 |
| NCGC00016456-12 | 5,7-Dihydroxyflavone | C | 15.5 | 8.69 | 5.48 | — | — | — | 55.1 | 42.7 | 51.0 | 0.0 | 0.0 | −69.3 |

TABLE 7-continued

List of compounds including 35 confirmed compounds determined in the
caspase 3/7 assay with hNPCs, SNB-19 cells, and human astrocytes.

| SampleID | Name | Library | Caspase 3 (IC50, uM) | | | Cell viability (IC50, uM) | | | Caspase 3 (efficacy, %) | | | Cell viability (efficacy, %) | | |
|---|---|---|---|---|---|---|---|---|---|---|---|---|---|---|
| | | | Astrocyte | SNB-19 | NPCs | Astrocyte | SNB-19 | NPCs | Astrocyte | SNB-19 | NPCs | Astrocyte | SNB-19 | NPCs |
| NCGC00249888-04 | Vitamin B12 | B | 6.73 | 13.4 | 11.3 | — | 0.12 | — | 62.7 | 43.0 | 59.1 | 0.0 | 67.3 | 0.0 |
| NCGC00160646-02 | Pipofezine | B | 11.3 | 15.1 | 12.0 | — | — | — | 56.3 | 31.5 | 47.7 | 0.0 | 0.0 | 0.0 |
| NCGC00182710-02 | Flurbiprofen axetil | B | 21.8 | 19.5 | — | — | — | — | 65.5 | 45.7 | 0.0 | 0.0 | 0.0 | 0.0 |
| NCGC00091632-02 | 2-Amino-6-nitrobenzothiazole | B | 39.8 | 53.1 | 56.2 | — | — | — | 54.1 | 46.1 | 57.1 | 0.0 | 0.0 | 0.0 |
| NCGC00013058-02 | Malachite green oxalate | B | 17.3 | — | 21.8 | — | — | — | 54.0 | 0.0 | 62.7 | 0.0 | 0.0 | −89.7 |
| NCGC00262948-01 | Enfenamic acid | B | 25.9 | — | 21.8 | — | — | 7.74 | 58.0 | 49.5 | 47.1 | 0.0 | 0.0 | 58.5 |
| NCGC00091080-03 | Fenaminosulf | B | 35.5 | — | — | — | 15.8 | — | 58.5 | 0.0 | 0.0 | 0.0 | 36.7 | −53.0 |
| NCGC00185997-02 | AS-252424 | A | 1.73 | 2.18 | 1.64 | — | — | — | 37.5 | 38.0 | 52.3 | 0.0 | 0.0 | 0.0 |
| NCGC00163250-02 | Phenserine | A | 25.9 | 19.5 | 25.9 | — | — | — | 47.4 | 38.4 | 51.5 | 0.0 | 0.0 | −105 |
| NCGC00164613-03 | Epalrestat | C | 19.5 | 20.6 | 15.5 | — | 5.48 | — | 93.3 | 79.2 | 72.1 | 0.0 | 82.1 | −47.9 |
| NCGC00095227-06 | Alizarin | B | 30.8 | 21.8 | 21.8 | — | — | — | 47.9 | 40.9 | 58.5 | 0.0 | 0.0 | 0.0 |
| NCGC00263083-01 | Dalcetrapib | C | — | — | 35.5 | 47.3 | 35.5 | — | 0.0 | 50.2 | 50.2 | 45.7 | 110 | −43.6 |

Note:
the full name of compound can be found in the Pubchem website (pubchem.ncbi.nlm.nih.gov) using the Sample ID number in the first column. A: LOPAC library (Sigma-Aldrich).
B: Approved drug library. C: Clinical drug candidate library.

TABLE 8

$IC_{50}$ values of selected compounds for improving cell viability
in hNPCs, astrocytes and SNB-19 cells following ZIKV infection.

| Compound ID | Compound name | Collection* | $IC_{50}$ (μM) | | |
|---|---|---|---|---|---|
| | | | hNPCs | Astrocytes | SNB-19 |
| NCGC00346477 | Emricasan | C | 3.88 | 4.11 | 0.87 |
| NCGC00263191 | PHA-690509 | C | — | 7.47 | 10.1 |
| NCGC00015735 | Niclosamide | B | — | 1.73 | 1.95 |

Note:
*compound is from "A"—LOPAC library, "B"—approved drug library, and "C"—clinical drug candidate library. "—": n.a.

Figure 17A:
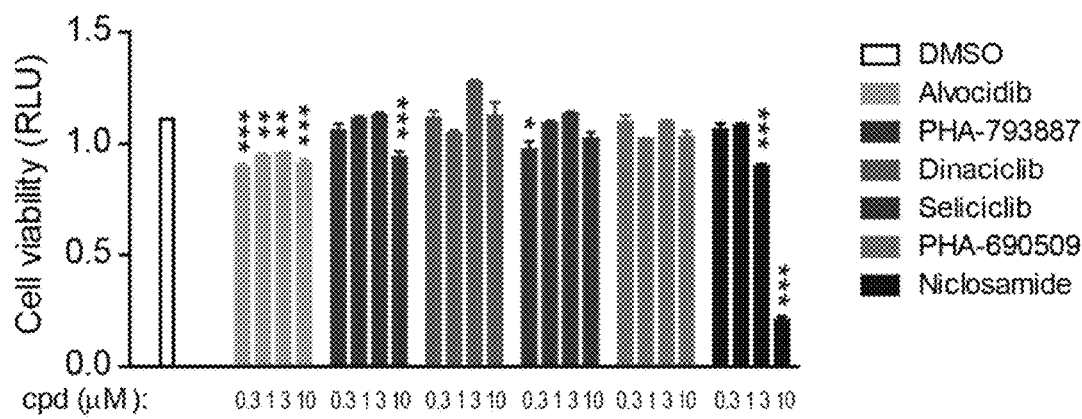
FIGS. 17A-17C. Analysis of potential toxicity of CDKis on human astrocyte viability and hNPC proliferation. Human iPSC-derived astrocytes (BJ line) were treated with each indicated compound (cpd) for 25 hours prior to cell viability analysis as measured in relative luciferase units for ATP production. Results are shown in FIG. 17A. Values represent mean+s.d. (n=3 cultures; *P<0.001; P<0.01; One-way ANOVA for comparison with the DMSO treatment). RLU: relative luminescence units. hNPCs were treated with saline, PHA-690509 (PHA, 1 µM) or Seliciclib (5 µM), 1 hour prior to ZIKV PRVABC59 infection (MOI=0.08). At 72 hours post infection, EdU (10 µM) was added to hNPCs and cells were cultured for additional 4 hours prior to fixation and staining for EdU and DAPI. Results are shown in FIG. 17B. Values represent mean+ s.e.m. (n=3 cultures; ***P<0.001; One-way ANOVA for comparison with the mock treatment). Day 20 forebrain-specific brain organoids were treated with PHA-690509 (1 µM) or Seliciclib (5 µM) for 3 days and hNPC proliferation was evaluated by phospho-Histone 3 (PH3) expression within the ventricular zone. Results are shown in FIG. 17C.
Figure 17B:
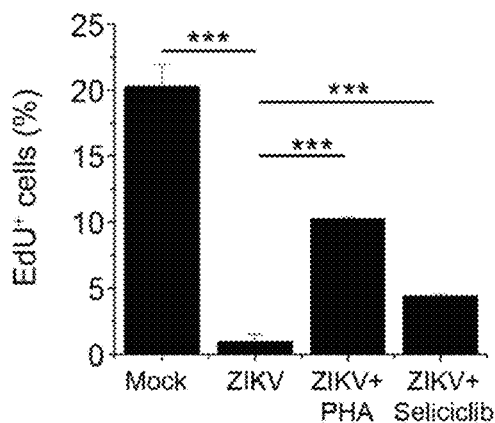
Figure 17C:
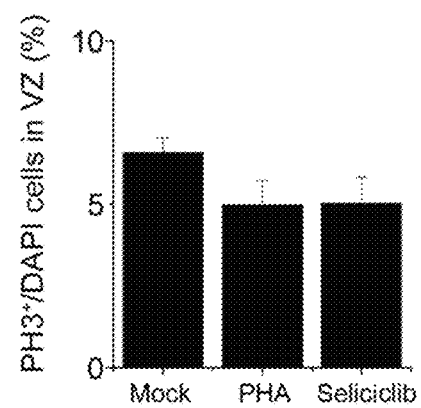

FIGS. 17A-C show toxicity analysis of CDKis on human astrocyte viability and hNPC proliferation. FIGS. 18A to 18G-2 show the antiviral activity of emetine against ZIKV infection. FIGS. 19A to 19E-2 show the antiviral activity of proteasome inhibitors against ZIKV and dengue virus (DENV) infection Example 2—Further Anti-Zika Screen and Anti-Zika Virus Compounds The inventors identified the compounds of Table 9 from a library of compounds used in a large scale compound screen measuring cell-death inhibition in ZIKV infected cells. Each compound having both a NS1 $IC_{50}$ value below $10^{-6}$ M (1 uM) and a ratio of Toxicity $IC_{50}$ (cell-killing activity) to NS1 $IC_{50}$ (virus-inhibiting activity) of 4 or greater was selected as an effective compound.

A one-step NS1 TR-FRET (Time-resolved fluorescence resonance energy transfer) assay for a screen of anti-ZIKV compounds was carried out. Human embryonic kidney cell line HEK293 cells were seeded into 384-well plates and infected with ZIKV MR766 at a MOI of 0.5 for 2 days. The FRET assay was performed with two clones of anti-NS1 antibody (ab) differentially labelled with donor and acceptor fluorophores. Different combinations of antibody dilutions were tested to achieve high and producible signal to noise ratios.

Because this assay is measuring NS1, which a virally-encoded protein, this screen is focused on compounds that have antiviral activities as opposed to compounds that can block ZIKV-induced cell death. The advantage of this FRET assay over the NS1 ELISA assay [47] is it has been adapted to the 384-well format and does not require a washing step. These are advantages as a screening assay.

Each compound having both a NS1 $IC_{50}$ value below $10^{-6}$ M (1 uM) and a ratio of Toxicity $IC_{50}$ (cell-killing activity) to NS1 $IC_{50}$ (virus-inhibiting activity) of 4 or greater was selected as an effective compound. The compounds identified as effective from the screen are listed in Table 9 and their chemical structures shown in Table 10.

TABLE 9

| | Name | NS1-IC50 | Tox IC50 | Tox IC50/NS1 IC50 ratio |
|---|---|---|---|---|
| 1. | SN-38 | 1.13E−08 | No | |
| 2. | Echinomycin | 1.74E−08 | No | |
| 3. | (S)-(+)-Camptothecin | 2.64E−08 | No | |
| 4. | BI-2536 | 4.14E−08 | No | |
| 5. | 10-hydroxycamptothecin | 4.66E−08 | No | |
| 6. | Topotecan hydrochloride | 5.14E−08 | No | |
| 7. | Delanzomib | 5.85E−08 | 3.00E−07 | 5.1 |
| 8. | Volasertib | 6.48E−08 | No | |
| 9. | Ispinesib | 6.74E−08 | 3.75E−05 | 555.9 |
| 10. | PACLITAXEL | 8.94E−08 | No | |
| 11. | FK-506 | 1.04E−07 | No | |
| 12. | Emetine | 1.14E−07 | No | |
| 13. | AVN-944 | 1.36E−07 | 2.00E−05 | 147.0 |
| 14. | Digoxin | 1.52E−07 | 6.00E−05 | 394.2 |
| 15. | Dinaciclib | 1.54E−07 | No | |
| 16. | Vincristine sulfate | 1.56E−07 | No | |
| 17. | Idarubicin hydrochloride | 1.68E−07 | No | |
| 18. | Thapsigargin | 1.71E−07 | 4.00E−05 | 234.5 |
| 19. | Lexibulin hydrochloride | 1.71E−07 | No | |
| 20. | Ixazomib citrate | 1.96E−07 | 1.58E−06 | 8.1 |
| 21. | Cephalomannine | 2.21E−07 | No | |
| 22. | Mitoxantrone | 2.32E−07 | 5.00E−05 | 215.4 |
| 23. | MLN-2238 | 2.34E−07 | 2.13E−06 | 9.1 |
| 24. | Demecolcine | 2.38E−07 | No | |
| 25. | RGB-286147 | 2.68E−07 | No | |
| 26. | Vinorelbine tartrate | 2.70E−07 | No | |
| 27. | Bardoxolone methyl | 2.82E−07 | 2.68E−06 | 9.5 |
| 28. | Cycloheximide | 2.87E−07 | No | |
| 29. | Actinomycin D | 3.52E−07 | No | |
| 30. | AZD-7762 | 3.66E−07 | No | |
| 31. | PF-184 | 3.88E−07 | No | |

TABLE 9-continued

| | Name | NS1-IC50 | Tox IC50 | Tox IC50/NS1 IC50 ratio |
|---|---|---|---|---|
| 32. | CHIR-124 | 4.05E−07 | 3.25E−06 | 8.0 |
| 33. | Cyanein | 4.32E−07 | No | |
| 34. | Triptolide | 4.65E−07 | No | |
| 35. | KX-01 | 4.81E−07 | 1.93E−05 | 40.2 |
| 36. | PF-477736 | 4.89E−07 | No | |
| 37. | Epirubicin hydrochloride | 4.92E−07 | No | |
| 38. | Mycophenolate mofetil | 5.29E−07 | No | |
| 39. | Daunorubicin | 5.36E−07 | No | |
| 40. | Mycophenolic acid | 5.39E−07 | No | |

TABLE 9-continued

| | Name | NS1-IC50 | Tox IC50 | Tox IC50/NS1 IC50 ratio |
|---|---|---|---|---|
| 41. | PIK-75 | 6.16E−07 | No | |
| 42. | Vindesine sulfate salt | 6.64E−07 | No | |
| 43. | Torin-2 | 7.24E−07 | No | |
| 44. | 7-Hydroxystaurosporine | 7.60E−07 | 1.02E−04 | 134.0 |
| 45. | CGP-60474 | 7.94E−07 | 6.00E−05 | 75.6 |
| 46. | Floxuridine | 9.18E−07 | 6.00E−05 | 65.4 |
| 47. | Go-6976 | 9.44E−07 | 2.02E−05 | 21.4 |
| 48. | OSU-03012 | 9.92E−07 | 1.00E−05 | 10.1 |

TABLE 10

Structures

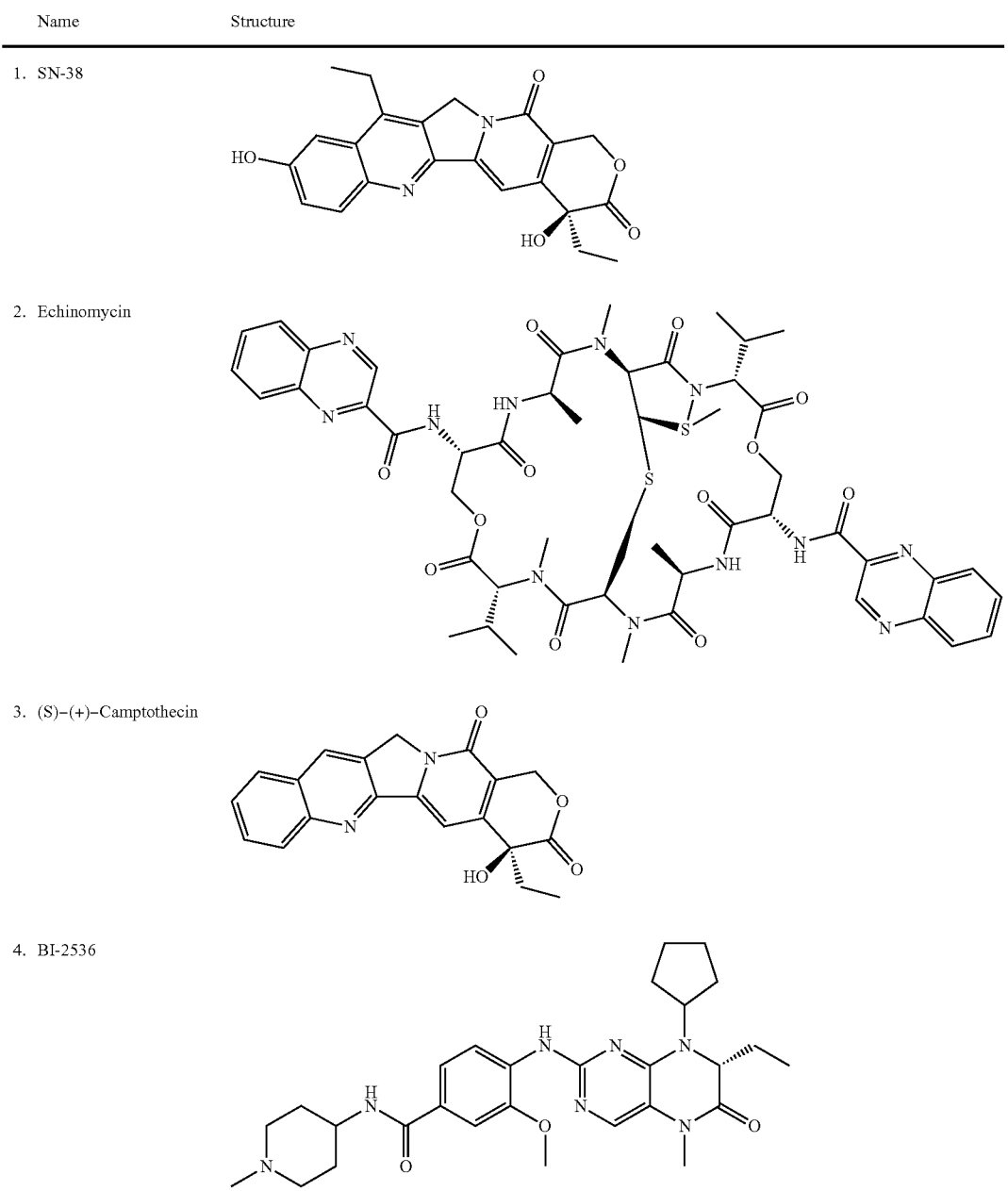

Name / Structure

1. SN-38
2. Echinomycin
3. (S)-(+)-Camptothecin
4. BI-2536

TABLE 10-continued

Structures

| Name | Structure |
|---|---|
| 5. 10-hydroxycamptothecin | |
| 6. Topotecan hydrochloride | |
| 7. Delanzomib | |
| 8. Volasertib | |
| 9. Ispinesib | |

TABLE 10-continued

Structures

| Name | Structure |
| --- | --- |
| 10. PACLITAXEL | |
| 11. FK-506 | |
| 12. Emetine | |
| 13. AVN-944 | |

US 10,940,188 B2
TABLE 10-continued
Structures
| Name | Structure |
|---|---|
| 14. Digoxin | 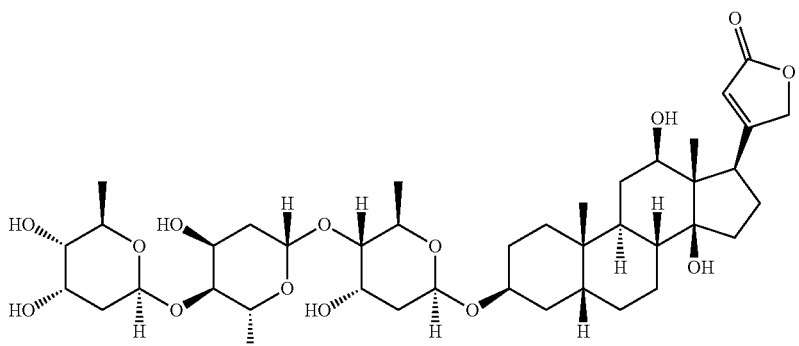 |
| 15. Dinaciclib | 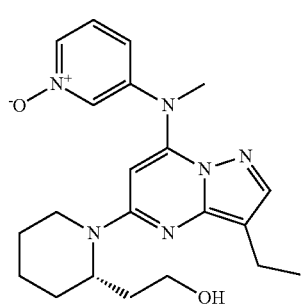 |
| 16. Vincristine sulfate | 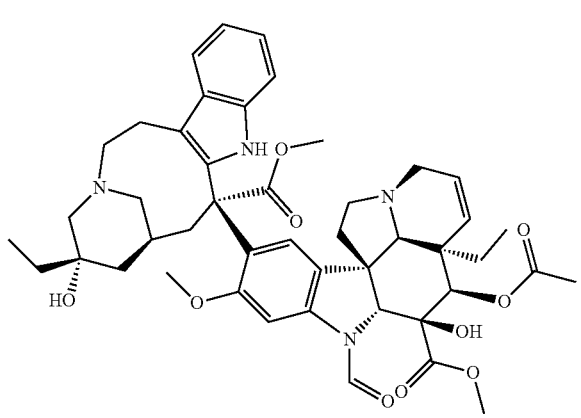 |
| 17. Idarubicin hydrochloride | 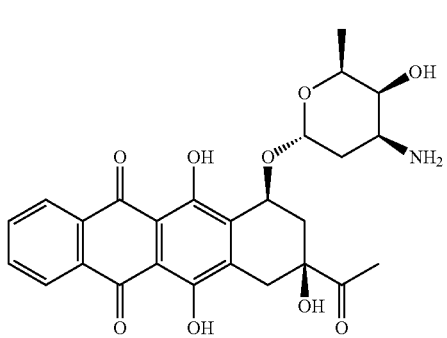 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O] |

TABLE 10-continued
| Structures | |
|---|---|
| Name | Structure |
18. Thapsigargin 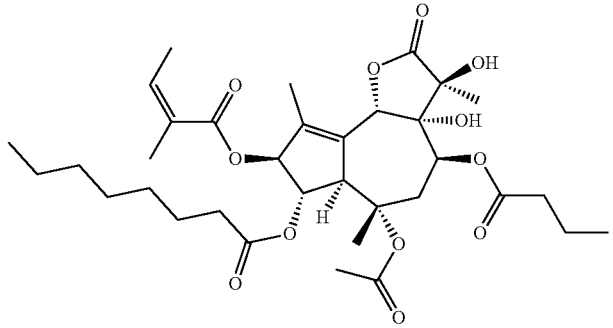 [SMILES: C/C=C(/C)C(=O)O[C@H]1C(C)=C2[C@H]([C@@H]1OC(=O)CCCCCCC)[C@@](C)(OC(C)=O)C[C@H](OC(=O)CCC)[C@@]1(O)[C@H]2OC(=O)[C@@]1(C)O]
19. Lexibulin hydrochloride 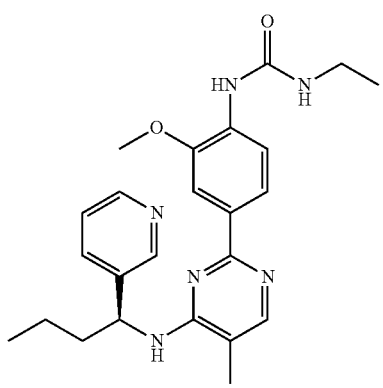 [SMILES: CCC[C@H](Nc1nc(-c2ccc(NC(=O)NCC)c(OC)c2)ncc1C)c1cccnc1]
20. Ixazomib citrate 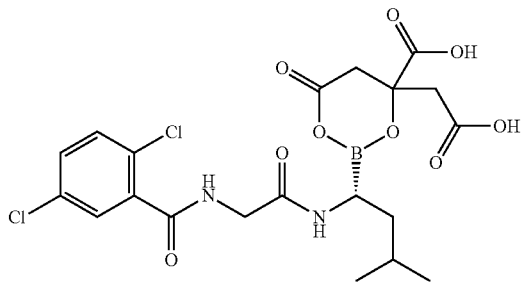 [SMILES: CC(C)C[C@H](NC(=O)CNC(=O)c1cc(Cl)ccc1Cl)B1OC(=O)CC(CC(=O)O)(C(=O)O)O1]
21. Cephalomannine 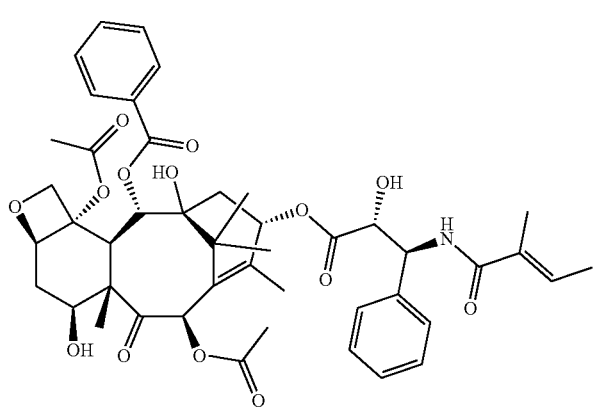 [SMILES: C/C=C(\C)C(=O)N[C@@H](c1ccccc1)[C@@H](O)C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](OC(C)=O)C(=C1C)C2(C)C]

TABLE 10-continued
Structures
| Name | Structure |
|---|---|
| 22. Mitoxantrone | 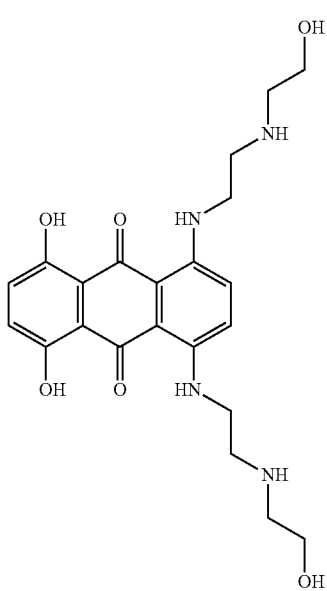 [SMILES: O=C1c2c(O)ccc(O)c2C(=O)c2c(NCCNCCO)ccc(NCCNCCO)c21] |
| 23. MLN-2238 | 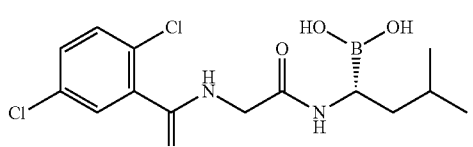 |
| 24. Demecolcine | 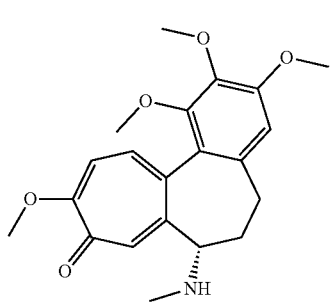 |
| 25. RGB-286147 | 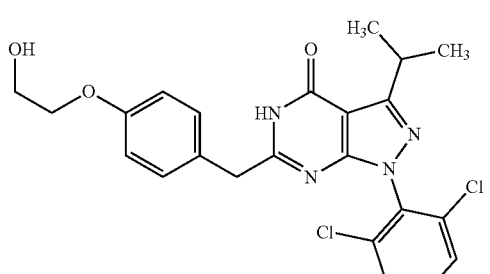 |

TABLE 10-continued

| Name | Structure |
|---|---|
| 26. Vinorelbine tartrate | |
| 27. Bardoxolone methyl | |
| 28. Cycloheximide | |

TABLE 10-continued

Structures

| Name | Structure |
|---|---|
| 29. Actinomycin D | |
| 30. AZD-7762 | |
| 31. PF-184 | |
| 32. CHIR-124 | |
| 33. Cyanein | |

TABLE 10-continued

| Name | Structure |
|---|---|
| 34. Triptolide | |
| 35. KX-01 | |
| 36. PF-477736 | |
| 37. Epirubicin hydrochloride | |
| 38. Mycophenolate mofetil | |

TABLE 10-continued
| Name | Structure |
|---|---|
| 39. Daunorubicin | 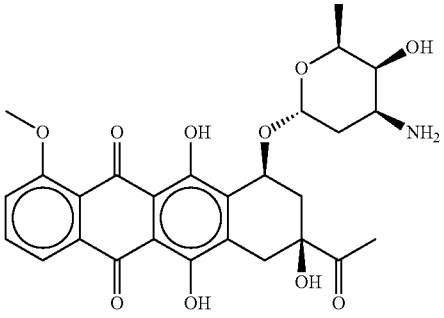 |
| 40. Mycophenolic acid | 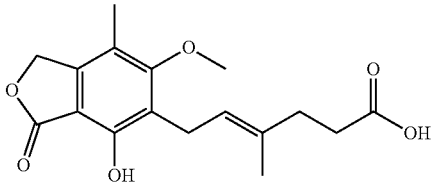 [SMILES: COc1c(C)c2c(c(O)c1C/C=C(\C)CCC(=O)O)C(=O)OC2] |
| 41. PIK-75 | 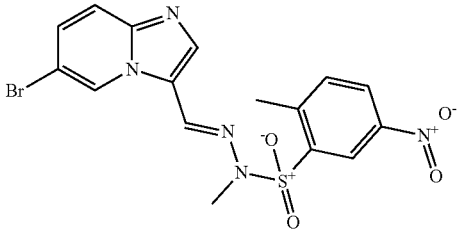 |
| 42. Vindesine sulfate salt | 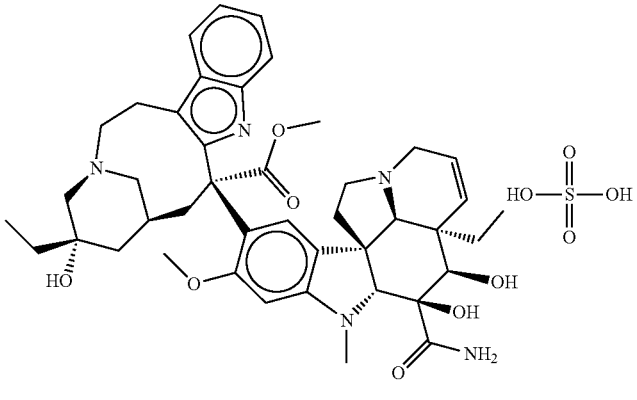 |
| 43. Torin-2 | 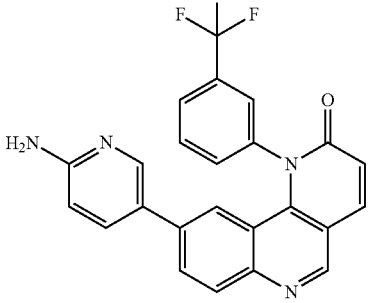 |

TABLE 10-continued

| Name | Structure |
| --- | --- |
| 44. 7-Hydroxystaurosporine | |
| 45. CGP-60474 | |
| 46. Floxuride | |
| 47. Go-6976 | |
| 48. OSU-03012 | |

Example 3—Antiviral Activity of Niclosamide Derivatives

A scheme for the synthesis of the Niclosamide derivative 5-Chloro-N-(2-chloro-4-nitrophenyl)-2-(phosphonooxy)-benzamide (also referred to as p-niclosamide) is shown in FIG. 20.

Niclosamide monophosphate 4 can be easily made from commercially available niclosamide 1 in three steps: phosphorylation of 1 followed by TMSBr mediated deprotection of phosphate esters 2 gave trimethylsilyl phosphate 3, subsequent treatment with methanol or water provided desired compound 4.

Step a: Niclosamide 1 (2 mmol) was mixed with 10 mL of anhydrous $CH_3CN$. Then at −10° C. was added $CCl_4$ (10 mmol), DIPEA (4 mmol) and DMAP (0.5 mmol). The reaction mixture was then stirred at this temperature for 10 minutes. Then diethyl phosphate (3 mmol) was added dropwise and the resulting mixture was stirred at −10° C. until reaction was complete. At 0° C., the reaction was quenched with 50 mL of 0.5 mol/L $KH_2PO_4$. The resulting mixture was warmed to room temperature. The mixture was extracted with three 50 mL portions of ethyl acetate. The combined organic layer was then washed with 50 mL of water and brine. The organic extract was dried over magnesium sulphate and concentrated, providing 2 as a pale yellow solid, which was directly used in the next step.

Step b: Under inert atmosphere, to a stirred solution of 2 (2 mmol) in anhydrous $CHCl_3$ at room temperature was added $(CH_3)_3SiBr$ (10 mmol). The reaction mixture was concentrated under vacuum after overnight stirring at room temperature. The resulting 3 was directly used in the next step.

Step c: At 0° C., 3 was mixed with 6 mL dry MeOH. The solution was then warm to rt and stirred at rt. After 30 minutes, LC-MS found no starting material left. The mixture was concentrated, the resulting white solid was treated twice with 10 mL distilled $H_2O$, followed by 5 mL dry MeOH. The resulting white precipitate was then dried under high vacuum overnight, providing 255 mg 4 as a white solid (31%, over three steps). $^1H$ NMR (400 MHz, DMSO-$d_6$) δ 10.50 (s, 1H), 8.48 (d, J=9.1 Hz, 1H), 8.41 (d, J=2.7 Hz, 1H), 8.29 (dd, J=2.6, 9.1 Hz, 1H), 7.83 (dd, J=0.9, 2.8 Hz, 1H), 7.68 (dd, J=2.8, 8.9 Hz, 1H), 7.55 (dd, J=1.1, 8.9 Hz, 1H), 3.17 (s, 2H). LC/MS (Long Gradient 4% to 100% Acetonitrile (0.05% TFA) over 7 minutes, Agilent Eclipse XDB-C18 3 micron 3×75 mm): (electrospray+ve), m/z 407.0 (MH)$^+$, $t_R$=3.971, $UV_{254}$=100%.

FIGS. 21 and 22 show the antiviral activity of niclosamide derivatives n-Niclosamide and DK-520, respectively, against ZIKV infection in human glioblastoma SNB-19 cells.

Example 4—Evaluation of Compounds in Mice In Vivo

Animal models useful for Zika virus have been reported in the literature (see, for example, Morrison T E et al., *J. Virol.*, 2017, "Animal Models of Zika Virus Infection, Pathogenesis, and Immunity," 91(8):1-15; Dowall S D et al., PLOS Neglected Tropical Diseases, 2016, "A Susceptible Mouse Model for Zika Virus Infection," 10(5):e0004658; Koid F et al., *Front Microbiol.*, 2016, "Development of a Zika Virus Infection Model in Cynomolgus Macaques," 7: 2028; Dudley D M et al., *Nat Commun.*, 2016, "A rhesus macaque model of Asian-lineage Zika virus infection," 28; 7:12204, which are incorporated herein by reference in their entirety.

To further assess the activity of compounds of the invention against ZIKV infection, compounds will be tested in mice. NOD SCID mice have a spontaneous homozygous scid mutation (Prkdc$^{scid}$). They are characterized by an absence of functional T cells and B cells, thus having severe combined immune deficiency (Bosma M J et al., Annu Rev Immunol, 1991, "The SCID mouse mutant: definition, characterization, and potential uses", 9: 323-350). Ifngr KO (AG129) mice have an IFN-alpha/beta receptor (Ifngr) deficiency (homozygous Ifngr1$^{tm1Agt}$). These mice have normal T cell responses but are defective in natural resistance, evidenced by an increased susceptibility to viral infection (Huang, S W et al., *Science*, 1993, "Immune response in mice that lack the interferon-gamma receptor," 259(5102): 1742-1745). SJL is an inbred strain that contains a naturally-occurring dysferlin mutation and was originally developed from three different sources of Swiss Webster mice. CD-1 is an outbred mouse line most commonly used in toxicology and carcinogenicity bioassays.

In Vivo Infection:

Pregnant mice of SCID, AG129, SJL or CD-1 strain, will be infected through footpad injection with ZIKV-containing saline on day 6-14 of gestation. Footpad injection is a combination of intradermal and subcutaneous injections used primarily in models of immunization and to administer certain types of pathogens. This route of injection has been successfully utilized to infect certain strains of immune deficient mice (Lazear H M J et al., *Cell Host Microbe*, 2016, "A Mouse Model of Zika Virus Pathogenesis" 19(5):720-30).

For safe and effective footpad injection, a published protocol that uses a hands-free method to deliver infectious material will be followed (Long K M et al., *Methods Mol Biol*, 2013, "Safe and effective mouse footpad inoculation" 1031: 97-100). Briefly, after inserting the animal into a commercial mouse restrainer, the foot to be injected (hind foot) will be pulled to the outside of the restrainer with the ventral side of the foot facing upwards. Straight, atraumatic forceps will be used to grasp the foot just above the toes. A needle (25G or smaller) will be laid on top of the foot with bevel side up and inserted just under the skin between the walking pads and the heel. A volume of 10-50 μl (volume dependent on titer of solution; a dose of $10^3$-$10^5$ infectious particles per animal) of ZIKV or saline will be injected in a slow motion into each animal. 3-5 seconds after the delivery, the needle will be withdrawn slowly from the injection site. Firm pressure will be maintained on the injection site for a few seconds once the needle is removed, so that no injected material should be leaking from the injection site. After removing needle, the foot with the forceps will be released and the mouse returned to its cage.

A potential alternative to footpad injection is injecting into the hock rather than the foot; however, previous studies have used the footpad route (for replication of technique). Also, no adjuvant or irritating chemical is being used, only 1 foot will be injected using a non-adjuvant diluent and no repeat injections will occur.

Niclosamide and Niclosamide Derivatives

Niclosamide is an FDA-approved drug for use in humans to treat worm infections and is well tolerated. It has low toxicity in mammals with an oral LD50 of 45 mg/g in rats. The potency of Niclosamide on inhibition of ZIKV replication is in the submicromolar range, whereas clinically it can be reached at micromolar levels.

Prospective Treatment Protocol:
- Vehicle: saline
- Route of Administration: IP injection; food feed or oral garvage.
- Proposed dosage: 20-100 mg/Kg
- Number of doses: up to 7
- Interval between doses: 1 day
- Pre-treatment of animals: not necessary Emricasan and Emricasan Derivatives Emricasan, also named IDN-6556 or PF-03491390, is an inhibitor of activated caspases with sub- to nano-molar activity in vitro. Emricasan is currently being evaluated in Phase II clinical trials to reduce hepatic injury and liver fibrosis caused by chronic HCV infection, and has been well tolerated in human trials without significant adverse events. It was reported that overall and maximum concentrations of Emricasan (oral delivery, BID, ×4 days) in human blood were 1.90 µg/ml (3.35 µM) and 2.36 µg/ml (4.15 respectively. Therefore, the reported human plasma concentration of Emricasan is about 10-fold higher than the IC50 for inhibition of increased caspase-3 activity and cell death caused by ZIKV infection in vitro.

Prospective Treatment Protocol:
- Vehicle: saline
- Route of Administration: IP injection, food feed or oral garvage.
- Proposed dosage: 5-50 mg/Kg
- Number of doses: up to 7
- Interval between doses: 1 day
- Pre-treatment of animals: not necessary CDK Inhibitors and Derivatives Many CDKis are being evaluated in clinical trials for various cancers, Cytic Fibrosis, and Cushings Disease, but some of these compounds may not be suitable for pregnant women because of potentially hazardous effects on the fetus. In the in vitro analyses herein, treatment with PHA-690509 or Seleciclib partially rescued ZIKV-induced reduction of hNPC proliferation and the treatment itself exhibited a minimal effect on hNPC proliferation in brain organoids, which model early human brain development in vitro. These CDKis and their derivatives may be useful for treating non-pregnant humans who face an increased risk of Guillain-Barré syndrome and other conditions following ZIKV infection. For example, viral RNA and infectious virus have been detected in the semen of men weeks after acute symptoms have resolved. A reduction in viral load in men can potentially cut down transmission risk.

Prospective Treatment Protocol:
- Vehicle: saline
- Route of Administration: IP injection; food feed or oral garvage.
- Proposed dosage: 20-100 mg/Kg
- Number of doses: up to 7
- Interval between doses: 1 day
- Pre-treatment of animals: not necessary It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Dick, G. W., Kitchen, S. F. & Haddow, A. J. Zika virus. I. Isolations and serological specificity. *Trans R Soc Trop Med Hyg* 46, 509-520 (1952).
2. Duffy, M. R., et al. Zika virus outbreak on Yap Island, Federated States of Micronesia. *N Engl J Med* 360, 2536-2543 (2009).
3. Cao-Lormeau, V. M., et al. Zika virus, French polynesia, South pacific, 2013. *Emerg Infect Dis* 20, 1085-1086 (2014).
4. Musso, D. Zika Virus Transmission from French Polynesia to Brazil. *Emerg Infect Dis* 21, 1887 (2015).
5. Heymann, D. L., et al. Zika virus and microcephaly: why is this situation a PHEIC? *Lancet* 387, 719-721 (2016).
6. Mlakar, J., et al. Zika Virus Associated with Microcephaly. *N Engl J Med* 374, 951-958 (2016).
7. Rasmussen, S. A., Jamieson, D. J., Honein, M. A. & Petersen, L. R. Zika Virus and Birth Defects—Reviewing the Evidence for Causality. *N Engl J Med* 374, 1981-1987 (2016).
8. Cao-Lormeau, V. M., et al. Guillain-Barre Syndrome outbreak associated with Zika virus infection in French Polynesia: a case-control study. *Lancet* 387, 1531-1539 (2016).
9. Araujo, L. M., Ferreira, M. L. & Nascimento, O. J. Guillain-Barre syndrome associated with the Zika virus outbreak in Brazil. *Arq Neuropsiquiatr* 74, 253-255 (2016).
10. Tang, H., et al. Zika Virus Infects Human Cortical Neural Progenitors and Attenuates Their Growth. *Cell Stem Cell* 18, 587-590 (2016).
11. Garcez, P. P., et al. Zika virus impairs growth in human neurospheres and brain organoids. *Science* 352, 816-818 (2016).
12. Qian, X., et al. Brain-Region-Specific Organoids Using Mini-bioreactors for Modeling ZIKV Exposure. *Cell* 165, 1238-1254 (2016).
13. Rossi, S. L., et al. Characterization of a Novel Murine Model to Study Zika Virus. *Am J Trop Med Hyg* (2016).
14. Lazear, H. M., et al. A Mouse Model of Zika Virus Pathogenesis. *Cell Host Microbe* (2016).
15. Cugola, F. R., et al. The Brazilian Zika virus strain causes birth defects in experimental models. *Nature* 534, 267-271 (2016).
16. Li, C., et al. Zika Virus Disrupts Neural Progenitor Development and Leads to Microcephaly in Mice. *Cell Stem Cell* (2016).
17. Miner, J. J., et al. Zika Virus Infection during Pregnancy in Mice Causes Placental Damage and Fetal Demise. *Cell* 165, 1081-1091 (2016).
18. Mlakar, J., et al. Zika Virus Associated with Microcephaly. *N Engl J Med* (2016).
19. Driggers, R. W., et al. Zika Virus Infection with Prolonged Maternal Viremia and Fetal Brain Abnormalities. *N Engl J Med* (2016).
20. Dang, J., et al. Zika Virus Depletes Neural Progenitors in Human Cerebral Organoids through Activation of the Innate Immune Receptor TLR3. *Cell Stem Cell* (2016).
21. Zheng, W., Thorne, N. & McKew, J. C. Phenotypic screens as a renewed approach for drug discovery. *Drug Discov Today* 18, 1067-1073 (2013).
22. Sun, W., Sanderson, P. E. & Zheng, W. Drug combination therapy increases successful drug repositioning. *Drug Discov Today* (2016).

23. Kouznetsova, J., et al. Identification of 53 compounds that block Ebola virus-like particle entry via a repurposing screen of approved drugs. *Emerg Microbes Infect* 3, e84 (2014).
24. Johansen, L. M., et al. A screen of approved drugs and molecular probes identifies therapeutics with anti-Ebola virus activity. *Sci Transl Med* 7, 290ra289 (2015).
25. Chen, C. Z., et al. High-throughput *Giardia lamblia* viability assay using bioluminescent ATP content measurements. *Antimicrob Agents Chemother* 55, 667-675 (2011).
26. Debnath, A., et al. A high-throughput drug screen for *Entamoeba histolytica* identifies a new lead and target. *Nat Med* 18, 956-960 (2012).
27. Sun, W., et al. Chemical signatures and new drug targets for gametocytocidal drug development. *Sci Rep* 4, 3743 (2014).
28. Sun, W., et al. Rapid identification of antifungal compounds against *Exserohilum rostratum* using high throughput drug repurposing screens. *PLoS One* 8, e70506 (2013).
29. He, S., et al. Repurposing of the antihistamine chlorcyclizine and related compounds for treatment of hepatitis C virus infection. *Sci Transl Med* 7, 282ra249 (2015).
30. Zhang, J. H., Chung, T. D. & Oldenburg, K. R. A Simple Statistical Parameter for Use in Evaluation and Validation of High Throughput Screening Assays. *J Biomol Screen* 4, 67-73 (1999).
31. Hamel, R., et al. Biology of Zika Virus Infection in Human Skin Cells. *J Virol* 89, 8880-8896 (2015).
32. Nowakowski, T. J., et al. Expression Analysis Highlights AXL as a Candidate Zika Virus Entry Receptor in Neural Stem Cells. *Cell Stem Cell* 18, 591-596 (2016).
33. Schang, L. M., St Vincent, M. R. & Lacasse, J. J. Five years of progress on cyclin-dependent kinases and other cellular proteins as potential targets for antiviral drugs. *Antivir Chem Chemother* 17, 293-320 (2006).
34. Driggers, R. W., et al. Zika Virus Infection with Prolonged Maternal Viremia and Fetal Brain Abnormalities. *N Engl J Med* 374, 2142-2151 (2016).
35. Barreyro, F. J., et al. The pan-caspase inhibitor Emricasan (IDN-6556) decreases liver injury and fibrosis in a murine model of non-alcoholic steatohepatitis. *Liver Int* 35, 953-966 (2015).
36. Pockros, P. J., et al. Oral IDN-6556, an antiapoptotic caspase inhibitor, may lower aminotransferase activity in patients with chronic hepatitis C. *Hepatology* 46, 324-329 (2007).
37. Shiffman, M. L., et al. Clinical trial: the efficacy and safety of oral PF-03491390, a pancaspase inhibitor—a randomized placebo-controlled study in patients with chronic hepatitis C. *Aliment Pharmacol Ther* 31, 969-978 (2010).
38. Wu, C. J., et al. Inhibition of severe acute respiratory syndrome coronavirus replication by niclosamide. *Antimicrob Agents Chemother* 48, 2693-2696 (2004).
39. Jurgeit, A., et al. Niclosamide is a proton carrier and targets acidic endosomes with broad antiviral effects. *PLoS Pathog* 8, e1002976 (2012).
40. Fang, J., et al. Identification of three antiviral inhibitors against Japanese encephalitis virus from library of pharmacologically active compounds 1280. *PLoS One* 8, e78425 (2013).
41. Wen, Z., et al. Synaptic dysregulation in a human iPS cell model of mental disorders. *Nature* 515, 414-418 (2014).
42. Brennand, K. J., et al. Modelling schizophrenia using human induced pluripotent stem cells. *Nature* 473, 221-225 (2011).
43. Topol, A., et al. Increased abundance of translation machinery in stem cell-derived neural progenitor cells from four schizophrenia patients. *Transl Psychiatry* 5, e662 (2015).
44. Qian, X., et al. Brain-region-specific oragnoids using min-bioreactors for modeling ZIKV exposure. *Cell* (2016).
45. Huang, R., et al. The NCGC pharmaceutical collection: a comprehensive resource of clinically approved drugs enabling repurposing and chemical genomics. *Sci Transl Med* 3, 80ps16 (2011).
46. Wang, Y., Jadhav, A., Southal, N., Huang, R. & Nguyen, D. T. A grid algorithm for high throughput fitting of dose-response curve data. *Curr Chem Genomics* 4, 57-66 (2010).
47. Xu et al. Identification of small-molecule inhibitors of Zika virus infection and induced neural cell death via a drug repurposing screen. *Nature Medicine,* 22(10):1101-1110 (2016).
48. Pan J-X et al., "Niclosamide, an antihelminthic agent, demonstrates antitumor activity by blocking multiple signaling pathways of cancer stem cells," *Chin J Cancer,* 2012, 31(4):178-184.
49. Mook R A et al., Structure-activity studies of Wnt/β-catenin inhibition in the Niclosamide chemotype: Identification of derivatives with improved drug exposure. *Bioorg Med Chem.;* 23 (17): 5829-38 (2015).
50. Malumbres, M et al. CDK inhibitors in cancer therapy: What is next?. *Trends in Pharmacological Sciences.* 29 (1): 16-21 (2008).
51. Asghar U et al., The history and future of targeting cyclin-dependent kinases in cancer therapy. Nat Rev Drug Discov; 14(2): 130-146 (2015).
52. Sanchez-Martinez C et al., Cyclin dependent kinase (CDK) inhibitors as anticancer drugs. *Bioorganic & Medicinal Chemistry Letters*, Volume 25, Issue 17, Pages 3420-3435 (2015).
53. Manasanch E E et al., Proteasome inhibitors in cancer therapy. *Nature Reviews Clinical Oncology.* 14, 417-433 (2017).
54. Dou Q P et al., Overview of Proteasome Inhibitor-Based Anti-cancer Therapies: Perspective on Bortezomib and Second Generation Proteasome Inhibitors versus Future Generation Inhibitors of Ubiquitin-Proteasome System. *Curr Cancer Drug Targets.* 14(6): 517-536 (2014).

We claim:

1. A method for treating or preventing Zika virus infection in a human or non-human animal subject, said method comprising administering an effective amount of emetine, or a pharmaceutically acceptable salt thereof, to a subject in need thereof.

2. The method of claim 1, wherein the subject has the Zika virus infection at the time of said administering, and the emetine or pharmaceutically acceptable salt thereof is administered as therapy.

3. The method of claim 2, further comprising, prior to said administering, identifying the subject as having the Zika virus infection.

4. The method of claim 3, wherein said identifying comprises assaying a biological sample obtained from the subject for the presence of Zika virus nucleic acids or Zika virus proteins.

5. The method of claim 4, wherein said assaying comprises use of reverse transcriptase-polymerase chain reaction (RT-PCR), immunological assay, or Plaque-reduction neutralization testing (PRNT).

6. The method of claim 1, wherein the subject does not have the Zika virus infection at the time of said administering, and the emetine or pharmaceutically acceptable salt thereof is administered as prophylaxis.

7. The method of claim 1, wherein the emetine or pharmaceutically acceptable salt thereof is administered orally, nasally, rectally, parenterally, subcutaneously, intramuscularly, or intravascularly.

8. The method of claim 1, further comprising administering an additional agent for treating or preventing Zika virus infection, or a symptom thereof, in the same formulation as the emetine or pharmaceutically acceptable salt thereof, or in a separate formulation before, during, or after administration of the emetine or pharmaceutically acceptable salt thereof.

9. The method of claim 1, wherein said administering comprises administering a composition to the subject, wherein the composition comprises the emetine or pharmaceutically acceptable salt thereof and a pharmaceutically acceptable buffer, carrier, or diluent.

10. The method of claim 1, wherein the subject is human.

11. The method of claim 1, wherein the subject is human, wherein the human subject has the Zika virus infection at the time of said administering, and the emetine or pharmaceutically acceptable salt thereof is administered as therapy.

12. A method for inhibiting Zika virus infection in human or non-human animal cells in vitro or in vivo, said method comprising contacting an effective amount of emetine, or a pharmaceutically acceptable salt thereof, to a human or non-human animal cell in vitro or in vivo before or after exposure of the cell to Zika virus.

13. The method of claim 12, wherein the human or non-human animal cell is a human cell.

14. The method of claim 12, wherein said contacting is done in vivo.

15. The method of claim 12, wherein said contacting is done in vitro.

16. The method of claim 12, wherein said contacting is done before exposure of the cell to the Zika virus.

17. The method of claim 12, wherein said contacting is done after exposure of the cell to the Zika virus.

18. The method of claim 12, wherein the human or non-animal cell is a human cell, wherein said contacting is done in vivo, and wherein said contacting is done after exposure of the cell to the Zika virus.

* * * * *

UNITED STATES PATENT AND TRADEMARK OFFICE
CERTIFICATE OF CORRECTION

PATENT NO. : 10,940,188 B2
APPLICATION NO. : 16/779132
DATED : March 9, 2021
INVENTOR(S) : Hengli Tang et al.

It is certified that error appears in the above-identified patent and that said Letters Patent is hereby corrected as shown below:

In the Specification

Column 5,
Line 67, "ZIKV-F5513025." should read --ZIKV-FSS13025.--.

Column 55,
Line 15, "bioreactor (Spine)" should read --bioreactor (SpinΩ)--.

Column 59,
Line 52, "(SB) ratio" should read --(S/B) ratio--.

Column 63,
Line 11, "bioreactor (Spine)" should read --bioreactor (SpinΩ)--.
Line 38, "F5513025-ZIKV" should read --FSS13025-ZIKV--.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,940,188 B2

Table 10, Column 83, Structure 26:

" 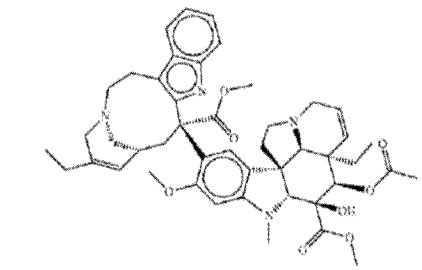 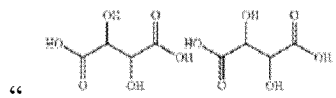 " should read -- 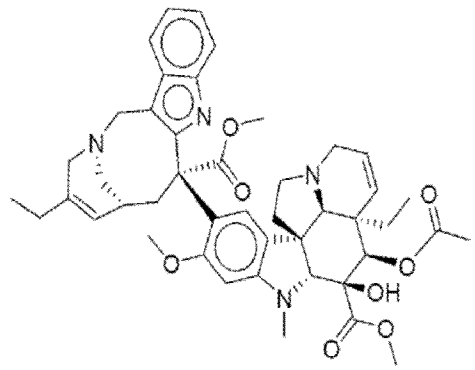 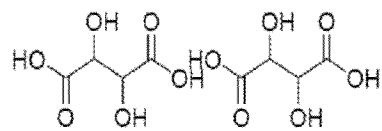 --.